(12) United States Patent  
Huber et al.

(10) Patent No.: US 9,319,964 B2  
(45) Date of Patent: *Apr. 19, 2016

(54) EXCHANGE OF ACCESS CONTROL LISTS TO MANAGE FEMTO CELL COVERAGE

(71) Applicant: AT&T Mobility II LLC, Atlanta, GA (US)

(72) Inventors: Kurt Donald Huber, Kennesaw, GA (US); Judson John Flynn, Decatur, GA (US); William Gordon Mansfield, Sugar Hill, GA (US)

(73) Assignee: AT&T MOBILITY II LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/660,549

(22) Filed: Mar. 17, 2015

(65) Prior Publication Data

US 2015/0189585 A1 Jul. 2, 2015

Related U.S. Application Data

(63) Continuation of application No. 13/675,150, filed on Nov. 13, 2012, now Pat. No. 9,019,819, which is a continuation of application No. 13/316,106, filed on Dec. 9, 2011, now Pat. No. 8,331,228, which is a (Continued)

(51) Int. Cl.  
*H04W 48/20* (2009.01)  
*H04W 68/02* (2009.01)  
(Continued)

(52) U.S. Cl.  
CPC ........... *H04W 48/02* (2013.01); *G06Q 20/1235* (2013.01); *G06Q 20/32* (2013.01);  
(Continued)

(58) Field of Classification Search  
None  
See application file for complete search history.

(56) References Cited

U.S. PATENT DOCUMENTS 5,745,559 A 4/1998 Weir  
5,864,764 A 1/1999 Thro et al.  
(Continued)

FOREIGN PATENT DOCUMENTS

CN 1429005 A 7/2003  
CN 101017554 8/2007  
(Continued)

OTHER PUBLICATIONS

Office Action dated Apr. 17, 2015 for U.S. Appl. No. 14/286,414, 55 Pages.

(Continued)

*Primary Examiner* — Chi H Pham  
*Assistant Examiner* — Soon-Dong D Hyun  
(74) *Attorney, Agent, or Firm* — Amin, Turocy & Watson, LLP

(57) ABSTRACT

Access management to femto cell service is provided through access control list(s), e.g., white list(s), or black list(s). White list(s) include a set of subscriber station(s) identifier numbers, codes, or tokens, and also can include additional fields for femto cell access management based on desired complexity. White list(s) can have associated white list profile(s) therewith to establish logic of femto coverage access based on the white list(s). Access lists exchange among subscribers that posses provisioned femto access points and elect to share access lists also is provided. Transference of access list(s) among subscribers is secured and based at least in part on subscriber privacy policy. Subscribers can be prompted to opt in access list sharing, or to update privacy policies to allow reciprocate sharing and update privacy settings. Based at least in part on association criteria, a component identifies femto access points with which a subscriber accesses lists.

20 Claims, 24 Drawing Sheets

Related U.S. Application Data continuation of application No. 12/276,257, filed on Nov. 21, 2008, now Pat. No. 8,094,551.

(60) Provisional application No. 61/052,813, filed on May 13, 2008.

(51) Int. Cl.

| | | |
|---|---|---|
| *H04W 48/08* | (2009.01) | |
| *H04W 64/00* | (2009.01) | |
| *H04W 48/02* | (2009.01) | |
| *G06Q 20/12* | (2012.01) | |
| *G06Q 20/32* | (2012.01) | |
| *G06Q 20/38* | (2012.01) | |
| *G06Q 20/40* | (2012.01) | |
| *G06Q 30/02* | (2012.01) | |
| *G06Q 30/06* | (2012.01) | |
| *H04L 29/06* | (2006.01) | |
| *H04W 12/08* | (2009.01) | |
| *H04W 48/16* | (2009.01) | |
| *H04W 4/02* | (2009.01) | |
| *H04L 12/24* | (2006.01) | |
| *H04W 8/22* | (2009.01) | |
| *H04W 88/08* | (2009.01) | |
| *H04W 8/20* | (2009.01) | |
| *H04L 5/00* | (2006.01) | |
| *H04W 4/04* | (2009.01) | |
| *H04W 84/04* | (2009.01) | |

(52) U.S. Cl.
CPC ......... *G06Q 20/322* (2013.01); *G06Q 20/3223* (2013.01); *G06Q 20/387* (2013.01); *G06Q 20/405* (2013.01); *G06Q 30/02* (2013.01); *G06Q 30/0222* (2013.01); *G06Q 30/0261* (2013.01); *G06Q 30/0601* (2013.01); *H04L 5/0048* (2013.01); *H04L 41/0803* (2013.01); *H04L 63/101* (2013.01); *H04L 63/108* (2013.01); *H04W 4/02* (2013.01); *H04W 4/023* (2013.01); *H04W 4/027* (2013.01); *H04W 4/046* (2013.01); *H04W 8/20* (2013.01); *H04W 8/22* (2013.01); *H04W 12/08* (2013.01); *H04W 48/08* (2013.01); *H04W 48/16* (2013.01); *H04W 48/20* (2013.01); *H04W 64/006* (2013.01); *H04W 68/02* (2013.01); *H04W 88/08* (2013.01); *H04L 63/0876* (2013.01); *H04L 2209/80* (2013.01); *H04W 84/045* (2013.01)

(56) References Cited

U.S. PATENT DOCUMENTS

| | | | |
|---|---|---|---|
| 5,956,715 | A | 9/1999 | Glasser et al. |
| 6,052,594 | A | 4/2000 | Chuang et al. |
| 6,151,505 | A | 11/2000 | Larkins |
| 6,208,659 | B1 | 3/2001 | Govindarajan et al. |
| 6,219,786 | B1 | 4/2001 | Cunningham et al. |
| 6,256,504 | B1 | 7/2001 | Tell et al. |
| 6,266,537 | B1 | 7/2001 | Kashitani et al. |
| 6,295,454 | B1 | 9/2001 | Havinis et al. |
| 6,363,261 | B1 | 3/2002 | Raghavan |
| 6,483,852 | B1 | 11/2002 | Jacquet et al. |
| 6,484,096 | B2 | 11/2002 | Wong |
| 6,512,478 | B1 | 1/2003 | Chien |
| 6,710,651 | B2 | 3/2004 | Forrester |
| 6,718,023 | B1 | 4/2004 | Zolotov |
| 6,768,722 | B1 | 7/2004 | Katseff et al. |
| 7,080,139 | B1 | 7/2006 | Briggs et al. |
| 7,142,861 | B2 | 11/2006 | Murai |
| 7,146,153 | B2 | 12/2006 | Russell |
| 7,209,739 | B1 | 4/2007 | Narayanabhatla |
| 7,218,912 | B2 | 5/2007 | Erskine et al. |
| 7,277,410 | B2 | 10/2007 | Horneman |
| 7,317,931 | B2 | 1/2008 | Guo |
| 7,370,356 | B1 | 5/2008 | Guo |
| 7,437,755 | B2 | 10/2008 | Farino et al. |
| 7,493,390 | B2 | 2/2009 | Bobde et al. |
| 7,496,383 | B2 | 2/2009 | Kurata |
| 7,509,124 | B2 | 3/2009 | O'Neil |
| 7,516,219 | B2 | 4/2009 | Moghaddam et al. |
| 7,551,574 | B1 | 6/2009 | Peden et al. |
| 7,558,251 | B1 | 7/2009 | Huang et al. |
| 7,574,731 | B2 | 8/2009 | Fascenda et al. |
| 7,613,444 | B2 | 11/2009 | Lindqvist et al. |
| 7,614,078 | B1 | 11/2009 | Stieglitz et al. |
| 7,623,857 | B1 | 11/2009 | O'Neil |
| 7,633,910 | B2 | 12/2009 | Zhun et al. |
| 7,751,826 | B2 | 7/2010 | Gardner |
| 7,761,526 | B2 | 7/2010 | Pounds et al. |
| 7,768,983 | B2 | 8/2010 | Nylander et al. |
| 7,853,265 | B1 | 12/2010 | Ahmad et al. |
| 7,885,644 | B2 | 2/2011 | Gallagher et al. |
| 7,929,537 | B2 | 4/2011 | Vasudevan et al. |
| 7,929,970 | B1 | 4/2011 | Gunasekara |
| 7,941,144 | B2 | 5/2011 | Nylander et al. |
| 7,995,994 | B2 | 8/2011 | Khetawat et al. |
| 8,041,335 | B2 | 10/2011 | Khetawat et al. |
| 8,064,909 | B2 | 11/2011 | Spinelli et al. |
| 8,103,285 | B2 | 1/2012 | Kalhan et al. |
| 8,108,923 | B1 | 1/2012 | Satish et al. |
| 8,265,685 | B2 * | 9/2012 | Vikberg et al. ............... 455/525 |
| 8,437,745 | B2 | 5/2013 | Theppasaandra et al. |
| 8,509,778 | B2 * | 8/2013 | Buchmayer et al. .......... 455/436 |
| 8,510,801 | B2 | 8/2013 | Majumdar et al. |
| 8,522,312 | B2 | 8/2013 | Huber et al. |
| 8,743,776 | B2 | 6/2014 | Gurajala et al. |
| 8,856,878 | B2 | 10/2014 | Wohlert |
| 2002/0044639 | A1 | 4/2002 | Shioda et al. |
| 2002/0077115 | A1 | 6/2002 | Ruutu et al. |
| 2002/0098837 | A1 | 7/2002 | Ferrario et al. |
| 2002/0107018 | A1 | 8/2002 | Nakamura et al. |
| 2002/0123365 | A1 | 9/2002 | Thorson |
| 2002/0142791 | A1 | 10/2002 | Chen et al. |
| 2002/0196187 | A1 | 12/2002 | Holt |
| 2003/0028621 | A1 | 2/2003 | Furlong et al. |
| 2003/0101254 | A1 | 5/2003 | Sato |
| 2003/0109271 | A1 | 6/2003 | Lewis et al. |
| 2003/0125044 | A1 | 7/2003 | Deloach |
| 2003/0125048 | A1 | 7/2003 | Lockhart et al. |
| 2003/0133558 | A1 | 7/2003 | Kung et al. |
| 2003/0139180 | A1 | 7/2003 | McIntosh et al. |
| 2003/0142637 | A1 | 7/2003 | Khawer et al. |
| 2003/0144793 | A1 | 7/2003 | Melaku et al. |
| 2003/0153302 | A1 | 8/2003 | Lewis et al. |
| 2003/0185375 | A1 | 10/2003 | Albal |
| 2004/0003285 | A1 | 1/2004 | Whelan |
| 2004/0111382 | A1 | 6/2004 | Haji-Ioannou |
| 2004/0125781 | A1 | 7/2004 | Walter et al. |
| 2004/0165546 | A1 | 8/2004 | Roskind |
| 2004/0203846 | A1 | 10/2004 | Caronni et al. |
| 2004/0235455 | A1 | 11/2004 | Jiang |
| 2004/0236702 | A1 | 11/2004 | Fink et al. |
| 2004/0258003 | A1 | 12/2004 | Kotot et al. |
| 2004/0264428 | A1 | 12/2004 | Choi et al. |
| 2005/0003797 | A1 | 1/2005 | Baldwin |
| 2005/0009499 | A1 | 1/2005 | Koster |
| 2005/0024201 | A1 | 2/2005 | Culpepper et al. |
| 2005/0026650 | A1 | 2/2005 | Russell |
| 2005/0030929 | A1 | 2/2005 | Swier |
| 2005/0075114 | A1 | 4/2005 | Dennison et al. |
| 2005/0108257 | A1 | 5/2005 | Ishii et al. |
| 2005/0108529 | A1 | 5/2005 | Juneau |
| 2005/0143057 | A1 | 6/2005 | Shiraga et al. |
| 2005/0144279 | A1 | 6/2005 | Wexelblat |
| 2005/0160276 | A1 | 7/2005 | Braun et al. |
| 2005/0172148 | A1 | 8/2005 | Ying |
| 2005/0177645 | A1 | 8/2005 | Dowling et al. |
| 2005/0223389 | A1 | 10/2005 | Klein et al. |
| 2005/0239448 | A1 | 10/2005 | Bayne |

(56) References Cited

U.S. PATENT DOCUMENTS

| | | |
|---|---|---|
| 2005/0239498 A1 | 10/2005 | Dorenbosch et al. |
| 2005/0243057 A1 | 11/2005 | Sugiyama et al. |
| 2005/0250527 A1 | 11/2005 | Jugl |
| 2005/0254451 A1 | 11/2005 | Grosbach |
| 2005/0255893 A1 | 11/2005 | Jin et al. |
| 2005/0259654 A1 | 11/2005 | Faulk, Jr. |
| 2005/0269402 A1 | 12/2005 | Spitzer et al. |
| 2005/0283518 A1 | 12/2005 | Sargent |
| 2006/0031387 A1 | 2/2006 | Hamzeh et al. |
| 2006/0031493 A1 | 2/2006 | Cugi |
| 2006/0046647 A1 | 3/2006 | Parikh et al. |
| 2006/0074814 A1 | 4/2006 | Lovell et al. |
| 2006/0075098 A1 | 4/2006 | Becker et al. |
| 2006/0107327 A1 | 5/2006 | Sprigg et al. |
| 2006/0182074 A1 | 8/2006 | Kubler et al. |
| 2006/0223498 A1 | 10/2006 | Gallagher et al. |
| 2006/0224750 A1 | 10/2006 | Davies et al. |
| 2006/0244589 A1 | 11/2006 | Schranz |
| 2006/0281457 A1 | 12/2006 | Huotari et al. |
| 2007/0002844 A1 | 1/2007 | Ali |
| 2007/0008894 A1 | 1/2007 | Lynch et al. |
| 2007/0025245 A1 | 2/2007 | Porras et al. |
| 2007/0032225 A1 | 2/2007 | Konicek et al. |
| 2007/0032269 A1 | 2/2007 | Shostak |
| 2007/0066318 A1 | 3/2007 | Danzeisen et al. |
| 2007/0074272 A1 | 3/2007 | Watanabe |
| 2007/0094601 A1 | 4/2007 | Greenberg et al. |
| 2007/0094716 A1 | 4/2007 | Farino et al. |
| 2007/0097093 A1 | 5/2007 | Ohshita et al. |
| 2007/0097938 A1 | 5/2007 | Nylander et al. |
| 2007/0097939 A1 | 5/2007 | Nylander et al. |
| 2007/0097983 A1 | 5/2007 | Nylander et al. |
| 2007/0099561 A1 | 5/2007 | Voss |
| 2007/0104166 A1 | 5/2007 | Rahman et al. |
| 2007/0111706 A1 | 5/2007 | Kumar et al. |
| 2007/0123253 A1 | 5/2007 | Simongini et al. |
| 2007/0124802 A1 | 5/2007 | Anton et al. |
| 2007/0129045 A1 | 6/2007 | Aerrabotu |
| 2007/0133563 A1 | 6/2007 | Hundscheidt et al. |
| 2007/0150732 A1 | 6/2007 | Suzuki et al. |
| 2007/0155421 A1 | 7/2007 | Alberth et al. |
| 2007/0167175 A1 | 7/2007 | Wong |
| 2007/0183427 A1 | 8/2007 | Nylander et al. |
| 2007/0184815 A1 | 8/2007 | Aebi |
| 2007/0199076 A1 | 8/2007 | Rensin et al. |
| 2007/0220252 A1 | 9/2007 | Sinko et al. |
| 2007/0232332 A1 | 10/2007 | Holur et al. |
| 2007/0258418 A1 | 11/2007 | Wurtenberger et al. |
| 2007/0270152 A1 | 11/2007 | Nylander et al. |
| 2007/0275739 A1 | 11/2007 | Blackburn |
| 2007/0287501 A1 | 12/2007 | Hoshina |
| 2007/0297373 A1 | 12/2007 | Saifullah et al. |
| 2008/0043972 A1 | 2/2008 | Ruetschi et al. |
| 2008/0049702 A1 | 2/2008 | Meylan et al. |
| 2008/0065752 A1 | 3/2008 | Ch'ng et al. |
| 2008/0070547 A1 | 3/2008 | Schreyer |
| 2008/0072292 A1 | 3/2008 | Narjala |
| 2008/0076386 A1 | 3/2008 | Khetawat |
| 2008/0076392 A1 | 3/2008 | Khetawat et al. |
| 2008/0076393 A1 | 3/2008 | Khetawat et al. |
| 2008/0076398 A1 | 3/2008 | Mate et al. |
| 2008/0076412 A1 | 3/2008 | Khetawat et al. |
| 2008/0076419 A1 | 3/2008 | Khetawat et al. |
| 2008/0076420 A1 | 3/2008 | Khetawat et al. |
| 2008/0076425 A1 | 3/2008 | Khetawat et al. |
| 2008/0081636 A1 | 4/2008 | Nylander et al. |
| 2008/0082538 A1 | 4/2008 | Meijer et al. |
| 2008/0119160 A1 | 5/2008 | Andriantsiferana et al. |
| 2008/0126531 A1 | 5/2008 | Setia et al. |
| 2008/0132239 A1 | 6/2008 | Khetawat et al. |
| 2008/0133742 A1 | 6/2008 | Southiere et al. |
| 2008/0141348 A1 | 6/2008 | Hovnanian |
| 2008/0151807 A1 | 6/2008 | Meier et al. |
| 2008/0168099 A1 | 7/2008 | Skaf |
| 2008/0181184 A1 | 7/2008 | Kezys |
| 2008/0201076 A1 | 8/2008 | Huang et al. |
| 2008/0207170 A1 | 8/2008 | Khetawat et al. |
| 2008/0242280 A1 | 10/2008 | Shapiro et al. |
| 2008/0244148 A1 | 10/2008 | Nix et al. |
| 2008/0254792 A1 | 10/2008 | Ch'ng |
| 2008/0261602 A1 | 10/2008 | Livneh |
| 2008/0274753 A1 | 11/2008 | Attar et al. |
| 2008/0281687 A1 | 11/2008 | Hurwitz et al. |
| 2008/0282327 A1 | 11/2008 | Winget et al. |
| 2008/0293382 A1 | 11/2008 | Lubenski et al. |
| 2008/0293433 A1 | 11/2008 | Wallis |
| 2008/0299984 A1 | 12/2008 | Shimomura |
| 2008/0299992 A1 | 12/2008 | Eitan et al. |
| 2008/0305792 A1 | 12/2008 | Khetawat et al. |
| 2008/0305801 A1 | 12/2008 | Burgess et al. |
| 2008/0305834 A1 | 12/2008 | Janiszewski et al. |
| 2008/0318551 A1 | 12/2008 | Palamara et al. |
| 2009/0012898 A1 | 1/2009 | Sharma et al. |
| 2009/0031006 A1 | 1/2009 | Johnson et al. |
| 2009/0037973 A1 | 2/2009 | Gustave et al. |
| 2009/0042593 A1 | 2/2009 | Yavuz et al. |
| 2009/0046632 A1 | 2/2009 | Nanda et al. |
| 2009/0046665 A1 | 2/2009 | Robson et al. |
| 2009/0047945 A1 | 2/2009 | Zhang |
| 2009/0059822 A1 | 3/2009 | Morrill et al. |
| 2009/0061821 A1 | 3/2009 | Chen et al. |
| 2009/0061873 A1 | 3/2009 | Bao et al. |
| 2009/0077620 A1 | 3/2009 | Ravi et al. |
| 2009/0082010 A1 | 3/2009 | Lee |
| 2009/0082020 A1 | 3/2009 | Ch'ng et al. |
| 2009/0092080 A1 | 4/2009 | Balasubramanian et al. |
| 2009/0092081 A1 | 4/2009 | Balasubramanian et al. |
| 2009/0092096 A1 | 4/2009 | Czaja |
| 2009/0092097 A1 | 4/2009 | Nylander et al. |
| 2009/0093232 A1 | 4/2009 | Gupta et al. |
| 2009/0094351 A1 | 4/2009 | Gupta et al. |
| 2009/0094680 A1 | 4/2009 | Gupta et al. |
| 2009/0097436 A1 | 4/2009 | Vasudevan et al. |
| 2009/0098871 A1 | 4/2009 | Gogic |
| 2009/0109979 A1 | 4/2009 | Tong |
| 2009/0111499 A1 | 4/2009 | Bosch |
| 2009/0119750 A1 | 5/2009 | Sembugamoorthy et al. |
| 2009/0122773 A1 | 5/2009 | Gogic |
| 2009/0124262 A1 | 5/2009 | Vela et al. |
| 2009/0129336 A1 | 5/2009 | Osborn et al. |
| 2009/0129350 A1 | 5/2009 | Khandekar et al. |
| 2009/0131050 A1 | 5/2009 | Osborn |
| 2009/0131098 A1 | 5/2009 | Khandekar et al. |
| 2009/0135749 A1 | 5/2009 | Yang |
| 2009/0135794 A1 | 5/2009 | Su et al. |
| 2009/0156213 A1 | 6/2009 | Spinelli et al. |
| 2009/0161682 A1 | 6/2009 | Johnson et al. |
| 2009/0163216 A1 | 6/2009 | Hoang et al. |
| 2009/0163224 A1 | 6/2009 | Dean |
| 2009/0164547 A1 | 6/2009 | Ch'ng et al. |
| 2009/0170440 A1 | 7/2009 | Eyuboglu et al. |
| 2009/0170528 A1 | 7/2009 | Bull et al. |
| 2009/0180428 A1 | 7/2009 | Viswanath |
| 2009/0191844 A1 | 7/2009 | Morgan et al. |
| 2009/0191845 A1 | 7/2009 | Morgan et al. |
| 2009/0210324 A1 | 8/2009 | Bhogal |
| 2009/0213825 A1 | 8/2009 | Gupta et al. |
| 2009/0215429 A1 | 8/2009 | Caldwell et al. |
| 2009/0215452 A1 | 8/2009 | Balasubramanian et al. |
| 2009/0221303 A1 | 9/2009 | Soliman |
| 2009/0233574 A1 | 9/2009 | Shinozaki |
| 2009/0245176 A1 | 10/2009 | Balasubramanian et al. |
| 2009/0247157 A1* | 10/2009 | Yoon et al. .................. 455/434 |
| 2009/0253421 A1 | 10/2009 | Camp et al. |
| 2009/0253432 A1 | 10/2009 | Willey et al. |
| 2009/0257434 A1 | 10/2009 | Song et al. |
| 2009/0279701 A1 | 11/2009 | Moisand et al. |
| 2009/0288152 A1 | 11/2009 | Huber |
| 2009/0291667 A1 | 11/2009 | Vakil et al. |
| 2009/0299788 A1 | 12/2009 | Huber et al. |
| 2009/0325634 A1 | 12/2009 | Bienas et al. |
| 2010/0022266 A1 | 1/2010 | Villier |
| 2010/0040026 A1 | 2/2010 | Melkesetian |
| 2010/0048165 A1 | 2/2010 | Caldwell et al. |

(56) References Cited

U.S. PATENT DOCUMENTS

| | | | |
|---|---|---|---|
| 2010/0056104 | A1 | 3/2010 | Butler |
| 2010/0075658 | A1 | 3/2010 | Hou |
| 2010/0113067 | A1 | 5/2010 | Fullam et al. |
| 2010/0157941 | A1 | 6/2010 | Raghothaman |
| 2010/0167777 | A1 | 7/2010 | Raghothaman et al. |
| 2010/0260068 | A1 | 10/2010 | Bhatt et al. |
| 2010/0271962 | A1 | 10/2010 | Han |
| 2011/0177794 | A1 | 7/2011 | Nylander et al. |
| 2011/0200022 | A1 | 8/2011 | Annamalai |
| 2011/0280154 | A1 | 11/2011 | Silverstrim et al. |
| 2012/0258711 | A1* | 10/2012 | Bao et al. ............... 455/434 |
| 2013/0165079 | A1* | 6/2013 | Gogic ..................... 455/411 |

FOREIGN PATENT DOCUMENTS

| | | | |
|---|---|---|---|
| CN | 101175333 | A | 5/2008 |
| EP | 2286569 | | 2/2011 |
| GB | 2425291 | A | 10/2006 |
| GB | 2425921 | A | 11/2006 |
| JP | 20010264096 | | 9/2001 |
| JP | 2003022303 | | 1/2003 |
| JP | 2003088521 | | 10/2003 |
| JP | 2004112324 | | 4/2004 |
| JP | 2005073147 | | 3/2005 |
| JP | 2005215849 | | 8/2005 |
| JP | 20060674143 | | 3/2006 |
| JP | 2008048055 | | 2/2008 |
| WO | 02-14987 | A2 | 2/2002 |
| WO | 2005076964 | A2 | 8/2005 |
| WO | 2007015067 | A2 | 2/2007 |
| WO | 2007040449 | A1 | 4/2007 |
| WO | 2008047039 | A1 | 4/2008 |

OTHER PUBLICATIONS

Office Action dated Mar. 30, 2015 for U.S. Appl. No. 14/219,543, 81 Pages.
Office Action dated Mar. 26, 2015 for U.S. Appl. No. 14/472,012, 62 Pages.
Office Action dated May 18, 2015 for U.S. Appl. No. 14/567,839, 59 Pages.
Chinese Office Action dated Jun. 30, 2015 for Chinese Patent Application No. 200980117188.5, 7 pages.
Office Action dated Aug. 19, 2015 for U.S. Appl. No. 12/465,585, 42 pages.
Office Action dated Aug. 20, 2015 for U.S. Appl. No. 14/219,543, 43 pages.
Office Action dated Sep. 11, 2015 for U.S. Appl. No. 14/286,414, 28 pages.
Office Action dated Sep. 24, 2015 for U.S. Appl. No. 14/472,012, 40 pages.
Office Action dated Nov. 1, 2012 for U.S. Appl. No. 12/276,058, 59 pages.
Office Action dated Nov. 5, 2012 for U.S. Appl. No. 12/484,072, 52 pages.
Office Action dated Nov. 20, 2012 for U.S. Appl. No. 12/275,878, 28 pages.
Japanese Office Action mailed Sep. 13, 2012 for Japanese Patent Application No. 2011-509669, 10 pages.
Canadian Office Action mailed Oct. 30, 2012 for Canadian Patent Application No. 2,722,324, 3 pages.
Japanese Office Action mailed Sep. 13, 2012 for Japanese Patent Application No. 2011-509675, 4 pages.
Office Action dated Dec. 3, 2012 for U.S. Appl. No. 12/275,416, 33 pages.
Office Action dated Jan. 17, 2013 for U.S. Appl. No. 13/554,710, 42 pages.
Final Office Action dated Feb. 15, 2013 for U.S. Appl. No. 12/579,957.
Office Action dated Feb. 26, 2013 for U.S. Appl. No. 12/276,120, 59 pages.
Chinese Office Action for Chinese Application No. 200980117263.8 dated Feb. 16, 2013, 7 pages.
Chinese Office Action for Chinese Application No. 200980117188.5 dated Jan. 31, 2013, 11 pages.
Final Office Action dated Mar. 14, 2013 for U.S. Appl. No. 12/484,072, 34 pages.
Office Action dated Apr. 23, 2013 for U.S. Appl. No. 12/175,293, 41 pages.
Canadian Office Action mailed Mar. 26, 2013 for Canadian Patent Application No. 2,722,324, 4 pages.
Office Action dated Jul. 15, 2013 for U.S. Appl. No. 13/554,710, 37 pages.
Office Action dated Aug. 13, 2013 for U.S. Appl. No. 12/276,120, 66 pages.
Office Action dated Aug. 12, 2013 for U.S. Appl. No. 12/275,416, 36 pages.
Office Action dated Sep. 9, 2013 for U.S. Appl. No. 12/465,585, 45 pages.
Office Action dated Oct. 2, 2013 for U.S. Appl. No. 12/275,878, 38 pages.
Office Action dated Oct. 3, 2013 for U.S. Appl. No. 13/892,923, 62 pages.
Office Action dated Oct. 22, 2013 for U.S. Appl. No. 13/898,910, 50 pages.
Office Action dated Oct. 3, 2013 for U.S. Appl. No. 13/934,644, 17 pages.
Chinese Office Action dated Oct. 24, 2013 for Chinese Patent Application No. 200980117263.8, 13 pages.
Chinese Office Action dated Oct. 21, 2013 for Chinese Patent Application No. 200980117188.5, 11 pages.
Japanese Office Action dated Oct. 3, 2013 for Japanese Patent Application No. 2011-509669, 15 pages.
Office Action dated Dec. 12, 2013 for U.S. Appl. No. 12/276,120, 78 pages.
Notice of Allowance dated Feb. 13, 2014 for U.S. Appl. No. 12/275,878, 34 pages.
Hasan, Mohammad Masud; Huang, Xiadong; Jue, Jason P.; "Survivable Wireless Access Network Design with Dual-homing Capabilities"; IEEE Global Telecommunications Conference, Nov. 27-Dec. 1, 2006, 5 pgs.
Japanese Office Action dated Jan. 16, 2014 for Japanese Patent Application No. 2013-026198, 8 pages.
Office Action dated Mar. 26, 2014 for U.S. Appl. No. 12/465,585, 44 pages.
Office Action dated Mar. 24, 2014 for U.S. Appl. No. 13/934,644, 50 pages.
Notice of Allowance dated Apr. 4, 2014 for U.S. Appl. No. 14/090,802, 63 pages.
Office Action dated Mar. 24, 2014 for U.S. Appl. No. 13/671,191, 63 pages.
Office Action dated Jun. 9, 2014 for U.S. Appl. No. 12/276,120, 92 Pages.
Office Action dated Jun. 11, 2014 for U.S. Appl. No. 13/675,150, 68 Pages.
Chinese Office Action dated Jun. 19, 2014 for Chinese Patent Application No. 200980117188.5, 5 Pages.
Canadian Office Action dated May 13, 2014 for Canadian Patent Application 2,722,367, 5 Pages.
Office Action dated Jun. 10, 2014 for U.S. Appl. No. 14/253,553, 16 pages.
Office Action dated Sep. 9, 2014 for U.S. Appl. No. 12/276,120, 93 pages.
Office Action dated Nov. 6, 2014 for U.S. Appl. No. 12/465,585, 43 pages.
Chinese Office Action dated Dec. 22, 2014 for Chinese Patent Application No. 200980117188.5, 4 Pages.
Office Action dated Dec. 23, 2014 for U.S. Appl. No. 13/917,153, 90 pages.
Office Action dated Feb. 4, 2015 for U.S. Appl. No. 13/949,983, 90 pages.
European Office Action dated Feb. 2, 2015 for European Patent Application No. 09747521.4, 4 pages.

(56) References Cited

OTHER PUBLICATIONS

Office Action dated Feb. 19, 2015 for U.S. Appl. No. 12/276,120, 90 pages.
Office Action dated Mar. 13, 2015 for U.S. Appl. No. 12/465,585, 39 Pages.
Office Action dated Jul. 22, 2015 for U.S. Appl. No. 12/276,120, 120 pages.
Office Action dated Jun. 29, 2015 for U.S. Appl. No. 13/949,983, 39 pages.
Office Action dated Jul. 13, 2015 for U.S. Appl. No. 14/520,274, 69 pages.
Canadian Office Action dated Apr. 7, 2015 for Canadian Patent Application No. 2,722,367, 6 Pages.
International Search Report and Written Opinion dated Oct. 27, 2009 for PCT Application Serial No. PCT/US2009/043861, 14 Pages.
International Search Report and Written Opinion mailed Feb. 23, 2010, for PCT Application No. PCT/US2009/043846, 13 pages.
Office Action dated Dec. 31, 2009 for U.S. Appl. No. 11/457,129, 16 pages.
Office Action dated Apr. 17, 2009 for U.S. Appl. No. 11/276,269, 15 pages.
Office Action dated Nov. 4, 2008 for U.S. Appl. No. 11/276,269, 15 pages.
Office Action dated Jun. 17, 2010 for U.S. Appl. No. 11/457,129, 15 pages.
Kaul, "Verizon's $250 femto box—A deliberate ploy behind the aggressive pricing?" Posted Tue, Jan. 20, 2009 13:19:46 EST; http://www.abiresearch.com/research_blog/569; © 2009 Allied Business Intelligence, Inc.
Office Action dated Mar. 29, 2011 for U.S. Appl. No. 12/276,002, 37 pages.
Office Action dated Apr. 13, 2011 for U.S. Appl. No. 12/276,058, 40 pages.
Office Action dated Apr. 19, 2011 for U.S. Appl. No. 12/276,238, 22 pages.
Office Action dated May 5, 2011 for U.S. Appl. No. 12/275,015, 32 pages.
Office Action dated Jun. 14, 2011 for U.S. Appl. No. 12/275,878, 35 pages.
Office Action dated Jun. 22, 2011 for U.S. Appl. No. 12/484,072, 38 pages.
Office Action dated Jul. 7, 2011 for U.S. Appl. No. 12/276,257, 24 pages.
Office Action dated Jun. 28, 2011 for U.S. Appl. No. 12/275,925, 18 pages.
Office Action dated Jun. 8, 2011 for U.S. Appl. No. 12/484,026, 30 pages.
Office Action dated Aug. 18, 2011 for U.S. Appl. No. 12/275,416, 39 pages.
Office Action dated Sep. 14, 2011 for U.S. Appl. No. 12/276,002, 35 pages.
Office Action dated Oct. 5, 2011 for U.S. Appl. No. 12/276,058, 37 pages.
Office Action dated Oct. 6, 2011 for U.S. Appl. No. 12/465,483, 50 pages.
Office Action dated Oct. 4, 2011 for U.S. Appl. No. 12/484,135, 44 pages.
Office Action dated Jul. 21, 2011 for U.S. Appl. No. 12/175,293, 30 pages.
Office Action dated Oct. 24, 2011 for U.S. Appl. No. 12/275,925, 14 pages.
Office Action dated Nov. 30, 2011 for U.S. Appl. No. 12/275,878, 38 pages.
Office Action dated Dec. 1, 2011 for U.S. Appl. No. 12/275,996, 44 pages.
Office Action dated Oct. 25, 2011 for U.S. Appl. No. 12/465,580, 39 pages.
Office Action dated Nov. 8, 2011 for U.S. Appl. No. 12/465,468, 50 pages.
Office Action dated Jan. 5, 2012 for U.S. Appl. No. 12/465,585, 43 pages.
Office Action dated Dec. 28, 2011 for U.S. Appl. No. 12/175,293, 38 pages.
Office Action dated Nov. 21, 2011 for U.S. Appl. No. 12/484,026, 37 pages.
Office Action dated Dec. 14, 2011 for U.S. Appl. No. 12/484,072, 44 pages.
Office Action dated Nov. 1, 2011 for U.S. Appl. No. 12/816,087, 33 pages.
Office Action dated Mar. 5, 2012 for U.S. Appl. No. 12/465,598, 55 pages.
Office Action dated May 8, 2012 for U.S. Appl. No. 11/457,129, 38 pages.
Office Action dated Mar. 19, 2012 for U.S. Appl. No. 12/276,120, 68 pages.
Office Action dated Mar. 30, 2012 for U.S. Appl. No. 12/484,026, 30 pages.
Notice of Allowance dated Apr. 3, 2012 for U.S. Appl. No. 12/275,996, 38 pages.
Office Action dated Apr. 10, 2012 for U.S. Appl. No. 12/275,416, 32 pages.
Office Action dated Apr. 10, 2012 for U.S. Appl. No. 12/484,135, 45 pages.
Notice of Allowance dated Apr. 25, 2012 for U.S. Appl. No. 12/465,468, 35 pages.
Office Action dated Jul. 16, 2012 for U.S. Appl. No. 12/275,878, 37 pages.
Office Action dated Jul. 10, 2012 for U.S. Appl. No. 12/465,585, 32 pages.
Office Action dated Apr. 13, 2012 for U.S. Appl. No. 13/316,106, 35 pages.
Office Action dated Sep. 5, 2012 for U.S. Appl. No. 12/276,120, 49 pages.
Office Action dated Aug. 16, 2012 for U.S. Appl. No. 12/465,598, 31 pages.
Office Action dated Sep. 6, 2012 for U.S. Appl. No. 12/579,957, 51 pages.
Office Action dated Sep. 10, 2012 for U.S. Appl. No. 12/276,002, 54 pages.
Office Action dated Oct. 2, 2012 for U.S. Appl. No. 12/484,026, 29 pages.
Office Action dated Oct. 11, 2012 for U.S. Appl. No. 13/487,794, 45 pages.
Office Action dated Oct. 9, 2012 for U.S. Appl. No. 13/298,924, 51 pages.
Office Action dated Oct. 30, 2015 for U.S. Appl. No. 13/949,983, 19 pages.
Final Office Action dated Jan. 21, 2016 for U.S. Appl. No. 12/276,120, 108 pages.
Final Office Action dated Jan. 21, 2016 for U.S. Appl. No. 12/465,585, 28 pages.

* cited by examiner

EXCHANGE OF ACCESS CONTROL LISTS TO MANAGE FEMTO CELL COVERAGE

CROSS-REFERENCE TO RELATED APPLICATION

This application is a continuation of, and claims priority to each of, U.S. patent application Ser. No. 13/675,150(now U.S. Pat. No. 9,019, 819), entitled "EXCHANGE OF ACCESS CONTROL LISTS TO MANAGE FEMTO CELL COVERAGE" and filed on Nov. 13, 2012, which is a continuation of U.S. patent application Ser. No. 13/316,106 (now U.S. Pat. No. 8,331, 228), entitled "EXCHANGE OF ACCESS CONTROL LISTS TO MANAGE FEMTO CELL COVERAGE" and filed on Dec. 9, 2011, which is a continuation of U.S. patent application Ser. No. 12/276,257 (now U.S. Pat. No. 8,094, 551), entitled "EXCHANGE OF ACCESS CONTROL LISTS TO MANAGE FEMTO CELL COVERAGE" and filed on Nov. 21, 2008, and each of which applications claim the benefit of U.S. Provisional Patent Application No. 61/052, 813, entitled "MANAGEMENT OF ACCESS TO FEMTO CELL COVERAGE" and filed on May 13, 2008. The entireties of each of these applications and corresponding patents are incorporated by reference herein.

TECHNICAL FIELD

The subject application relates to wireless communications and, more particularly, to management of access to femto cell coverage by a subscriber and subscriber stations.

BACKGROUND

Femto cells—building-based wireless access points interfaced with a wired broadband network—are generally deployed to improve indoor wireless coverage provided by a wireless network operator. Femto cells typically operate in licensed portions of the electromagnetic spectrum, and generally offer plug-and-play installation; e.g., automatic configuration of femto access point. Improved indoor coverage includes stronger signal and improved reception (e.g., voice or sound), ease of session or call initiation and session or call retention as well. Coverage of a femto cell, or femto AP, is intended to be confined within the bounds of an indoor compound, in order to mitigate interference among mobile stations covered by a macro cell and terminals covered by the femto AP. Additionally, confined coverage can reduce crosstalk among terminals serviced by disparate, neighboring femto cells as well.

Coverage improvements via femto cells can also mitigate customer attrition as long as a favorable subscriber perception regarding voice coverage and other data services with substantive delay sensitivity is attained. A positive customer experience can depend on adequate access management to femto cell service. Such adequate access management can include configuration procedures of a provisioned femto cell access point deployed in a coverage area. Thus, cumbersome configuration procedures that (i) involve interaction with customer service representatives; (ii) fail to provide versatility and autonomy, with substantially low complexity; or (iii) fail to be directed to a broad spectrum of consumers with various disparate degrees of technological savvy, can hinder femto cell service adoption and thus prevent pervasive dissemination of utilization of home-based and business-based femto access points and exploitation of operational efficiencies thereof.

DETAILED DESCRIPTION

Figure 1:
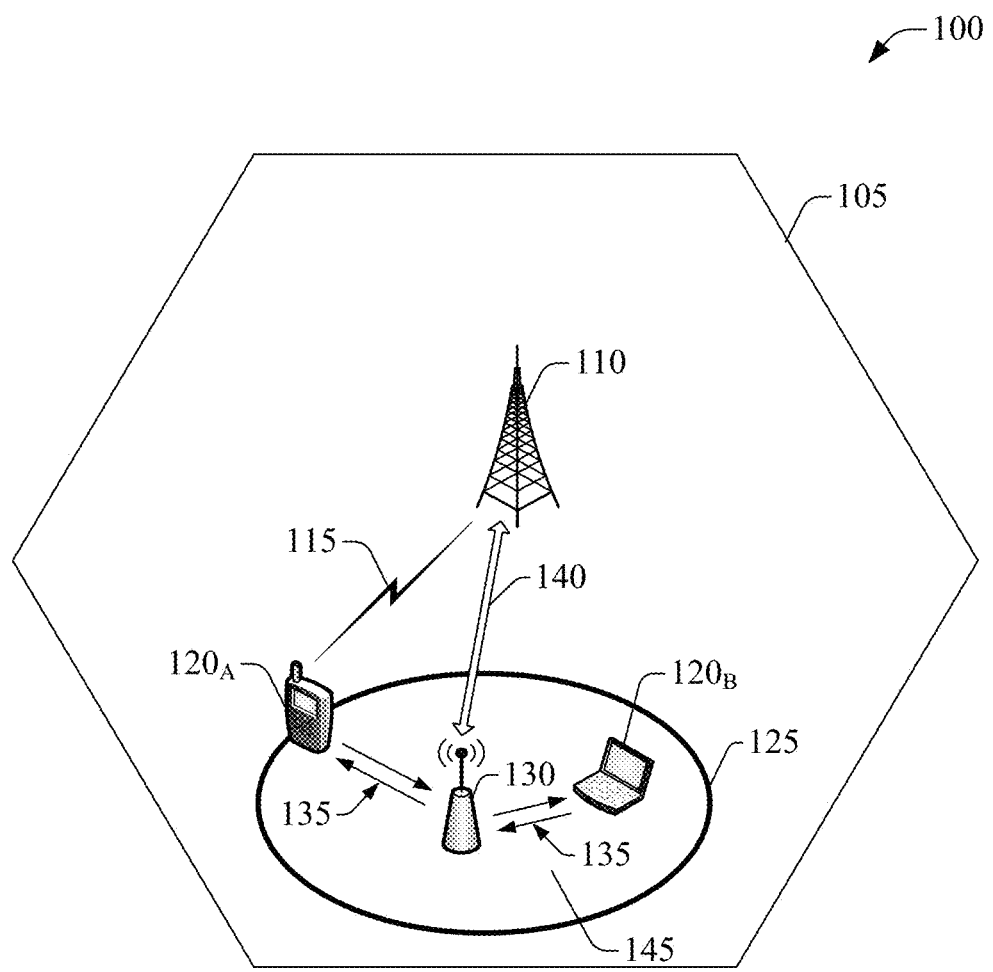
FIG. 1 a schematic deployment of a macro cell and a femto cell for wireless coverage in accordance with aspects described herein.

The subject application is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the terms "component," "system," "platform," and the like are intended to refer to a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers. Also, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal).

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

Moreover, terms like "user equipment," "mobile station," "mobile," subscriber station," "access terminal," "terminal," "handset," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "access point," "base station," "Node B," "evolved Node B," "home Node B (HNB)," and the like, are utilized interchangeably in the subject application, and refer to a wireless network component or appliance that serves and receives data, control, voice, video, sound, gaming, or substantially any data-stream or signaling-stream from a set of subscriber stations. Data and signaling streams can be packetized or frame-based flows. Furthermore, the terms "access control list" and "access list" are also utilized interchangeably and intend to covey the same meaning unless otherwise explicitly noted.

Furthermore, the terms "user," "subscriber," "customer," "consumer," "prosumer," "agent," and the like are employed interchangeably throughout the subject specification, unless context warrants particular distinction(s) among the terms. It should be appreciated that such terms can refer to human entities or automated components supported through artificial intelligence (e.g., a capacity to make inference based on complex mathematical formalisms) which can provide simulated vision, sound recognition and so forth. As utilized herein, the term "prosumer" indicate the following contractions: professional-consumer and producer-consumer.

The subject application provides system(s) and method(s) to manage access to femto cell service through access control list(s), e.g., white list(s) or black list(s). Such access control list(s) can be configured through various apparatuses and in various modes, e.g., interactively or automatically, which facilitates access management of access to femto cell coverage. White list(s) includes a set of subscriber station(s) identifier numbers, codes or tokens, and can also include additional fields that can contain information respectively associated with communication devices to facilitate femto cell access management based at least in part on desired complexity; for instance, an additional field in a white list can be a logic parameter that determines whether an associated identifier is available for dissemination across disparate white lists. Values of attribute fields that determine white list(s), black list(s), or white list profile(s) can be generated through various sources. Access lists exchange among subscribers that posses provisioned femto access points and elect to share access lists also is provided. Transference of access list(s) among subscribers is secured and based at least in part on subscriber privacy policy. Subscribers can be prompted to opt in access list sharing, or to update privacy policies to allow reciprocate sharing and update privacy settings. Based at least in part on association criteria, component identifies femto access points for a subscriber to access lists with. Various example aspects such as white list(s) management, maintenance and dissemination; automatic population or pre-configuration; and inclusion of wireless device(s) or subscriber(s) are also provided.

Referring to the drawings, FIG. 1 illustrates a schematic wireless environment (e.g., a network) 100 in which a femto cell can exploits various aspects described in the subject specification. In wireless environment 100, area 105 represents a coverage macro cell which is served by base station 110. Macro coverage is generally intended for outdoors locations for servicing mobile wireless devices, like UE 120$_A$, and such coverage is achieved via a wireless link 115. In an aspect, UE 120 can be a 3rd Generation Partnership Project (3GPP) Universal Mobile Telecommunication System (UMTS) mobile phone.

Within macro coverage cell 105, a femto cell 145, served by a femto access point 130, can be deployed. A femto cell typically covers an area 125 that is determined, at least in part, by transmission power allocated to femto AP 130, path loss, shadowing, and so forth. Coverage area typically is spanned by a coverage radius that ranges from 20 to 50 meters. Confined coverage area 145 is generally associated with an indoors area, or a building, which can span about 5000 sq. ft. Generally, femto AP 130 typically services a few (e.g., 1-9) wireless devices (e.g., subscriber station 120$_B$) within confined coverage area 145. In an aspect, femto AP 130 can integrate seamlessly with substantially any packet switched (PS)-based and circuit switched (CS)-based network; for instance, femto AP 130 can integrate into an existing 3GPP Core via conventional interfaces like Iu-CS, Iu-PS, Gi, Gn. In another aspect, femto AP 130 can exploit high-speed downlink packet access in order to accomplish substantive bitrates. In yet another aspect, femto AP 130 has a LAC (location area code) and RAC (routing area code) that is different than the underlying macro network. These LAC and RAC are used to identify subscriber station location for a variety of reasons, most notably to direct incoming voice and data traffic to appropriate paging transmitters.

As a subscriber station, e.g., UE 120$_A$, leaves macro coverage (e.g., cell 105) and enters femto coverage (e.g., area 125), as illustrated in environment 100, UE 120$_A$ attempts to attach to the femto AP 130 through transmission and reception of attachment signaling, effected via a FL/RL 135; in an aspect, the attachment signaling can include a Location Area Update (LAU) and/or Routing Area Update (RAU). Attachment attempts are a part of procedures to ensure mobility, so voice calls and sessions can continue even after a macro-to-femto transition or vice versa. It is to be noted that UE 120 can be employed seamlessly after either of the foregoing transitions. Femto networks are also designed to serve stationary or slow-moving traffic with reduced signaling loads compared to macro networks. A femto service provider (e.g., an entity that commercializes, deploys, and/or utilizes femto access point 130) is therefore inclined to minimize unnecessary LAU/RAU signaling activity at substantially any opportunity to do so, and through substantially any available means. It is to be noted that substantially any mitigation of unnecessary attachment signaling/control is advantageous for femto cell operation. Conversely, if not successful, UE 120 is generally commanded (through a variety of communication means) to select another LAC/RAC or enter "emergency calls only" mode. It is to be appreciated that this attempt and handling process can occupy significant UE battery, and femto AP capacity and signaling resources as well.

When an attachment attempt is successful, UE 120 is allowed on femto cell 125 and incoming voice and data traffic are paged and routed to the subscriber through the femto AP 130. It is to be noted also that data traffic is typically routed through a backhaul broadband wired network backbone 140 (e.g., optical fiber backbone, twisted-pair line, T1/E1 phone line, digital subscriber line (DSL), or coaxial cable). To this end, femto AP 130 is connected to the broadband backhaul network backbone 140 via a broadband modem (not shown).

It is to be noted that as a femto AP 130 generally relies on a backhaul network backbone 140 for routing and paging, and for packet communication, substantially any quality of service (QoS) can be handled for heterogeneous packetized traffic. Namely, packet flows established for wireless devices (like terminals 120$_A$ and 120$_B$) served by femto AP 130, and for devices served through the backhaul network pipe 140. It is to be noted that to ensure a positive subscriber experience, or perception, it is important for femto AP 130 to maintain a high level of throughput for traffic (e.g., voice and data) utilized on a mobile device for one or more subscribers while in the presence of external, additional packetized, or broadband, traffic associated with applications (web browsing, data transfer (e.g., content upload), and the like) executed in devices within the femto coverage area (e.g., either area 125 or area 145).

In the subject application, described means to authorize, permanently or temporarily, or deny or revoke access to specific subscribers, or subscriber station(s), comprise what is herein termed as an access control list(s) (e.g., white list(s) or black list(s))—an instrument for management of access to femto cell coverage. White list(s) can also have an associated white list profile as described hereinafter. In an aspect, access list(s) (e.g., white list(s) or black list(s)) and white list profile(s) can be relational database tables that include a set of one or more fields for each attribute in the tables. It is noted, however, that other table models (e.g., hierarchical, object oriented) can be employed to define access list(s) and white list profile(s). Various attributes can be defined for access list(s); for example, mobile device identifier attribute, which uniquely identifies the mobile device; public or private attribute, which can be an election flag (e.g., opt-in/opt-out flag) that establishes whether mobile device identifier can be shared among disparate access list(s); device technology attribute(s), which provides information on operation capabilities of mobile device(s) includes within white list(s); and so forth. As an illustration, a device identifier attribute in access list(s) (e.g., white list(s) or black list(s)) can support up to N fields (N a positive integer; e.g., N=50) for unique mobile phone numbers (e.g., mobile subscriber number integrated digital services network numbers (MSIDSNs), international mobile subscriber identity(ies) (IMSIs), or any suitable codes (e.g., electronic serial numbers (ESNs), subscriber identity module (SIM) credentials) or tokens that identify a mobile device. Number N of fields can be determined, or configured, by a service operator based at least in part on technical aspects (like network resources, quality of service consideration, macro area of coverage (e.g., metropolitan statistical area (MSA), or rural service area (RSA)) and commercial aspects (such as promotional considerations, mitigation of customer attrition, gains in market share, etc.) of provision of coverage. As an example, N can be subscriber dependent or femto AP dependent; e.g., premium subscriber that consumes substantive volume of data, like prosumers, can have larger N than subscribers that primarily consume voice. It should be appreciated that the magnitude of N can also be determined dynamically, and augmented on a subscriber-need basis within bounds determined by network capacity.

In an aspect of the subject application, black list(s) include a single attribute field which uniquely identifies a mobile device, the identified device is denied femto access service. It is noted that while a black list is a realization of an access list, and can be configured by a consumer according to aspects described herein, a black list can be employed as an administrative means to deny femto service under various criteria, e.g., lack of payment for service(s), unlawful utilization of a provisioned femto access point, and so forth. Mobile device identified in a black list can operate in "emergency call" mode only.

With respect to white list profile(s), one or more attributes thereon can be associated with a white list. The one or more attributes establish logic for utilization of femto coverage by mobile stations associated identified through a mobile device identifier attribute in a white list. White list profile(s) attribute(s) and values thereof can establish access privileges to femto coverage. In an aspect, white list profile(s) attribute(s) are related to field values, or records, in white list(s) via primary keys (e.g., a unique mobile device identifier) of the white list(s). As an example, for a mobile station catalogued via a respective identifier numeric attribute (e.g., MSISDN, IMSI) in a white list (e.g., white list(s) 254), service attribute(s) in the white list profile can determine at least one of the following. (1) A category of service (e.g., voice only, data only, voice and data), or a class of service, which determines access to specific applications or services such as scheduler, calendar(s), news streaming, authoring tools, gaming, video and music, etc., that is allowed for the mobile station; (2) quality of service configuration, or customization, for mobile device access to femto coverage, such as guaranteed QoS (e.g., guaranteed packet rate, or guaranteed block error rate) rather than best effort delivery; (3) time span of allowed service for the mobile station such as (i) temporary full access to provisioned femto service(s), e.g., full access for a specific time interval such as days (e.g., a relative is on vacation on a house with a provisioned femto AP) or hours (babysitter is on duty), or (ii) temporary restricted access, which can determine access to selected services only within a window of time in a day (voice and data allowed from 9:00 a-6:00 p, or voice allowed after 9:00 p which can facilitate billing schemes already established by an operator/service provider); (4) telecommunication technology allowed for use in a femto cell when the mobile station supports operation through multiple technologies (e.g., GSM, 3GPP UMTS, 3GPP LTE Advanced . . . ); (5) billing aspects for an identified mobile device; and so on.

In an illustrative aspect of the application, access list(s) (e.g., white list(s) 232 or black list(s)) and white list profile(s), or any set of numbers, codes or tokens thereon that comprise a set of mobile phones or mobile devices approved for coverage by femto access point (e.g., femto AP 130), can be portable through accounts or billing groups associated with a set of subscribers to a service operator that administers femto AP 130, or a macro network.

Figure 2:
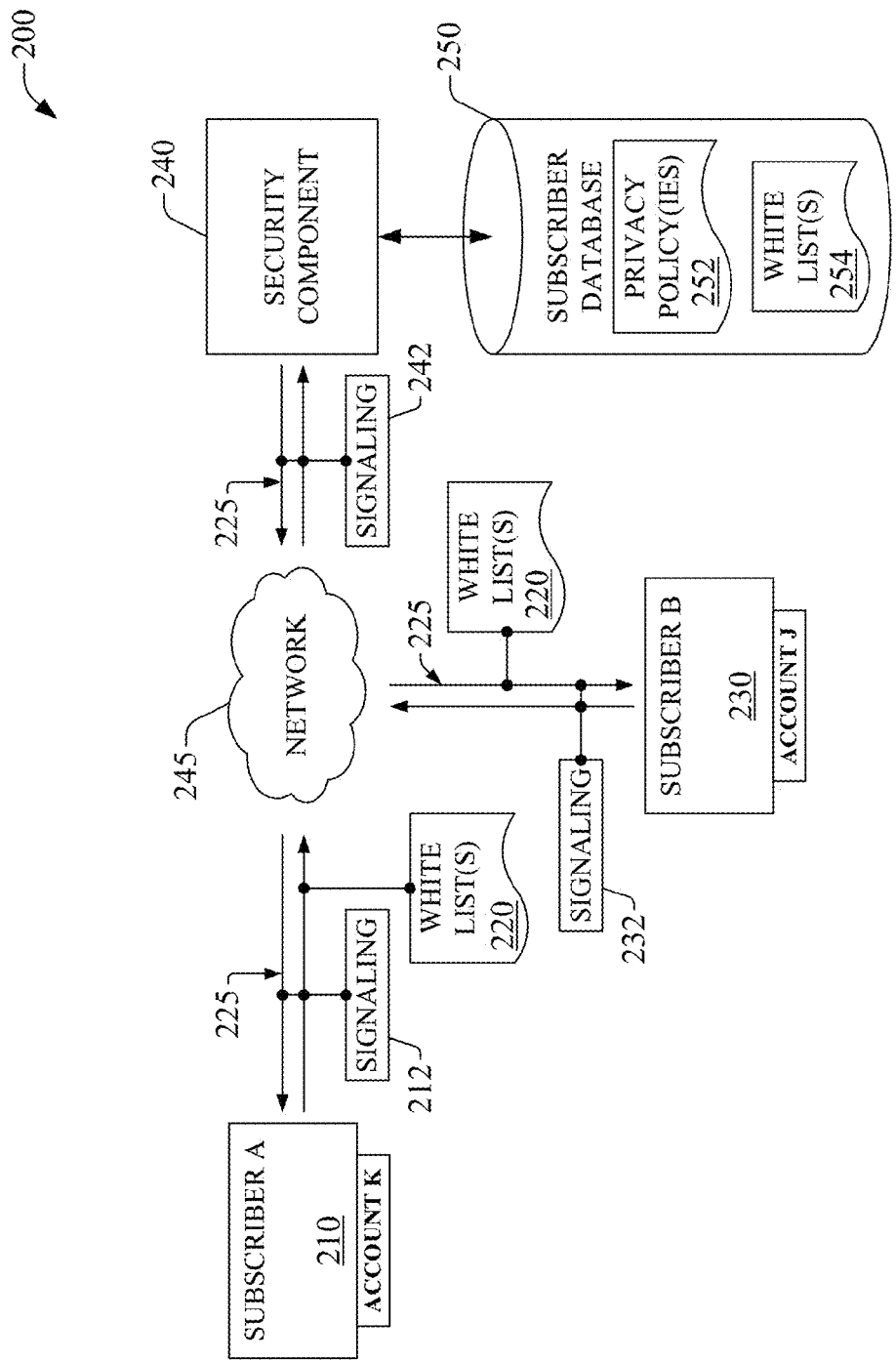
FIG. 2 is a block diagram of an example system to share access control list(s), e.g., white list(s), in accordance with aspects described herein.

FIG. 2 is a block diagram of an example system 200 to share access control list(s), e.g., white list(s) 220, among subscribers of a wireless network service in order to provide straightforward access configuration to, and activation of, a femto cell (e.g., femto AP 130) among femto cell subscribers. Subscribers can belong to disparate or same service accounts with either a macro service provider or femto provider, or both. For example, subscribers that share white list(s) 220 can pertain to a group or family associated with a single service account. In example system 200, subscriber A 210 who belongs to account K conveys white list(s) 220 over network 245, via a wired or wireless link 225, to subscriber B 230 who belongs to account J. Subscriber A 210 can hide or eliminate specific mobile device identifier attribute fields, e.g., subscriber station numbers, from white list(s) 220 that is granted to, or shared with, other subscribers. In an aspect, security component 240 can facilitate edition of white list(s) 220 based at least in part on privacy policy(ies) for dissemination of white list(s) associated with a subscriber that shares a white list. It should be appreciated that the granting of subscriber station numbers (e.g., MSISDNs, IMSIs . . . ), codes or tokens can substantially reduce the amount of time to configure, or set up a white list, as opposed to manually re-entering multiple (e.g., up to 50 numbers, codes or tokens) across multiple femto cells.

As indicated above, security component 240, or authorization layer, can ensure that unauthorized mobile subscriber numbers (e.g., MSISDNs, IMSIs . . . ), codes or tokens, are not provided when not approved by end users. In an aspect, security component 240 can generate election flags that reflect whether a mobile station can be added to a white list that is disseminated to subscribers other than (i) an originator subscriber, e.g., subscriber that is the source of the white list, or access list, or (ii) subscribers linked to a telecommunication service account owned by the originator subscriber. Such election flags can be retained in privacy policy(ies) 252. It should be appreciated that election flags can originate at least in part in privacy attribute field(s) in a white list that is shared; the privacy attribute field(s) entered by a subscriber that shares (e.g., submits) a white list. The aforementioned approval can be determined via privacy policy(ies) 252 associated with the end user, or subscriber linked to a mobile device, which can be stored in a subscriber database 250. The privacy policy can be configured/updated through various means like web-based interfaces, call center, text-message center, USSD messaging server, and so on; and can be received by security component 240 through signaling 212, retained in a subscriber database, and linked to a subscriber that establishes the privacy policy. Security component 240 ensures privacy integrity when white list(s) 220 are shared among subscribers of different accounts (e.g., J≠K). In an illustrative aspect, security component 440 can solicit or prompt, through signaling 242, subscribers outside a "white-list share" originating account (e.g., account K associated with subscriber A 210) to grant the authority for their subscriber station identifier number, code or token to be shared through white list(s) 220. Additionally, security component 240 can prompt subscriber(s) to configure privacy settings that determine, at least in part, privacy policy(ies) 252; for instance, security component can prompt a subscriber to elect to share access lists, e.g., white lists, or reciprocate a received access list (e.g., white list) upon reception of a white list form another subscriber. To the latter end, security component 240 can resort to various mechanisms to deliver signaling 242, which include, but are not limited to including, a short message service (SMS) communication, a multimedia message service (MMS) communication, instant message (IM) communication, email, voice mail, web pop up, and so on. Subscriber that receives a prompt can indicate a response through signaling as well, e.g., subscriber A 210 can convey signaling 212, while subscriber B 230 can convey signaling 232. Alternatively, or in addition, security component 240 can mitigate security mechanism(s) complexity through validation via subscriber account information such as election (e.g., opt-in/opt-out) flags (e.g., stored in subscriber database 250 within a subscriber's white list(s) 254 or privacy policy(ies) 252) in order to grant automatic access to white list(s) within groups or families underneath a single service account, without additional security verification.

It is noted that in example system 200, a processor (not shown) confer at least in part the functionality of the described components or network. Processor can be configured to execute, and can execute, code instructions stored in a memory (not shown), or a memory component thereon, to provide at least a portion of the described functionality. It should be appreciated that the processor can be a centralized element or be distributed among the above referenced components, or network.

Figure 3:
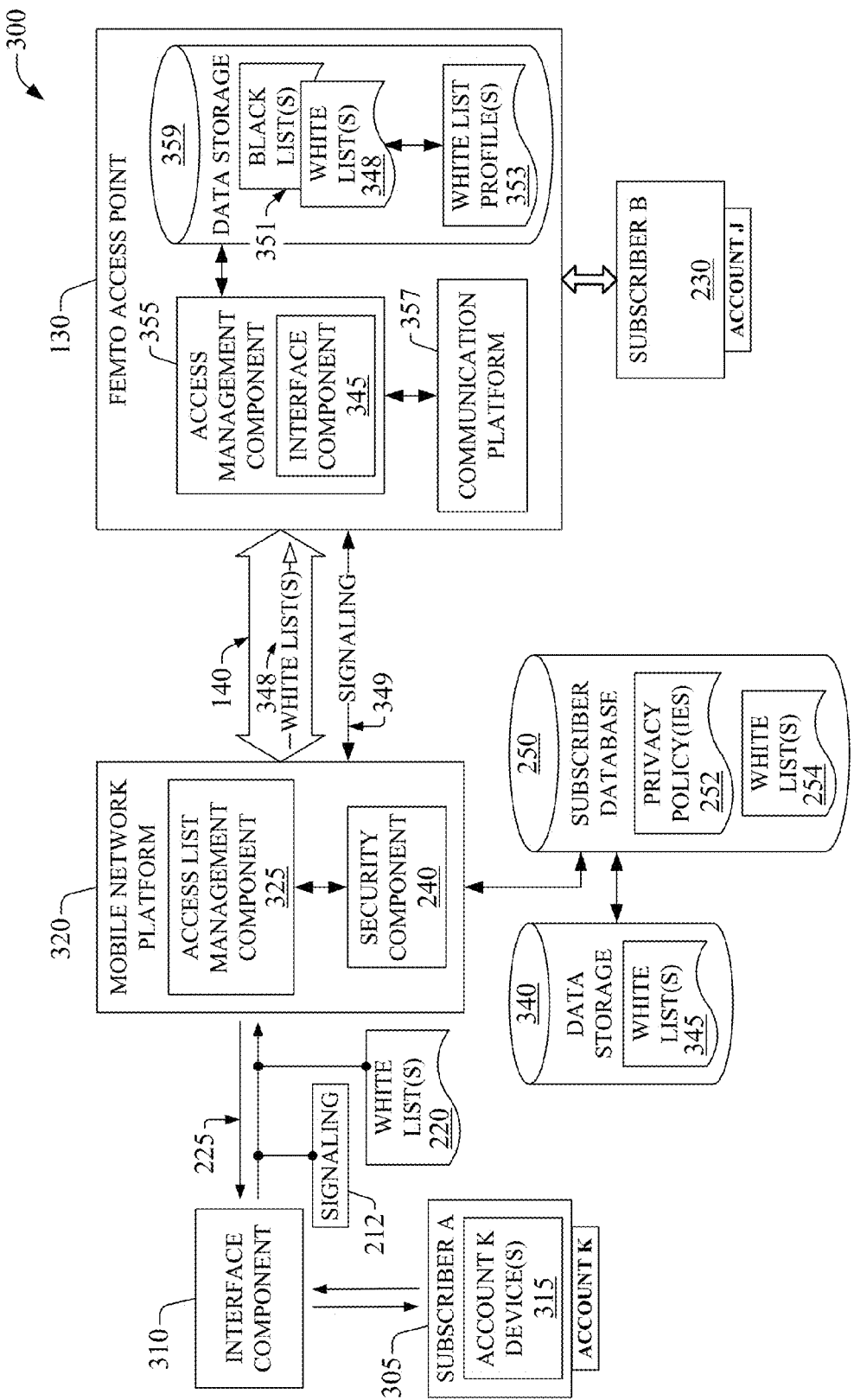
FIG. 3 is a block diagram of an example system that facilitates communication of a white list among subscribers in accordance with aspects described herein.

FIG. 3 is a block diagram of an example system 300 that facilitates communication of a white list among subscribers in accordance with aspects described herein. Subscriber A 305 utilizes interface component 310 to convey information, e.g., signaling 212, related to communication of white list(s) 220 to a subscriber B 230. It is noted that interface component 310 can be a part of one of various apparatuses such as a mobile device or a femto access point, or can reside at least in part in a service network (e.g., a non-mobile network platform such as a broadband internet service provider) or a mobile network platform 320. In example system 400, signaling 212 and white list(s) 220 are conveyed through a network link 225, which can be wired or wireless, to mobile network platform 320, wherein an access list management component 325, which is functionally coupled to security component 335, receives white list(s) 220. Access management component 325 also can convey, via backhaul link 140, a processed version of received white list(s) 220, e.g., white list 348, to an intended femto access point 130 provisioned to subscriber B 230; It should be appreciated that subscriber B 230 can either lease or own access femto access point 130. In an aspect, security component 240 processes received white list(s) 220 to ensure authorized identifier attribute fields in white list(s) 220 are delivered. Thus, processed white list 348 can include mobile device identifiers in accordance at least in part with privacy policy(ies) 252. Received white list(s) 220 and a copy of conveyed white list(s) 348 can be retained within data storage 340 in a memory element(s) white list(s) 345. In an aspect, data storage includes secure data storage which can be secured through security component. It is noted that data storage 340 can be a distributed entity, with portions thereof within a master database for mobile network platform 320 and portions within a femto network platform gateway node; it should be appreciated that subscriber database 250 also can be a portion of the master database for mobile network platform 320.

In femto access point 130, associated with, or provisioned to, subscriber B 230 who belongs to account J, communication platform 357 can receive shared white list(s) 348, and convey the received white list(s) 348 to access management component 355 which can administer femto coverage in accordance with access list(s) (e.g., white list(s) 348 or black list(s) 351) or white list profile(s) 353, and various additional aspects described hereinafter. In addition, access management component 345 can include an interface component 345, which can facilitate subscriber B 230 to convey signaling 349 in response to prompts conveyed by security component 335 and related to operation aspects of white list(s) dissemination. Received white list(s) 348 are retained in local data storage 359.

It is noted that in example system 300, a processor (not shown) confer at least in part the functionality of the described components or platforms. Processor can be configured to execute, and can execute, code instructions stored in a memory (not shown), or a memory component thereon, to provide at least a portion of the described functionality. It should be appreciated that the processor can be a centralized element or be distributed among the above referenced components or platforms.

Figure 4:
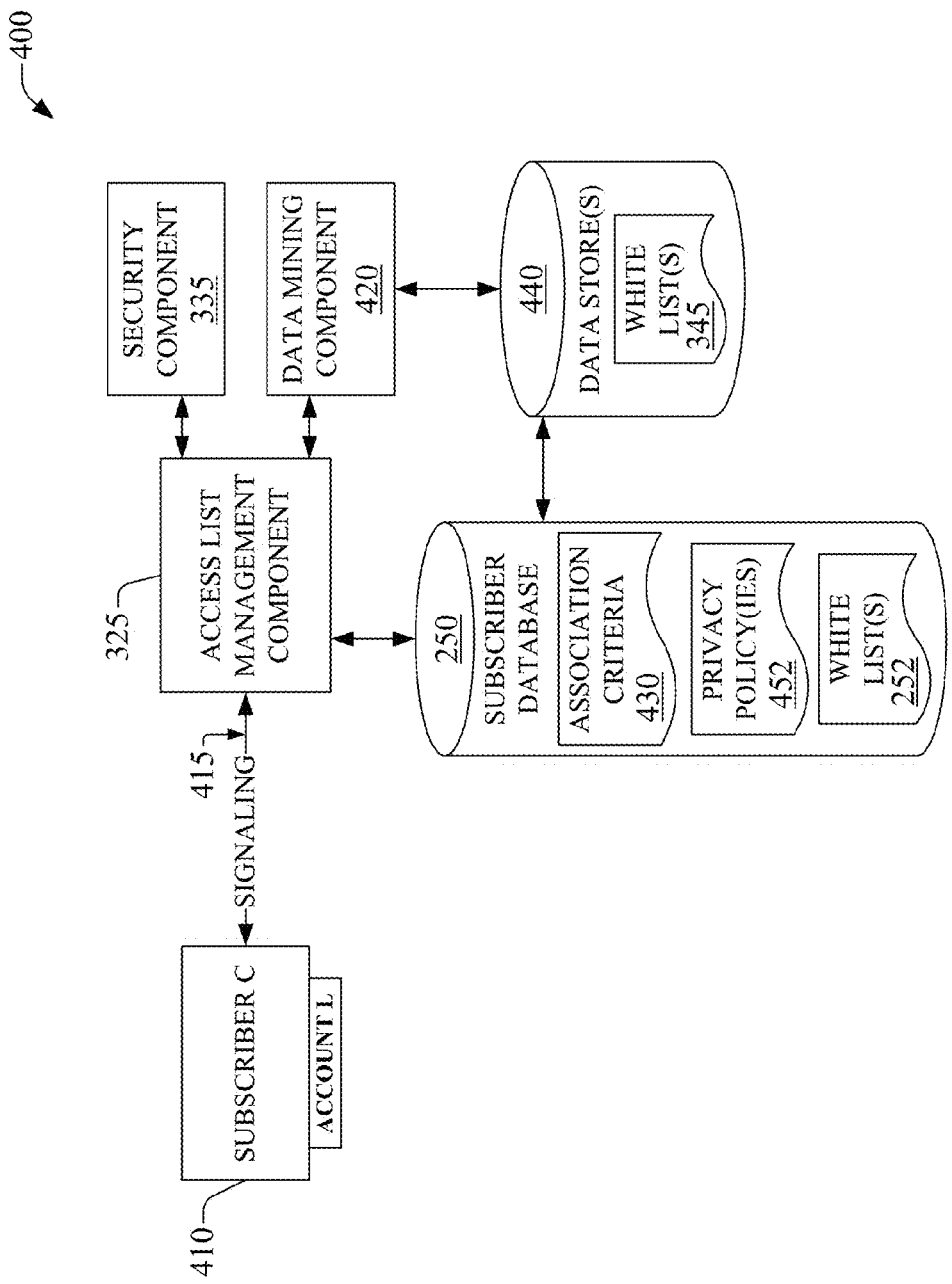
FIG. 4 is a block diagram of an example system that makes a subscriber aware of available femto access point in accordance with aspects described herein.

FIG. 4 is a block diagram of an example system 400 that makes a subscriber aware of available femto access point in accordance with aspects described herein. Access management component 325 can exploit data mining component 420 to extract and analyze data from various databases, e.g., data store(s) 440 and subscriber database 250. In an aspect, data store(s) 440 can be distributed among network platforms, mobile or otherwise, or femto access points. Access to data store(s) 440 and subscriber database 250 can take place in accordance with privacy policy(ies) 452 retained in subscriber database 250; security component 335 can enforce the privacy policy(ies) 452, which can include at least a portion of privacy settings of privacy policy(ies) 252. Data extraction can be based at least in part on a set of association criteria 430 that facilitates establishing relationship(s) among disparate femto access points in order to provide, e.g., notify, a subscriber, e.g., subscriber 410, with a set of one or more femto access points that satisfy, at least in part, association criteria 430. In an aspect, notification can proceed through SMS communication, MMS communication, email communication, voice communication (e.g., a call from a customer service center or call center), or the like. It is noted that based on the degree of compliance with association criteria 252, the relationship among disparate femto access points can be richer or more meaningful to subscriber 410. For example, an association criterion can be relative location of provisioned access points. In such case, data mining component 420 can identify a pattern of location(s) for a subscriber and determine femto access points located within a predetermined distance from locations in the pattern. It is to be noted that disparate locations within the pattern can be assigned disparate relevancy scores which can also affect subscriber response to a provided list of femto access points that meet location criteria. The residence of the subscriber has a substantive relevancy score, thus provisioned access points within a tolerance distance from the subscriber's residence can be of interest to the subscriber; e.g., the subscriber may be interested in sharing white list(s) with neighbors. The subscriber's workplace also can have a substantive relevancy score, thus femto access points nearby the subscriber's workplace can be of interest to the subscriber; e.g. a café that has a provisioned femto access point can become a preferred lunch-time location since femto coverage is available in such location at no cost to the subscriber, in turn the subscriber can consume at the café, contributing to its revenue. Other criteria can be generated such as location patterns associated with the subscriber and a family member of the subscriber: Locations within a pattern that reflects joint occupancy, namely a subscriber and a member of his/her service account jointly generate the pattern, also can provide for relevant femto access points. For example, a café in a skating rink that a subscriber regularly visits when taking his/her children for skating practice may have provisioned a femto access point; thus, exchange of white lists among the subscriber and an administrator of the café can be advantageous to the subscriber.

In an aspect criteria can be predetermined, provided either a subscriber or a service provider of femto service. In the latter case, femto service provider can generate disparate association criteria based upon subscriber intelligence such as subscriber segment (high-end consumer, low-end consumer), subscriber location or market in which subscriber operates, or the like. In another aspect, association criteria can be autonomously determined, based at least in part on subscriber response to identified femto access points: A "good" response, e.g., the subscriber seeks a white list exchange after a recommendation, can result in an increased validation score for the set of criteria; conversely, a "bad" response, e.g., the subscriber fails to pursue a recommendation can lead to adjustment of a set of criteria.

In accordance with an aspect of the subject application, data mining component 420 can utilize artificial intelligence (AI) methods to infer (e.g., reason and draw a conclusion based at least in part on a set of metrics, arguments, or known outcomes in controlled scenarios) patterns of call activity, relevancy of locations associated with the pattern, and/or other features suitable to autonomously identify a desirable femto access point for a subscriber. Artificial intelligence techniques typically can apply advanced mathematical algorithms—e.g., decision trees, neural networks, regression analysis, principal component analysis (PCA) for feature and pattern extraction, cluster analysis, genetic algorithm, and reinforced learning—to historic and/or current data associated with mobile devices served by a mobile network platform at the macro or femto level to facilitate rendering an inference(s) related to the mobile devices.

In particular, data mining component 420 can employ one of numerous methodologies for learning from data, e.g., machine learning methods, and then drawing inferences from the models so constructed, e.g., Hidden Markov Models (HMMs) and related prototypical dependency models. General probabilistic graphical models, such as Dempster-Shafer networks and Bayesian networks like those created by structure search using a Bayesian model score or approximation can also be utilized. In addition, linear classifiers, such as support vector machines (SVMs), non-linear classifiers like methods referred to as "neural network" methodologies, fuzzy logic methodologies can also be employed. Moreover, game theoretic models (e.g., game trees, game matrices, pure and mixed strategies, utility algorithms, Nash equilibria, evolutionary game theory, etc.) and other approaches that perform data fusion, etc., can be exploited in accordance with implementing various automated aspects described herein.

It is noted that in example system 400, a processor (not shown) confer at least in part the functionality of the described components. Processor can be configured to execute, and can execute, code instructions stored in a memory (not shown), or a memory component thereon, to provide at least a portion of the described functionality. It should be appreciated that the processor can be a centralized element or be distributed among the above referenced components.

Figure 5:
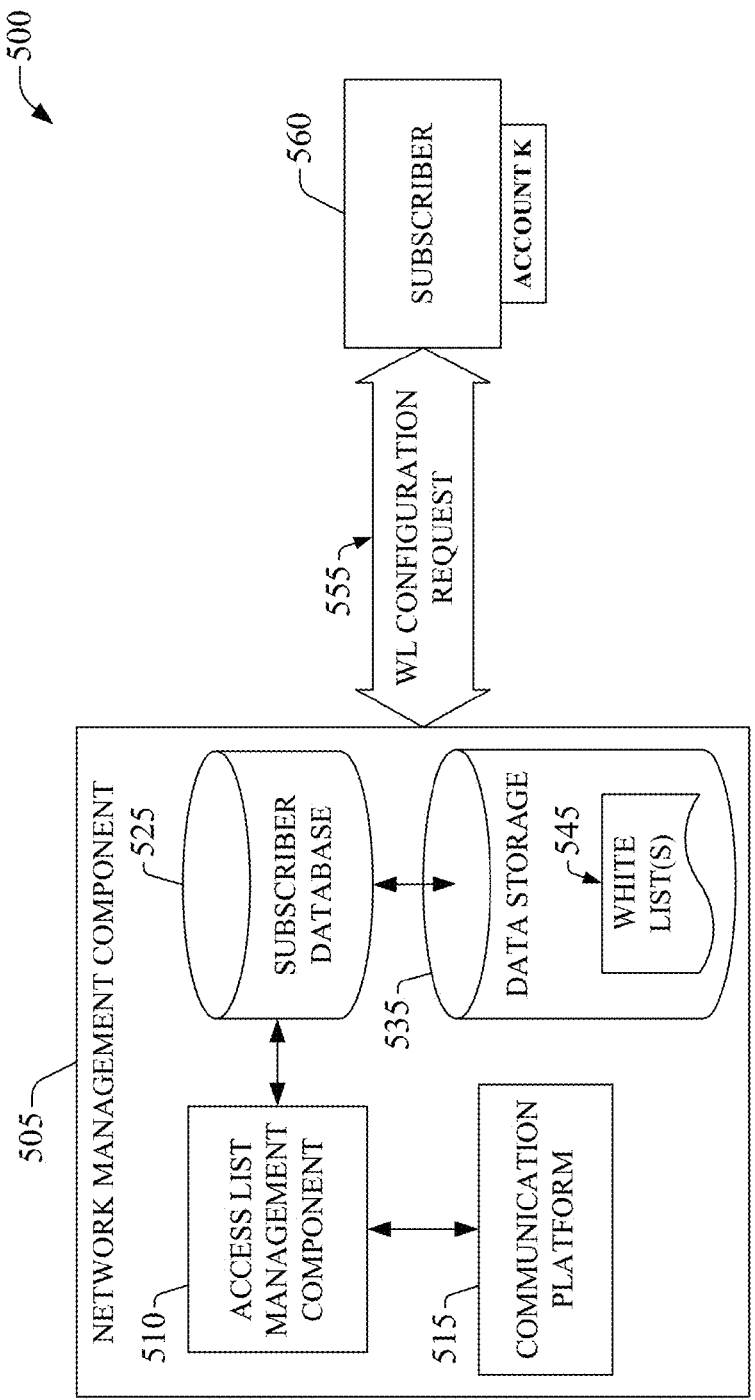
FIG. 5 is a block diagram of an example system that facilitates addition of subscriber(s)/subscriber station(s) to one or more white lists in accordance with aspects described in the subject specification.

FIG. 5 is a block diagram of an example system 500 that facilitates addition of subscriber(s)/subscriber station(s) to one or more white list(s) 545 in accordance with aspects described herein. In example system 500, a network management component 505 (e.g., a provisioning server) includes an access list management component 510 which is functionally coupled to a subscriber database 525, a data storage 535 and a communication platform 515; as discussed above, the data storage 535 can be a distributed entity. Access list management component 510 operates in the same manner as access list management component 325. It is noted that access list management component 510 can data-mine, e.g., through a data mining component 420 (not shown), subscriber database 525 and white list(s) 545, which resides in data storage 535, to drive addition of new subscribers who have opted in to be included in white list(s) to a white list to request reciprocal adding. In an aspect, once a subscriber 560 in account K is identified for reciprocal addition based at least in part on privacy policy(ies) (not shown), at a time the subscriber 560 configures his/her femto AP, a white list (WL) configuration request 555 is conveyed (e.g., via a wired or wireless link through communication platform 515) to the subscriber. Such WL configuration request 555, which can be embodied in signaling 415, can indicate that a disparate subscriber (e.g., subscriber B 230) has subscriber 560 white-listed and prompts subscriber 560 to include in his/her white list the disparate subscriber. An illustrative scenario is the following: User 1 adds User 2 to his/her white list. Once User 2 configures/activates his/her femto cell, a setup process (implemented, for example, through a web-based online GUI, or a GUI that is part of an interface component 345 in the provisioned femto access point) will prompt User 2 to add User 1. It is to be noted that access list management component 510 can exploit information in subscriber database 525 and data storage 535 in accordance with privacy policy(ies), to inform User 2 of substantially all subscriber station numbers, codes or tokens, compatible with privacy policy(ies), that he/she can add automatically on a reciprocity basis; namely, User 2 can be prompted to add in related white list(s) those subscribers that have previously added him/her to their with list(s). White list configuration request 555 can be effected through various interfaces like an online GUI, a real time prompt/alert delivered to a mobile device linked to subscriber 560, or an interface component in provisioned femto access point, via SMS, MMS, email, instant message, USSD communication, and so forth.

Figure 6A:
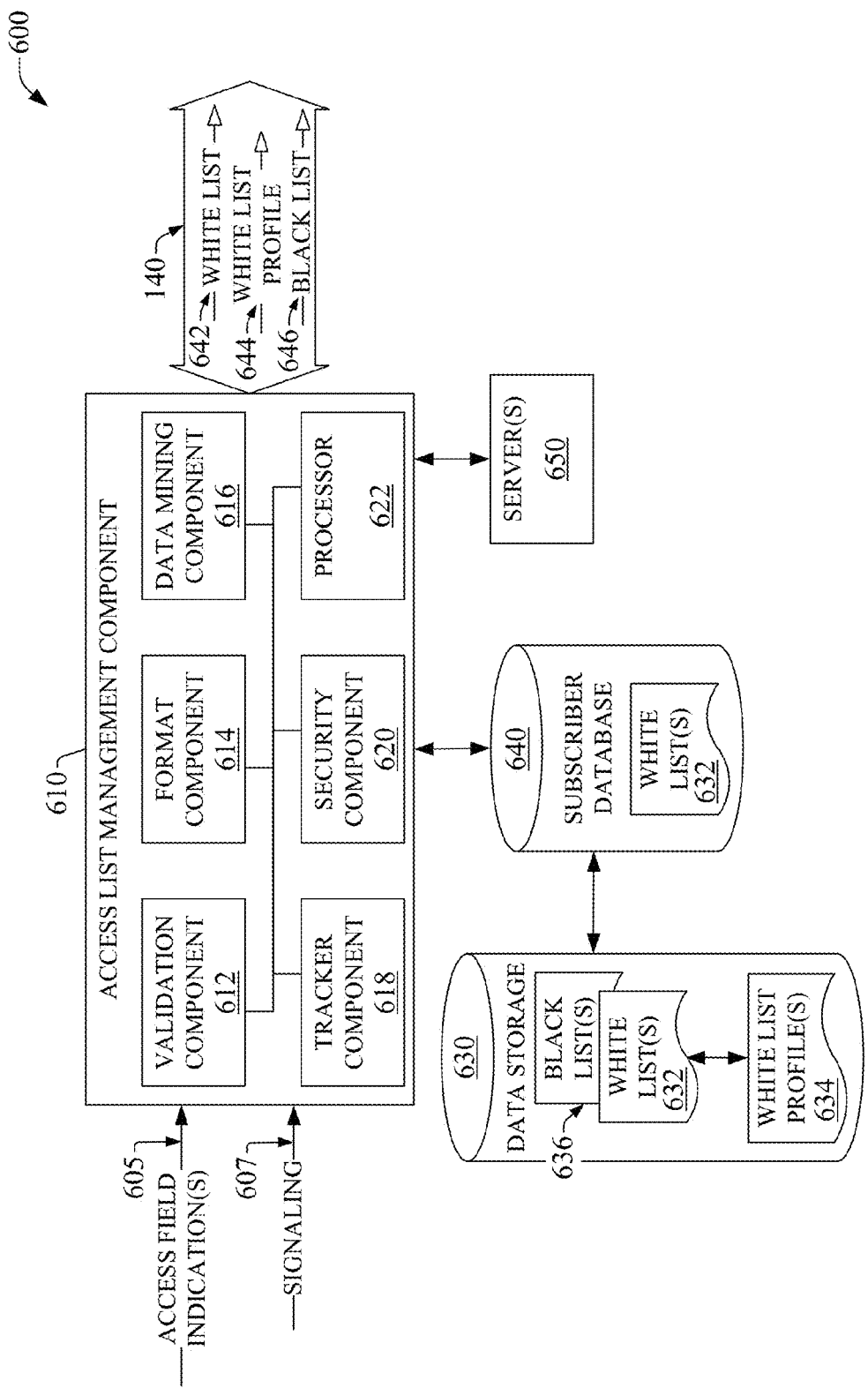
FIGS. 6A and 6B is a block diagram of an example system that facilitates generation of access control list(s) and white profile list(s) to manage access to femto cell coverage, and example white list, black list and access profile, respectively, in accordance with aspects disclosed herein.
Figure 6B:
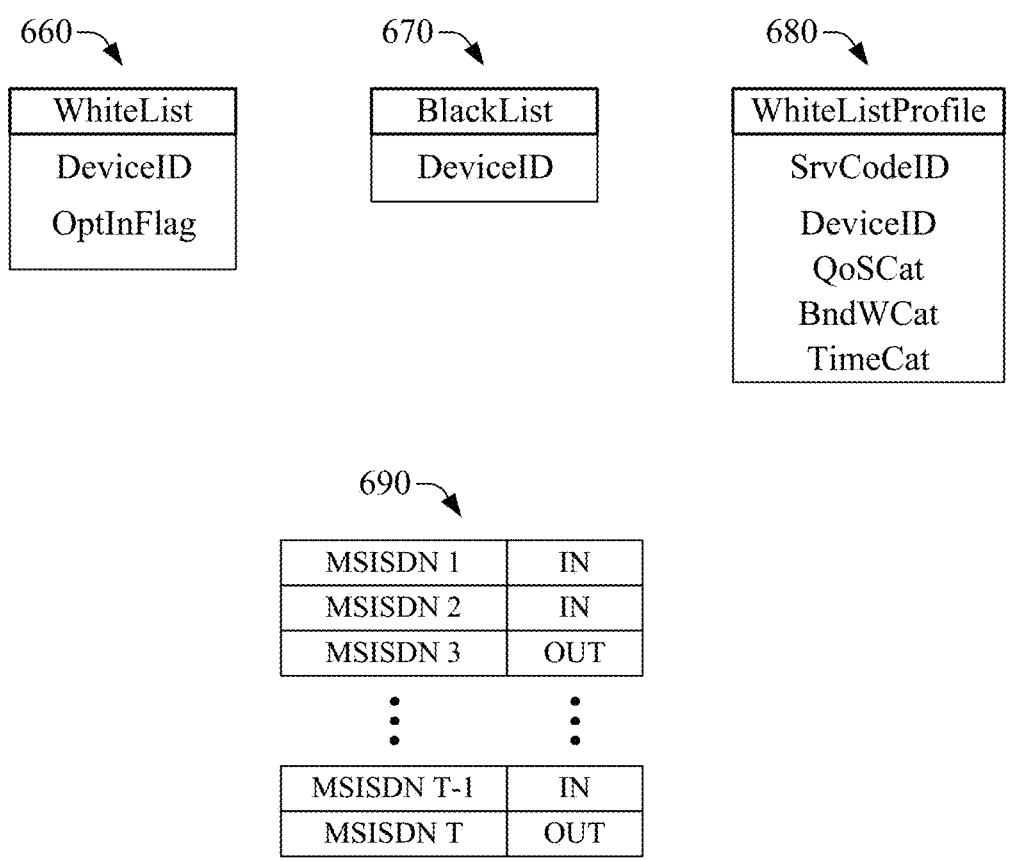

FIG. 6 is a block diagram of an example system 600 that facilitates selection of subscribers, and mobile devices linked thereto, through an initial configuration or update, to access coverage from a femto cell, or femto access point; selection can enable or disable coverage for specific subscriber(s) link to specific subscriber station(s). In connection with authorization for access to femto cell coverage, example system 600 facilitates generation of a white list profile which includes parameters that control, or facilitate access logic to, femto cell coverage as provided (e.g., granted or denied) through access control list(s) (e.g., white list(s) or black list(s)). Moreover, example system 600 can retain access list(s) (e.g., white list(s) or black list(s)), or white list profile(s), and aggregate such access list(s) and white list profile(s).

Access field(s) associated with access list(s) (e.g., white list(s) or black list(s)) attribute(s) and white list profile(s) attribute(s) can be populated with content(s) received through a set of access field indication(s) 605, which is linked to a set of mobile devices and intended for at least one of access list(s) or white list profile(s). Access field indication(s) can be received from various apparatuses or sources such as a mobile device or a server in a network (e.g., a service network linked to a mobile network platform), and can be embodied in a short message service (SMS) communication, a multimedia service (MMS) communication, an email communication, instant message (IM) communication, an unstructured supplementary service data (USSD) message, or the like. In addition, access field indication(s) 605 can be embodied in lower level signaling such as a set of one or more bits in packet header or in control frames; packets can adopt various formats like, internet protocol (IP), frame relay, or asynchronous transfer mode (ATM). Access field indication(s) 605 can be processed by server(s) 650 that can provide the various services (e.g., email service) that facilitate the embodiments of access field indication(s). For example, a server(s) 650 can be embodied in an email server that administers an email account like towhitelist@provider.domain.com through which a subscriber can convey access field content(s), e.g., a mobile device identifier number, for a white list associated with the subscriber. The email server can extract received access field content(s) for inclusion in access control list(s) (e.g., white list(s) or black list(s)) or white list profile(s).

In addition to access field indication(s) 605, access list management component 610 can receive signaling 607, which can convey directive(s) to remove or add content(s) of access field(s) within an access list (e.g., a white list or black) or within a white list profile. In an aspect, signaling 607 can be received from various apparatuses or sources such as a mobile device or a server in a network (e.g., a service network linked to a mobile network platform), and can be embodied in a SMS communication, a MMS communication, an email communication, IM communication, a USSD message, or the like. In addition, signaling 607 can be embodied in lower level signaling such as a set of one or more bits in packet header or in control frames.

In example system 600, validation component 612 can ensure integrity of data, e.g., content(s) identified through received access field indication(s) 605, related to access list(s) (e.g., white list(s) 632 or black list(s) 636) and white list profile(s) 634; access list management component 610 can receive access field indication(s) 605. In an aspect, validation component can validate (e.g., either accept or reject) a mobile device identifier attribute through one or more check procedures that rely on a set of criteria applied to the received access field indication(s) 605 of the identifier attribute value. At least one of data mining component 616 or tracker component 618 can assist with validation of field content(s) received through access field indication(s) 605. For example, tracker component 618 can monitor changes (e.g., updates) to subscribed service and identifier numbers for served subscribers, while data mining component 616 can gather information related to one or more criterion on the set of criteria, through networked access to subscriber database 640, or substantially any, or any, other database or data storage 630 accessible to a mobile network that facilitates coverage through a femto access point (e.g., femto AP 130) or a macro cell base station. It is noted that data exchange among access data mining component 618 and accessible databases can proceed securely; security mechanism(s) can be provided, in an aspect, by security component 620. The set of criteria can include at least one of the following. (i) Valid mobile device identifier (e.g., wireless device numbers such as MSISDNs, codes or tokens). (ii) Active mobile device identifier, or identifier flagged for update; e.g., received access field indication(s) 605 conveys an identifier field that corresponds to an old phone number that is to be updated to a current number. (iii) Status of election (e.g., opt in) or non-election (e.g., opt out) flags for inclusion in a white list, wherein status is conveyed, for example, via a K-bit word (K is a natural number) within an entry for the mobile device in a subscriber database. (iv) Operational capabilities of the mobile device (e.g., wireless technology utilized by the device such as second generation (2G), third generation (3G), or fourth generation (4G) technologies, radio frequency bands in which the mobile device can receive communications . . . ). (v) commercial standing (e.g., good standing or outstanding bill payments, hotlined mobile device in view of recurring lack of timely payments for service, stolen device . . . ); or the like.

Access list management component 610 can generate at least one of access list(s) (e.g., white list(s) 632 or black list(s) 636) or white list profile(s) 634 based at least in part on valid received access field indication(s) 605. Generated access list(s), e.g., white list(s) 632 or black list(s) 636, and generated white list profile(s) 634 can be retained in data storage 630. It should be appreciated that data storage 630 can be deployed at least in part within a service provider network platform (e.g., macro network platform or femto network platform) that exploits access list management component 610, or in network(s) external to the service provider network platform such as non-mobile network platform(s) (e.g., broadband internet service provider, enhanced 911 service, billing platforms, multimedia services . . . ). Alternatively, or in addition, access list(s) or white list profile(s) can be stored in a subscriber database which is typically linked to the service provider network platform. Example white list 660 and a realization 690, black list 670, and white list profile 680 are presented in FIG. 6B. Example white list 660 includes two access field attributes: DeviceID, which uniquely identifies a device, and OptInFlag which indicates whether a specific device has opted in for dissemination, or inclusion, in disparate white lists; realization 290 of example white list 660 illustrates T (a natural number) access fields populated with MSISDN 1-T for access field attribute DeviceID, and character type access fields for access field attribute OptIn. Example black list 680 includes a single access field attribute DeviceID, while example WhiteListProfile 680 includes five access field attributes: SrvCodeID, a unique identifier for a service profile given by the 4-tuples in the profile; DeviceID which is a foreign key that identifies a device for which service profile code applies; a QoSCat attribute, e.g., conversational; a BndWCat attribute that determines how much bandwidth device identified through DeviceID is allotted; and TimeCat attribute which indicates a time interval during which the attributes are granted.

Access list management component 610, through format component 614, can format access list(s) (e.g., white list(s) 632 or black list(s) 636) or white list profile(s) 634 in accordance with various schemas, such as hypertext markup language (HTML) and extensible markup language (XML) and variants (e.g., state chart XML (SCXML)), that are portable among computing platforms, wireless (e.g., a portable computer or mobile device) or otherwise, and object-oriented computing languages employed by a wireless device such as Delphi, Visual Basic, Python, Perl, Java, C++, and C#, and circuitry programming level languages such as Verilog. Such portability can facilitate straightforward exchange of access list(s) (e.g., white list(s) or black list(s)) among subscribers and related billing groups of a service provider. Extensibility afforded by such formats can facilitate aggregation of access lists (e.g., white lists) and extraction of at least portions thereof, in web-based applications web-based commerce (ecommerce) systems, blogs, peer-to-peer exchange web applications, social networking websites, or the like; it should be appreciated that aggregation and extraction of access lists (e.g., white lists) can be conducted, through at least one of data mining component 616 or validation component 612 in access list management component 610, as a part of access list(s) (e.g., white list(s) or black list(s)) administration at the network level. Additionally, format component 614 can compress (e.g., via non-lossy wavelet-based compression) or index aggregated access list(s) (e.g., white list(s) 632 or black list(s) 636) for efficient storage. Moreover, format component 614 can commit an identifier to an access list (e.g., white list(s) 632) in a network native format (e.g., full-length digit for a MSISDN or IMSI), or via unique identifier code numbers for the device (e.g., electronic serial number (ESN), international mobile equipment identity (IMEI), or mobile equipment identification (MEID)). It is noted that subscribers are not generally exposed to such formats. It should be appreciated that a white list and a white list profile can be merged into a single component or entity.

Access management component 610 can convey, via broadband backhaul pipe 140, at least one of generated white list 642, white list profile 644, or black list 646. It should be appreciated that when no access field indication(s) 605 are received, access list management component 610 can convey a default white list 642 with an identifier attribute populated with identifier fields for substantially all, or all, wireless devices provisioned to a subscriber that acquires femto cell service. It should be appreciated that access list management component 610 can reside within a femto access point (e.g., femto AP 130), e.g., within access management component 355. In such a scenario access management component 610 can convey at least one of generated white list 642, white list profile 644, or black list 646 to a memory within the femto access point.

Generation of access list(s) (e.g., white list(s) 632 or black list(s) 636) and white list profile(s) 634 as described in connection with aspects and features of example system 600, provides at least the following three illustrative advantages. (1) Security against devices attempting to hack into the femto AP when networked with it, and support of extensible sharing/networking of the authorization scheme; e.g., white list(s) can be shared. (2) Capacity to determine and customize quality of service (QoS), grade of service, or service experience, for specific authorized subscribers; in an aspect, such capacity enabled or provided via utilization of white list profile(s)

634. (3) Capacity to ensure integrity of data related to access list(s) (e.g., white list(s) 632 or black list(s) 636) and white list profile(s) 634.

It is noted that in example system 600, processor 622 confers at least in part the described functionality of access list management component 610 and components therein. Processor 622 can be configured to execute code instructions stored in a memory (not shown), or a memory component thereon, to provide at least a portion of the described functionality. It should be appreciated that the processor can be a centralized element or be distributed among the above referenced components, server, and platform.

Various illustrative aspects of the subject application based at least in part on an access control list(s) (e.g. white list(s) or black list(s)) concept are discussed next. It is to be noted that variations and extensions of such illustrative aspects are possible and are within the scope of the subject application.

Figure 7A:
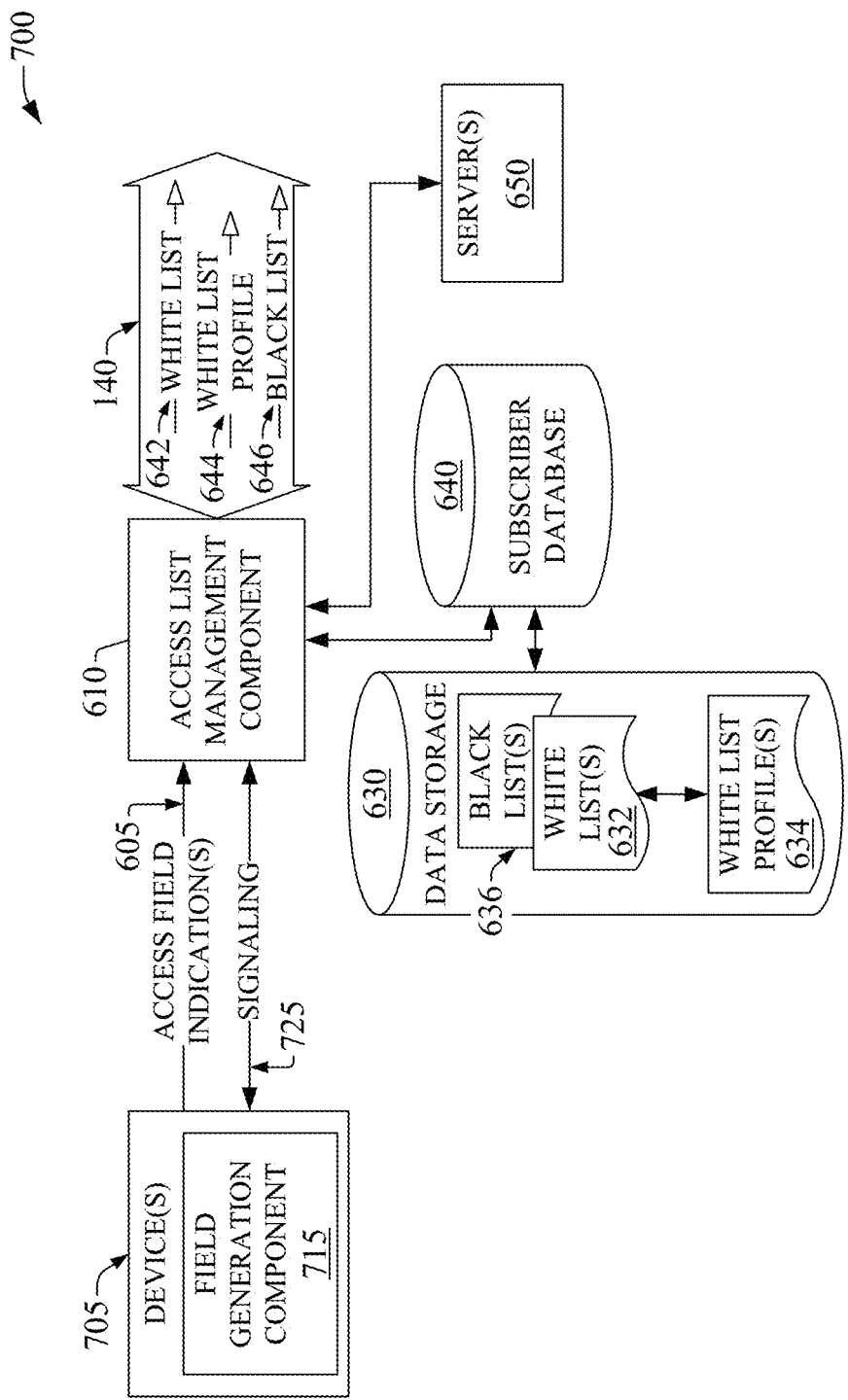
FIGS. 7A-7B illustrate block diagrams of example systems that exploit an access management component to configure or update access control list(s) (e.g., white list(s) or black list(s)) or white list profile(s) according to aspects described herein.
Figure 7B:
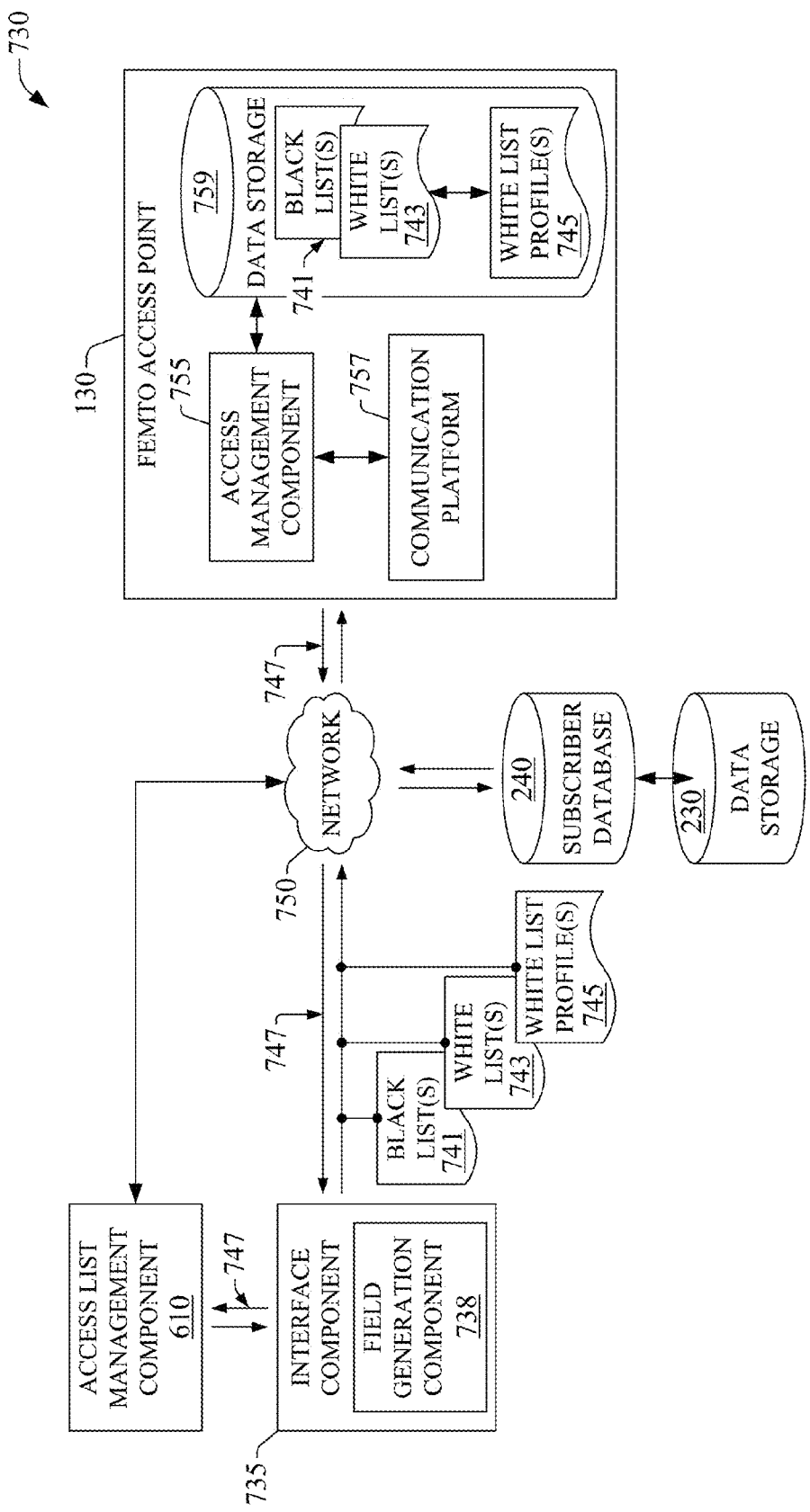

FIGS. 7A-7B illustrate block diagrams of example systems that exploit an access management component to configure or update access control list(s) (e.g., white list(s) or black list(s)) or white list profile(s) according to aspects described herein. In example system 700, mobile device(s) 705 generates and delivers one or more access field indication(s) 605. It should be appreciated that mobile device 705 need not be served, even though it can be served, through femto service to deliver access field indication(s) 605; for instance, such indication(s) can be conveyed out-of-network (e.g., via a visited network or roaming network). In an aspect, field generation component 715 can generate a set of one or more access field indication(s) 605. As described above, access field indication(s) 605 can convey field content(s) for access list(s) attributes or white list profile attribute(s). In addition, mobile device(s) 705 can convey signaling 725 in conjunction with access field indication(s) 605 in order to manipulate access control list(s) (e.g., white list(s) or black list(s)) or white list profile(s), wherein manipulation includes at least one of removal of specific attribute fields, or update of an attribute field. It is noted that removal or update can be effected in one or more access control list(s) or white list profile(s) as indicated in received signaling 725. It is noted that mobile device(s) 705 also can exchange signaling 725 with access list management component 610 to receive authorization to convey access field indication(s) 605; security component 620 can implement, at least in part, secure communication (e.g., password protection, encryption, or the like).

In an aspect, conveyed content(s) can provide a new identifier attribute field for mobile device in order to update a white list 642 associated with a subscriber that operates mobile device(s) 705. As an example, an individual can remotely provide access to femto coverage to a home appliance with wireless capability in order for a technician who services the appliance be able to run diagnostics for the appliance in a remote server and exploit the substantive broadband bandwidth of backhaul backbone that connects the femto AP to a mobile network platform.

In another aspect, access field indication(s) 605 delivered through device(s) 705 can include an updated service attribute field for a white list profile 644 to update the access logic for a mobile device identified in a white list 642 associated with a subscriber that has access to a femto access point. As an example, a trusted visitor in a home (e.g., a grandparent taking care of grandchildren during after-school hours) can be added from a remote location (e.g., workplace) to white list 642 in a temporary session with full privileges to access femto service in the home.

In addition, mobile device 705 can send signaling 725 to request add-on services associated with a device identifier attribute field in a white list 642. Such add-on service can be supported at least in part through server(s) 650. As illustrative, non-limiting scenarios, add-on services can include usage monitoring, configuration of alarms when specific usage of femto service is effected, e.g., a multi-hour download of age inappropriate content(s), chat sessions with sources of unknown reputation, call activity logs, or the like. It should be appreciated that one or more add-on services abide by privacy settings (not shown) associated with the add-on service; validation component 612 can enforce such privacy settings.

With respect to FIG. 7B, example system 730 facilitates manipulation of access list(s), e.g., black list(s) 741, white list(s) 743, and white list profile(s) 745 in accordance with aspects described herein. Interface component 735 facilitates configuration, or setup, of white list(s) 743, and white list profile(s) 745 of wireless mobile station numbers approved for coverage through femto access point 130. It is to be noted that substantially any identification token(s), label(s), or code(s) that identify a subscriber station can be employed as identifier attribute field(s) in white list(s). In addition, interface component 735 can facilitate configuration of black list(s) 741 and white list profile(s) 745.

Through field generation component 738, interface component 735 facilitates generation of access field indication(s) which are conveyed, via network link(s) 747, for example, to access list management component 610. It is noted that network link(s) 747 can be embodied in a Gi reference link. As discussed above in connection with FIG. 6, access list management component 610 can generate access list(s) (e.g., white list(s) or black list(s)) and white list profile(s), which are conveyed to interface component 735. In an aspect, field generation component 738 can receive through interface component 735 one or more values for various attribute fields that define an access list(s) (e.g., black list(s) 741 or white list(s) 743) or white list profile(s) 745. It is noted that interface component 735 can convey attribute fields that are include in the access list(s) or white list profile(s), in order to prompt entry of values for attribute fields (e.g., a mobile device identifier such as a 10-digit mobile directory number, a MSISDN number, an IMSI number, a flag to opt-in/opt-out of inclusion of white list(s), a value that allows specific service categories . . . ).

In example system 730, interface component 735 is networked (e.g., via a wide area network (WAN), local area network (LAN), or backhaul pipe like backhaul network backbone 140) with femto AP 130 and conveys black list(s) 741, white list(s) 743, or white list profile(s) 745 over network link(s) 747. In an aspect, interface component 735 can connect to femto AP 130 via secure login (e.g., virtual private network, secure file transfer, secure copy . . . ) supported at least in part by network 750. It is noted that network 750 can include one or more networks that facilitate at least in part operation of interface component 735 and communication with femto access point; for example network 750 can include non-mobile broadband internet service provider, local area network, or a mobile network platform (e.g., a core network in a cellular telecommunication environment).

In an aspect, interface component 610 can be a web-based, online graphic user interface (GUI); however, other networked interfaces that facilitate to enter, or configure, white list(s) are possible; for instance, voice or sound commanded interface(s), touch commanded interface(s), biometric commanded interfaces(s), and the like. It is noted that all possible embodiments can include field generation component 738, which can expose an operator that interacts with interface component 735 to prompts and other indicia or gestures to gather values for attribute fields for black list(s) 741, white list(s) 743, or white list profile(s) 745. In example scenarios, it should be appreciated that biometric commanded interface(s) can be employed in environment(s) wherein addition(s) to white list(s) 743 or black list(s) 741, or white list profile(s) 745 is controlled by authorized personnel with specific clearances to add/remove attribute fields, since communication can be classified.

Additionally, in example system 730, a communication platform 255 in femto access point 130 facilitates reception of at least one of black list(s) 741, white list(s) 743, or white list profile(s) 745, and conveys the received at least one of black list(s) 741, white list(s) 743, or white list profile(s) 745 to an access management component 235 that can exploit the received access list(s) (e.g., white list(s) 743) to manage access (e.g., grant, deny, or adjust or modulate) to coverage provided by femto AP 130. The received at least one of black list(s) 741, white list(s) 743 or white list profile(s) 745 can be stored in data storage 759 in the femto AP 130; even though white list(s) 220 and white list profile(s) 222 can be stored in disparate network components like a network component (e.g., subscriber database 240 or data storage 230) administered by a service operator. In addition, interface component 735 can access a subscriber database 240 through network 250, in order to extract identification numbers or identifiers, codes, tokens, or labels for subscribers/subscriber stations that can be entered in a access list(s) (e.g., black list(s) 741, white list(s) 743) or white list profile(s) 745.

It is noted that in example systems 700 and 730, respective processors (not shown) confer at least in part the functionality of the described components and platform(s). Processor(s) can be configured to execute code instructions stored in a memory (not shown), or a memory component thereon, to provide at least a portion of the described functionality. It should be appreciated that the processor can be a centralized element or be distributed among the above referenced components, server, and platform.

In contrast to management of access authorization via femto access point 130, configuration (e.g., setup or update) of access list(s) (e.g., black list(s) 741, white list(s) 743 (registration authorization for femto coverage)) and white list profile(s) 745 through network mechanisms (e.g., interface component 210) provides at least the following advantages. It is to be noted that the following advantages are illustrative and not limiting, as other advantages associated with white list(s) 220 are possible and are intended to lay within the scope of the innovation(s) as described in the subject specification. (1) Access through a networked interface (online or otherwise) reduces provisioning lead time and provides a means for customers to update and personalize femto AP autonomously (e.g., free of interaction with technical support entities) at substantially any time. (2) Security against devices attempting to hack into the femto AP when networked with it, and support of extensible sharing/networking of the authorization scheme; e.g., white list(s) can be shared. (3) Networked interface (online or otherwise) provides a superior, rich customer experience substantially free of requirement(s) to understand/interpret femto AP programming interface or configuration nomenclature. (4) End user(s) can manage (e.g., remove select covered numbers, or add additional numbers for coverage up to an allotted amount (e.g., upper bound N) for white list(s) associated with the user. (5) Capacity to determine and customize quality of service (QoS), grade of service, or service experience, for specific authorized subscribers; in an aspect, such capacity enabled or provided via utilization of white list profile(s) 234. (6) Capacity to ensure integrity of data related to access list(s) (e.g., white list(s) 232 or black list(s) 236) and white list profile(s) 234.

Figure 8:
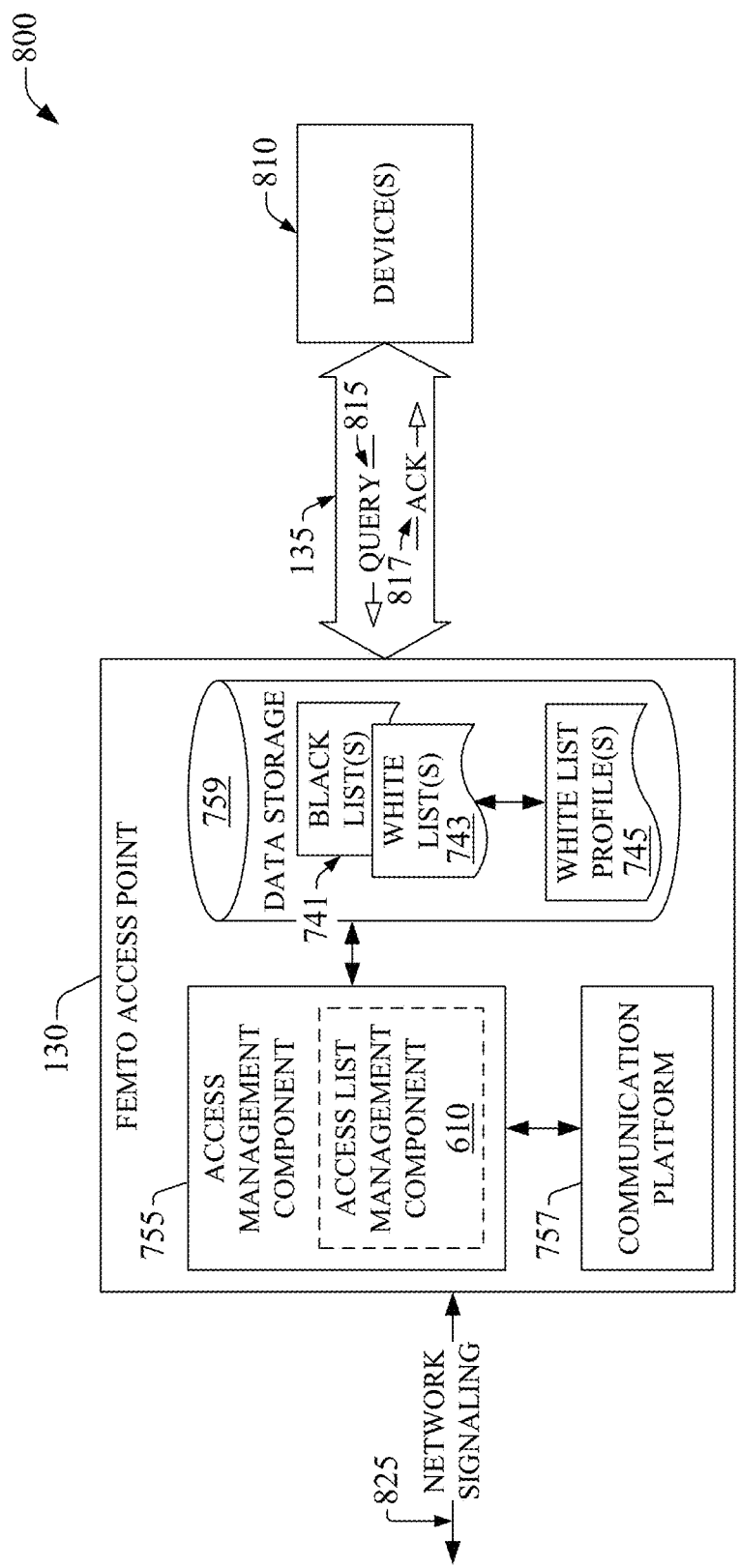
FIG. 8 is a block diagram of an example system that facilitates addition to a white list of mobile device identifier attribute fields on an ad hoc basis in accordance with aspects described herein.

FIG. 8 is a block diagram of an example system 800 that facilitates addition to a white list of mobile device identifier attribute fields on an ad hoc basis in accordance with aspects described herein. In example system 800, device(s) 810 can convey, e.g., through signaling, a request or query 815 to access coverage of femto AP 130; query 815 can be delivered in a control channel when femto AP 130 operates in wireless broadband mode or in a management frame or packet when in-band operation of femto AP 130 is implemented. It should be appreciated that a multi-mode chipset can operate, at least in part, communication platform 757 in order for it to receive and convey signal in various telecommunication mode(s). Query 815 can be received by communication platform 757, and access management component 755 can be configured to allow or reject the request; allowance of rejection of a request can be based on various metrics, such as security, type of device, profile of subscriber linked to the device that requests access, and so on. Configuration to allow or reject the request includes exchange of network signaling 825 in order to access relevant information associated with mobile device 810. In an aspect, access management component 820, which can operate in substantially the same manner as access list management component 610, can facilitate validation of requester device(s) 810 based upon the aforementioned metrics.

Upon allowance of a request (e.g., query 815), access management component 755 can query for available slots, or attribute fields, to be filled in white list(s) 743 associated with account(s) served by femto AP 130. When memory space necessary to include an identifier attribute field value is available for a subscriber station identifier number (e.g., MSISDN, IMSI, ESN, IMEI), code or token, query 815 can further probe whether access is allowed on a permanent, or temporary basis (e.g., to reduce risk exposure to security problems). Characteristics of femto coverage allowance can be set or pre-set through access management component 755 through determination of white list(s) 743 and associated white list profile(s) 745. In an aspect, white list profile(s) 745 can dictate access privilege(s) for an allowed requester mobile device 810 in accordance with default attribute field values in white list profile(s) 745, which can be configured through access list management component 820 at a time femto access point 130 is provisioned. As an example, a default white list profile can allow limited service (e.g., only voice) to requester device(s) 810, or it can customize attribute fields in the default white list profile based at least in part on information gathered in connection with requester device(s) 810. Subsequent to allowance and examination of information related to relevant white list(s) 743, access management component 755 updates white list(s) 743, and related white list profile(s) 745, stored in data storage 759, to reflect the approved request for femto coverage. Upon an identifier for requester device(s) 810 is entered in white list(s) 743, an acknowledgment (ACK) 817 is delivered to device(s) 810 to indicate addition to white list(s) 743 and femto service privileges accorded via white list profile(s) 745. It is to be noted that access and update of collected subscriber identifier numbers (e.g., MSISDN, IMSI), codes, or tokens, also can be implemented through network-based white list database(s), via at least in part network signaling 825. It is to be noted that query 815 can be conveyed via an online GUI (e.g., interface component 735); an email message; a SMS communication; a MMS communication; USSD (or * and # codes) messaging; a voice mail, in order to utilize recognition as a security layer prior to grant access to femto AP coverage; a web prompt; or the like.

An illustrative, non-limiting advantage of example system 800 is that it provides an enhanced end user experience with a direct, clear mechanism to add new mobile device identifiers in white list(s), and thus encourages use of the femto access point 130, and avoids time spent on edition of white list(s) through a networked interface (e.g., interface component 210) like an online interface which typically takes time, a minimum degree of technological savvy, for the end user to access to the Internet and log on in a secured interface, for example.

It should be appreciated that substantially any wireless device within coverage area of femto AP 130 (e.g., area 125) can request access without intervention of a subscriber that operates femto AP 130, and who has previously entered a set of subscriber station numbers (e.g., MSISDNs, IMSIs), codes or tokens, via a networked interface (e.g., interface component 735), for example. Alternatively, or in addition, a request for access (e.g., query 815) can be prompted by a device utilized by a subscriber that operates the femto AP. Further a request for access can be effected by the femto AP, through an access management component like component 755, for example. Once a request is granted, a secure tunnel can be established from the device/client through the femto cell's internet protocol (IP) connection or the default connection of a radio access network (RAN) if the IP connection is not available. Secure layers including utilization of the femto cell's virtual private network (VPN) and/or USSD messaging would ensure that the transaction related to edition or manipulation of white list(s) 743, or white list profile(s) 745, is in fact secure. In an aspect, a security component within access management component can facilitate at least in part the secure communication.

As an example, a temporary visitor (e.g., a relative on vacation) or employee (e.g., a babysitter) who is coming over to a location served by a femto access point (e.g., femto AP 130) for a limited period of time, can be provided with coverage via the femto AP by a subscriber that operates the femto cell so the employee can perform, at least in part, his work activities (e.g., provide updates on behavior of children, be contacted reliably through a mobile device . . . ) through utilization of the femto access point. In case the subscriber fails to know identifier numbers (e.g., MSISDNs, IMSIs), codes, or tokens for mobile devices the employee can utilize, and the subscriber is not interested to go through the process of requesting and entering the numbers (e.g., MSISDNs, IMSIs), codes or tokens via a networked interface (e.g., interface component 735) to allow coverage for the limited period of time the employee performs work, the employee (e.g., babysitter) can convey a request (e.g., query 815) for access to femto coverage directly from the employee's device when in range of the femto access point (e.g., within area 125).

Figure 9:
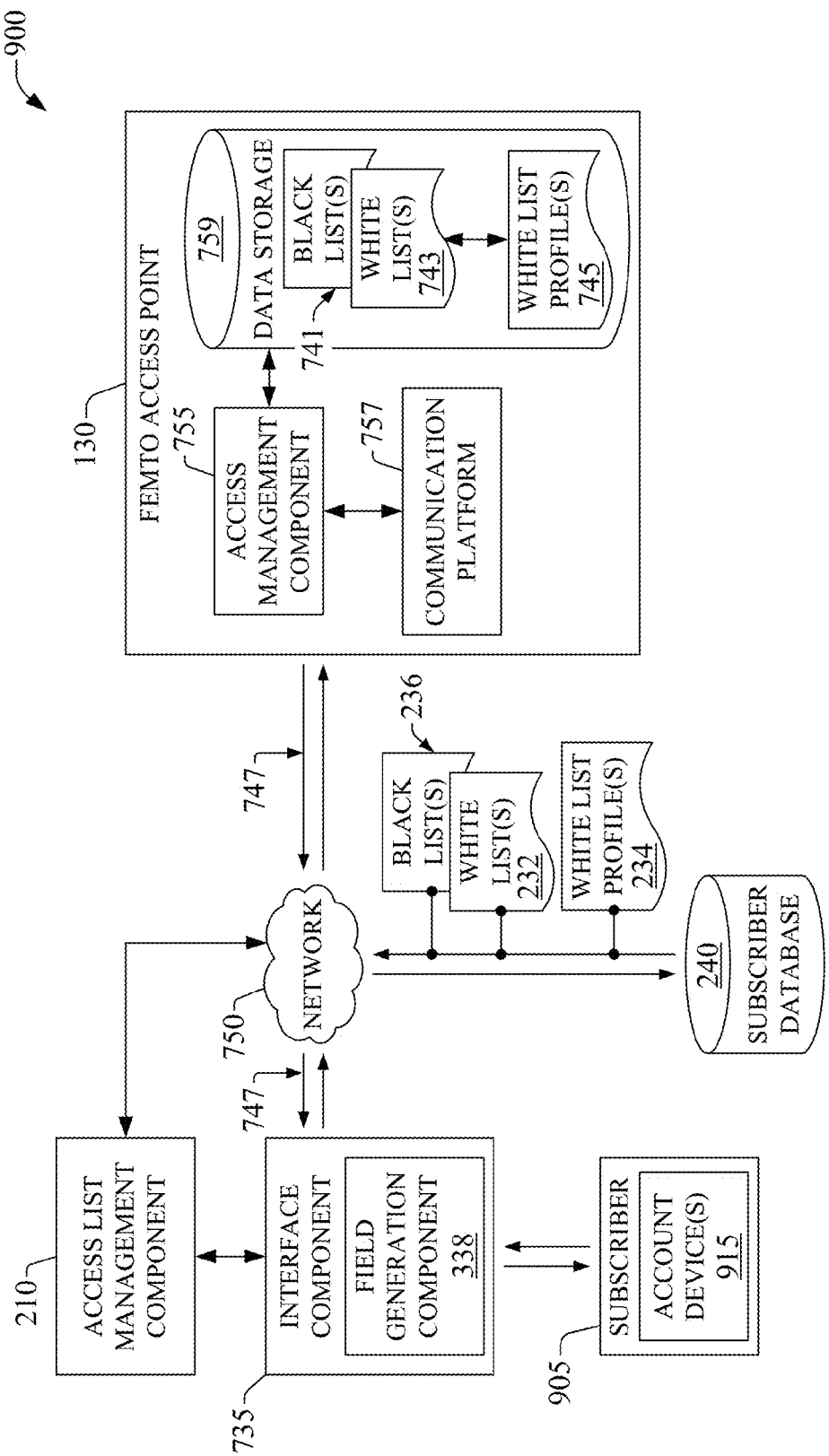
FIG. 9 is a block diagram of an example system that facilitates automatic population of access list(s) (e.g., white list(s) or black list(s)) and generation of white list profile(s) in accordance with aspects described herein.

FIG. 9 is a block diagram of an example system 900 that facilitates automatic population of access list(s) (e.g., white list(s) or black list(s)) and generation of white list profile(s) in accordance with aspects described herein. In example system 900, a subscriber 905 who utilizes account device(s) 915, can provision femto AP 130 and associate account device(s) 915 with a service account via networked interface component 735 (e.g., an online account management system) which can look up into substantially all subscriber station(s) identifier numbers (e.g., MSISDNs), codes or tokens associated with the service account, and automatically populate access list(s) (e.g., white list(s) 232 or black list(s) 236) with the extracted subscriber station(s) numbers, codes or tokens. Account device(s) 915 is part of a subscriber's service account, which can be an account for femto service, and/or macro service, wherein one or more account consumers are billed in accordance to the same billing scheme (e.g., voice and data rating, price point(s) for add-on applications, price point(s) for store on-the-cloud . . . ). As an example, the set of account devices 915 can include handsets and phone numbers (e.g., an IMSI number) that identify the handsets, or cards for wireless service (e.g., subscriber identity module (SIM) cards). It is noted that subscriber 905 can generally access the 10-digit mobile subscriber identification number provided by a network operator, rather than full-length identifier numbers (e.g., identifier field attributes) for account device(s) 915.

Subscriber 905, via interface component 735, can remove or add subscriber station(s) numbers (e.g., MSISDNs, IMSIs), codes, or tokens, extant in pre-populated white list(s) 232; additional edits can be performed as well, based at least in part on the complexity of white list(s) 232 and desired access privileges to femto coverage, provided by femto AP 130, that are to be conferred to whitelisted (e.g., included in white list(s) 232) mobile devices as dictated by white list profile(s) 234. In an aspect, to pre-set white list(s) 220, networked interface component 735 access information stored in subscriber database 260 through network 230 which can include information technology systems of a service provider, and data storage related to service network(s) (e.g., internet protocol (IP) multimedia subsystem (IMS)) that provide services to a mobile network platform administered by the service provider. Subscribers that present election flags that decline inclusion in white list(s) are not provided for subscriber 905 to browse. Additionally, to further ensure privacy, partial identifiers in conjunction with a selector component (not shown) can be provided to subscriber 905 to provide access field indication(s) (e.g., identifier attribute fields) associated with mobile device that opted in to access list management component 210. As discussed above, white list(s) 220 and white list profile(s) 222 are conveyed through network 750 via network link(s) 747 to femto access point 130 and retained therein; communication platform 255 receives white list(s) 232, and access management component 755 stores access list(s) (e.g., white list(s) 743 or black list(s) 741) and white list profile(s) 745 in data storage 759.

Interface component 735 can prompt, or query, subscriber 905 in connection with establishment of access list(s), e.g., white list(s) or black list(s), and receive responses associated thereto. Prompt(s) can be generated by field generation component 738, or a provisioning server (not shown) associated with access list management component 210. In an aspect, prompts are directed to collection of subscriber preferences in connection with configuration of access list(s) (e.g., white list(s) or black list(s)) for the set of account devices 915 and identifier attribute fields thereof that can be provided by subscriber 905. Field generation component 738 also can prompt subscriber 905 to provide content(s), e.g., parameter(s), for attribute field(s) that determine characteristics of service (e.g., temporary access, permanent access, specific services . . . ) to be provided to account device(s) 915 entered in an access list (e.g., white list(s) 232).

Illustrative advantages provided by example system 900 are (a) reduced femto cell provisioning lead time, and (b) immediate utilization of a femto cell with mobile numbers that belong to a same service account, with the ensuing billing simplifications (e.g., bundle pricing, voice credits reutilization or transfer among whitelisted (e.g., committed to a white list(s)) numbers, etc.); operation monitoring capabilities (e.g., a parent can monitor usage of voice and data services through femto AP 130 of a child) which can be set through parameter(s) in white list profile(s) such as white list profile(s) 234; enhanced indoor wireless coverage; and so forth; whether subscribers of such numbers subscribe to the femto cell or a feature application, or code, that delivers a femto cell service.

It is noted that in example system 900 a processor (not shown) can confer at least in part the described functionality of the various components or platform(s) in the example system 900, and component therein, included aforementioned systems. The processor can be configured to execute, and execute, code instructions stored in a memory (not shown), or a memory component thereon, to provide at least a portion of the described functionality. It should be appreciated that the processor can be a centralized element or be distributed among the various referenced systems, component, networks, and platform.

Figure 10:
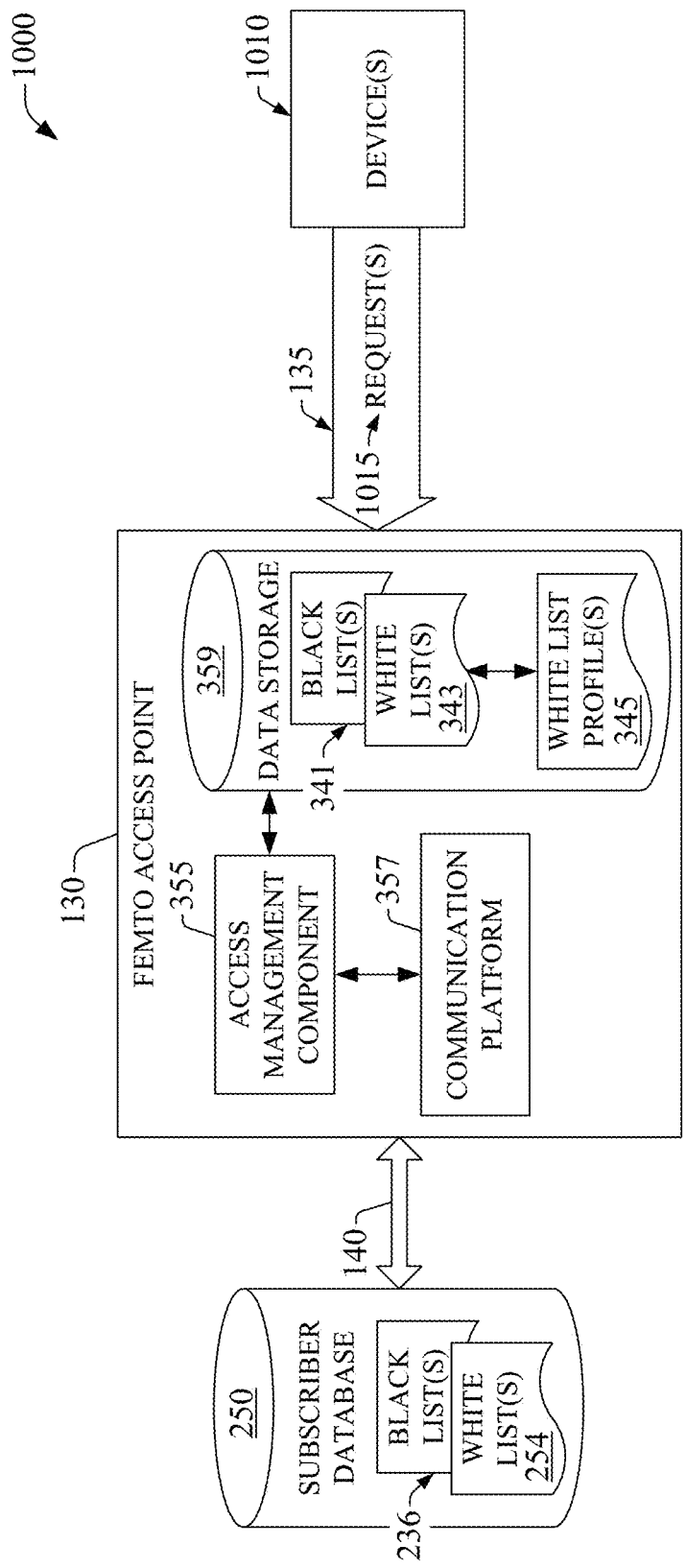
FIG. 10 is a block diagram of an example system that tracks subscriber station identifier attribute fields associated with access list(s) (e.g., white list(s) or black list(s)) on record with a femto service provider in accordance with aspects of the subject application.

FIG. 10 is a block diagram of an example system 1000 that tracks subscriber station identifier attribute fields (e.g., MSISDNs, IMSIs), codes or tokens, associated with access list(s) (e.g., white list(s) or black list(s)) on record with a femto service provider in accordance with aspects of the subject application. When a subscriber (e.g., subscriber 905), or end user, that operates mobile device(s) 1010 cancels an account or subscription with a wireless service provider or changes an identifier number, code, or token, associated with mobile device(s) 1010 and that serves as an identifier attribute field in white list(s), the subscriber can convey a request 1015 via mobile device(s) 1010 to remove the identifier number thereof from substantially all, or all, white list(s) 232 on record in a subscriber database 240 or substantially any other database available to a service provider that contains information on service subscribers. It should be appreciated that request(s) 1015 can be conveyed as signaling in a control channel or management frame for control communication with femto access point 130. In an aspect, access management component 225 can convey an indication to a mobile wireless platform (e.g., a core network), via backhaul pipe 140, to update white lists (e.g., white list(s) 254) associated with a subscriber linked to device(s) 1010 in accordance to request(s) 1615. It is noted that local records of white list(s) 343 are also updated as a result of request 1015; local update takes place in all femto APs that include white list(s) that comprise mobile device 1010 identifier number that is cancelled.

Additionally, or alternatively, when an end user changes mobile or subscriber station number, code or token, (e.g., after relocation to a new area code, or the like), request(s) 1015 can be delivered to femto access point 130 to automatically update substantially all, or all, white list(s) 254 on record that include mobile device 1010 identifier number, code, or token. Access management component 755 can deliver signaling via backhaul pipe 140 to a mobile network platform to update white list(s) 1020 records in subscriber database 230. It is noted that local records of white list(s) 743 in all femto APs that include white list(s) that comprise mobile device 1010 identifier number that is updated.

An illustrative advantage of such on-request automatic update of white list(s) 232, and local white list(s) 743, is ease of use for end users to maintain current white lists at the network level and local, e.g., femto AP 130, level without a need to track each of the end user's subscriber station number, code, or token associated with the white list(s) 254. In addition, updated white list(s) 254 and white list(s) 343 maintain the value proposition of the femto cells for end users and service operator by a seamless move of traffic off of the macro network (e.g., a WAN) to femto network(s).

In view of the example systems described above, example methodologies that can be implemented in accordance with the disclosed subject matter can be better appreciated with reference to flowcharts in FIG. 11-18. For purposes of simplicity of explanation, the example methodologies, or methods, are presented and described as a series of acts; however, it is to be understood and appreciated that the claimed subject matter is not limited by the order of acts, as some acts may occur in different orders and/or concurrently with other acts from that shown and described herein. For example, it should be understood and appreciated that a methodology, or method, could alternatively be represented as a series of interrelated states or events, such as in a state diagram, or interaction diagram. Moreover, not all illustrated acts may be required to implement a methodology in accordance with the subject specification. Additionally, it is noted that two or more methodologies, or methods, can be enacted in conjunction. Furthermore, it should be further appreciated that the methodologies, or methods, disclosed hereinafter and throughout this specification are capable of being stored on an article of manufacture to facilitate transporting and transferring such methodologies, or methods, to computers for execution by a processor or for storage in a memory.

Figure 11:
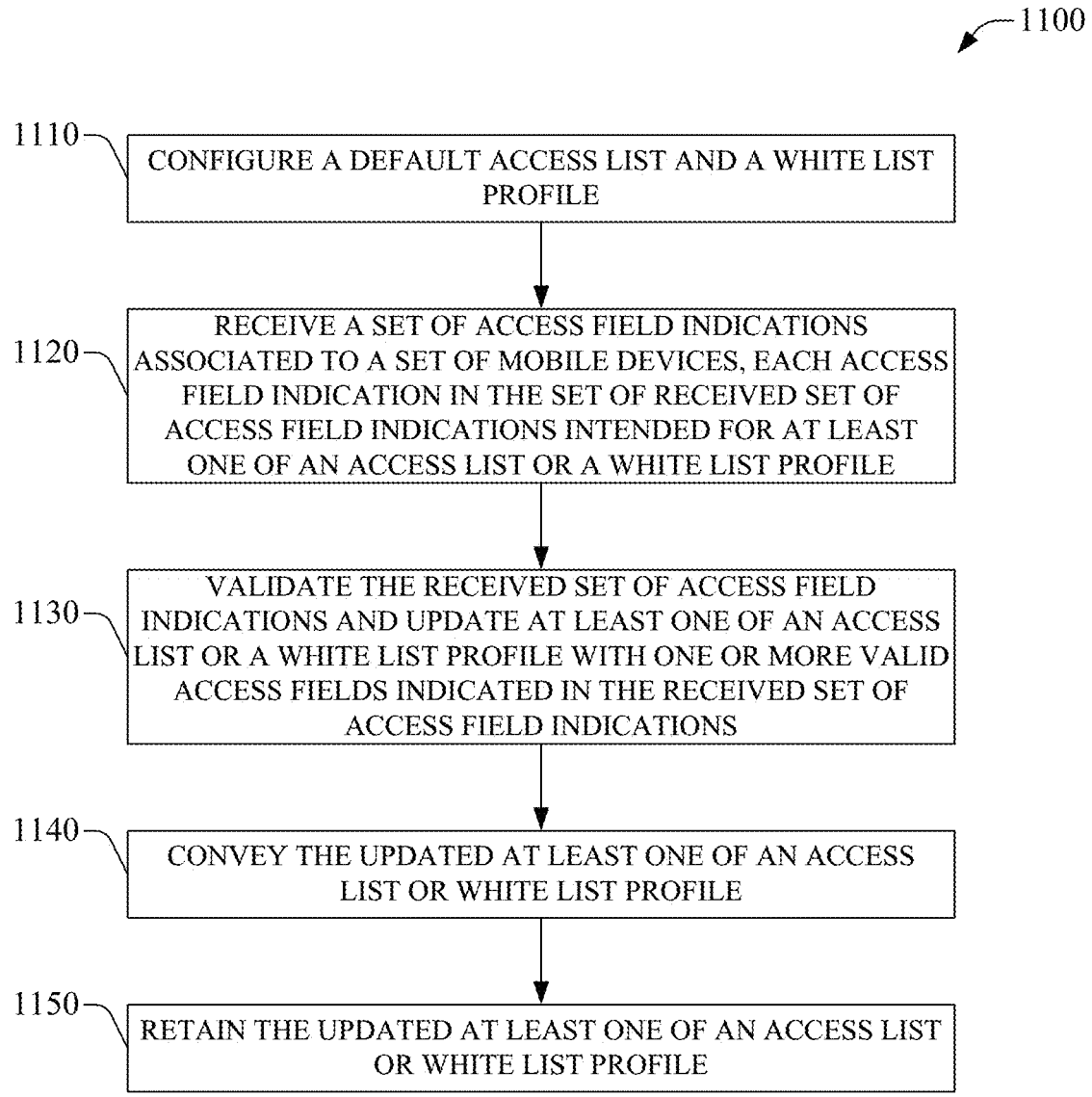
FIG. 11 is a flowchart of an example method for updating an access list (e.g., a white list or black list) and a white list profile according to aspects described herein.

FIG. 11 is a flowchart of an example method 1100 for updating an access list (e.g., a white list or black list) and a white list profile according to aspects described herein. The subject example method 1100 can be enacted by a component within a mobile network platform (e.g., a core network in cellular technologies such as 3GPP UMTS, 3GPP Long Term Evolution (LTE), 3rd Generation Partnership Project 2 (3GPP2) Ultra-Mobile Broadband (UMB)). At act 1110 a default access list and default white list profile are configured. Configuration of an access list can include populating a set of access fields and committing the access list (e.g., a white list or a black list) to memory (e.g., a subscriber database). Default access field values for a white list can include a single field that identifies a mobile device for a subscriber that provisioned a femto access point for which the white list is intended. For a black list, default access field values can include a NULL descriptor and thus no mobile device is explicitly denied access to a femto access point. With respect to a default white list profile, each mobile station associated with an access field that identifies the mobile station in a white list related to the default white list profile is allowed full access to femto service or coverage; the full access dictated by a service plan acquired by a subscriber for which the femto AP is provisioned.

At act 1120, a set of access field indications associated to a set of mobile devices is received, each field indication in the received set of field indication is intended for at least one of an access list or a white list profile. The set of access field indications can convey at least in part a set of identifiers, or identification numbers, for each mobile device in the set of mobile devices; the identifiers include MSISDNs, IMSI numbers, or codes or tokens that uniquely identify a mobile device at the hardware level, such as ESN, IMEI, MEID or the like. In addition, access field indications can convey access field values that establish access privileges to femto coverage; privileges can include type of service, time span of coverage, technologies allowed to be employed within coverage area, etc. More particularly, access fields that determine coverage privileges can determine at least one of time intervals for an identified mobile device to access femto coverage; privileges to access voice and data services provided through a provisioned access point that utilizes access list(s) to provide coverage, wherein the privileges dictate degree of access to a service such as QoS profile (e.g., best effort or guaranteed quality of service); allocated bandwidth; preemption profile or relative priority of access to service (e.g., video streaming, sound streaming, voice . . . ) for various mobile devices in a white list, emergency calls are not preempted; or the like.

At act 1130, the received set of access field identifications is validated and at least one of an access list or a white list profile are updated with one or more valid access fields indicated in the received set of access field indications. In an aspect, validation includes at least one of verifying a mobile device associated with a field that identifies the mobile device is flagged to opt in for inclusion in femto access service, or identifying commercial standing (e.g., outstanding bill payments, hotlined mobile device, stolen device) of the mobile device associated with the one identifier allows the one identifier to be entered in a white list.

At act 1140, the updated at least one of an access list (e.g., a white list or a black list) or white list profile is conveyed. In an aspect, the access control list or white list profile are conveyed to a provisioned femto access point. At act 1150, the updated at least one of an access list (e.g., a white list or a black list) or white list profile is retained. The access control list or white list profile can be retained in a subscriber database or in data storage, which can be associated with at least one of a network platform that provides telecommunication service(s) (e.g., femto or macro coverage) or one or more disparate networks linked to the network that provides telecommunication service(s). Data storage can be localized within a single network or distributed among various networks.

Figure 12A:
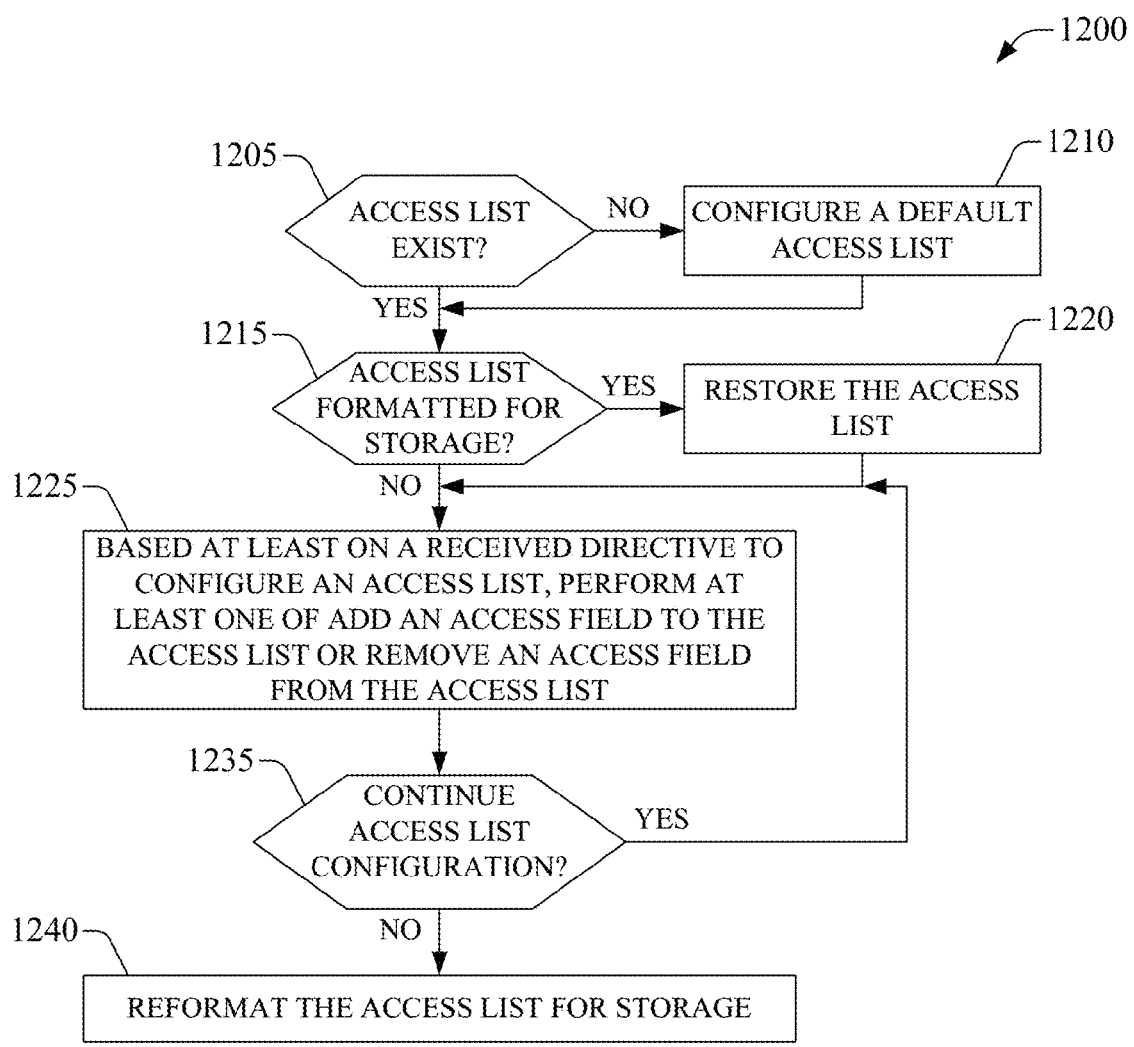
FIGS. 12A and 12B present, respectively, flowcharts of example method for updating an access list (e.g., a white list or a black list) and a white list profile according to aspect of the subject application.
Figure 12B:
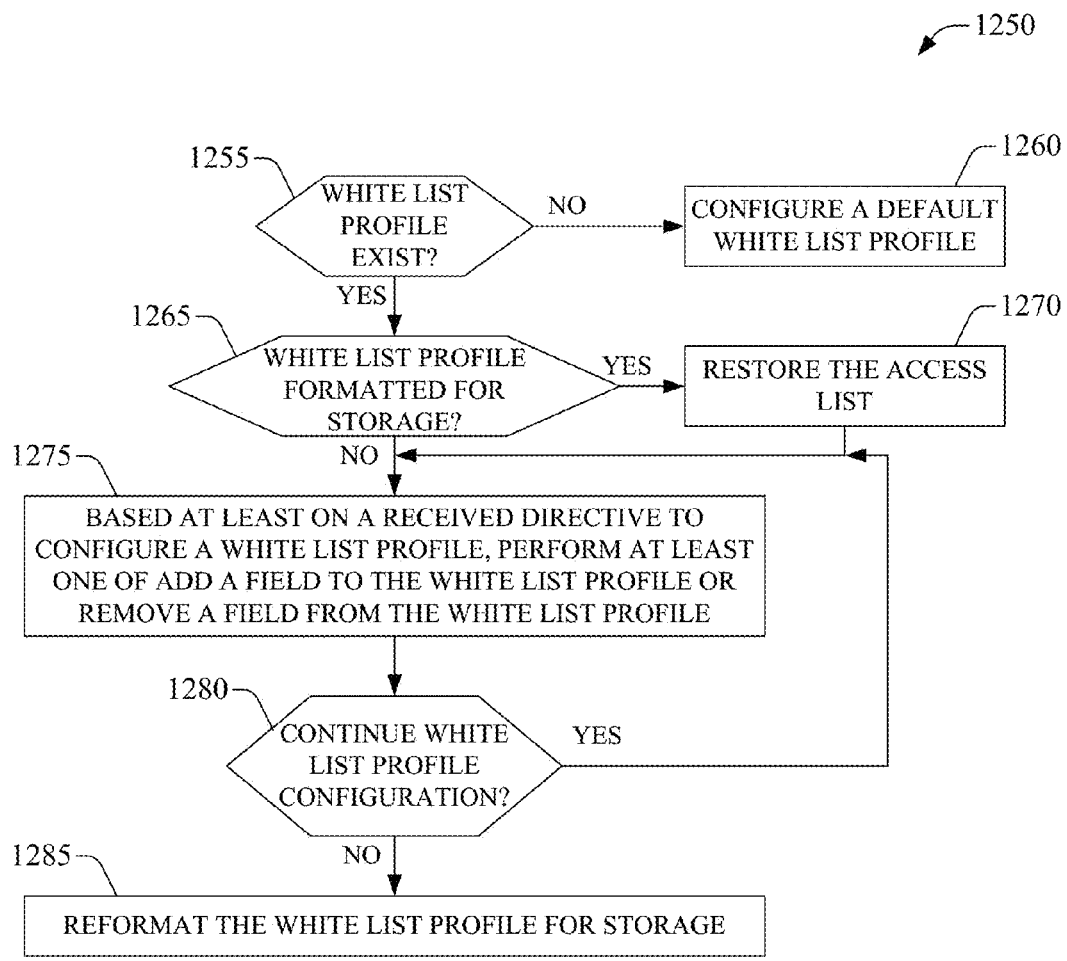

FIGS. 12A and 12B present, respectively, flowcharts of example methods 1200 and 1250 for updating an access list and a white list profile according to aspect of the subject application. The subject example methods can be enacted by a component (e.g., access list management component 210) within a mobile network platform. It should be appreciated that example methods 1200 and 1250 can be enacted concurrently when a white list and a white list profile are merged into a single component or entity in memory. At act 1205 it is checked whether an access list exists. In the negative case a default access list is configured at act 1210 and flow is directed to act 1215, which is enacted when the outcome of act 1205 is positive and probes whether an existing access list is formatted for storage. In an aspect, format for storage of an access list can include various representations such as binary format, wavelet compressed format, indexed representation, or the like. Such storage formats are advantageous particularly when access lists (e.g., white lists) for several ($10^4$-$10^6$) femto access points are aggregated or cross-linked as a result of sharing access lists. When outcome of act 1215 is positive, the access list is restored and flow is directed to act 1225. Conversely, at act 1225, based at least on a received directive (e.g., signaling 725) to configure access list, at least one of add an access field to the access field list or remove an access field from the access list. It should be appreciated that addition or removal of an access field in an access field can be dynamic in that memory is dynamically allocated upon addition and dynamically deallocated upon removal of an access field. Alternatively, field content(s) can be added to or removed from a static memory allocation for the access list. At act 1235, it is checked if access list configuration is to be continued. In the affirmative outcome, flow is directed to act 1225. Conversely, flow is directed to act 1240 in which the access list is reformatted for storage; for instant, the updated list is aggregated with a set of access lists and recompressed.

With respect to FIG. 12B, in example method 1250 in connection with white list profile update, at act 1255 it is checked whether a white list profile exists. In the negative case a default white list profile is configured at act 1260 and flow is directed to act 1265, which is enacted when the outcome of act 1255 is positive and probes whether an existing white list profile is formatted for storage. In an aspect, format for storage of an access list can include various representations such as binary format, wavelet compressed format, indexed representation, or the like. Such storage formats are advantageous particularly when access lists (e.g., white lists) for several ($10^4$-$10^6$) femto access points are aggregated or cross-linked as a result of sharing access lists. When outcome of act 1215 is positive, the access list is restored and flow is directed to act 1225. Conversely, at act 1225, based at least on a received directive (e.g., signaling 725) to configure access list, at least one of add an access field to the access field list or remove an access field from the access list. It should be appreciated that addition or removal of an access field in an access field can be dynamic in that memory is dynamically allocated upon addition and dynamically deallocated upon removal of an access field. Alternatively, field content(s) can be added to or removed from a static memory allocation for the access list. At act 1280, it is checked if white list profile configuration is to be continued. In the affirmative outcome, flow is directed to act 1275. Conversely, flow is directed to act 1285 in which the access list is reformatted for storage; for instant, the updated list is aggregated with a set of access lists and recompressed. In an aspect, a format component (e.g., format component 214) can carry out the reformatting.

Figure 13:
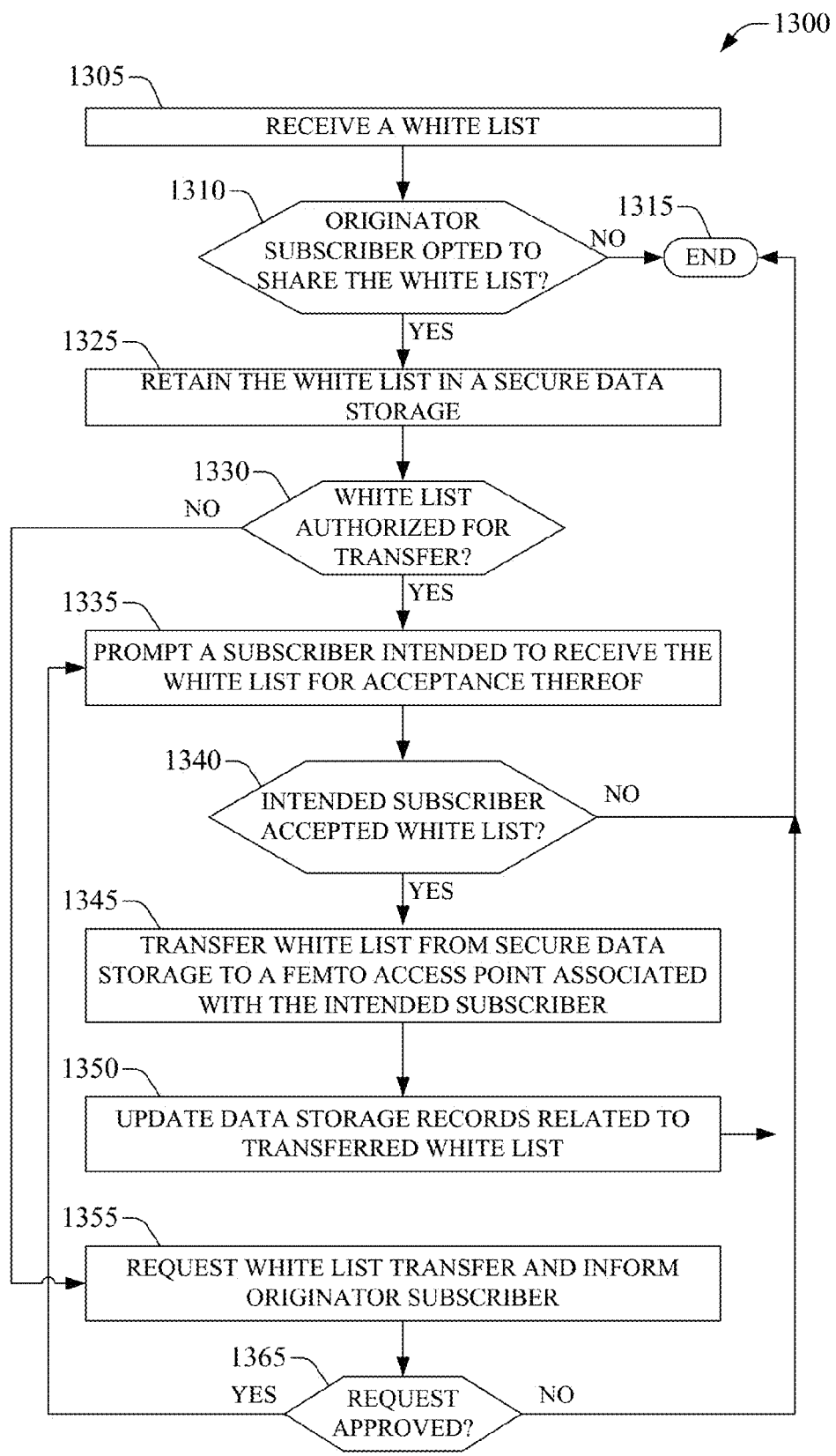
FIG. 13 is a flowchart of an example method for sharing a white list in accordance with aspects disclosed herein.

FIG. 13 is a flowchart of an example method 1300 for sharing a white list in accordance with aspects disclosed herein. It should be appreciated that while the illustrated example is presented for a white list, a black list or a white list profile can be shared through the same method. At act 1305 a white list is received; the white list is delivered by an originator subscriber that intends to share the white list. At act 1310, it is checked whether an originator subscriber opted to share the white list. An originator subscriber is the subscriber (e.g., subscriber A 210) that is the source of the white list. In the negative case, the method ends at 1315. In the affirmative case, the white list is retained in a secured data storage. In an aspect, contents of the conveyed white list are compatible with privacy policy(ies) related to white list content(s) dissemination. Data storage can be secure in various manners, for example, a security component can provide with a secure copy mechanism that can be utilized through an interface component that facilitates conveying the white list. At 1330 it is evaluated whether the white list is authorized for transfer. In the negative case, flow is directed to act 1360 and a white list transfer is requested and the originator subscriber is informed. In an aspect, originator subscriber is informed via signaling 212. At act 1365, it is checked whether the request is approved. In the negative case, flow is terminated at act 1315. Conversely, flow is directed to act 1335, in which a subscriber intended to receive the white list is prompted for acceptance thereof. In an aspect, the subscribed can be prompted through signaling, e.g., signaling 349, which can be embodied in various types of communication such as SMS communication, MMS communication, email communication, instant message communication, USSD messaging, or the like. At act 1340, it is evaluated whether the intended subscriber accepted the white list. In the negative case, flow is terminated at act 1315. In the affirmative case, white list is transferred from the secured storage location to a femto access point associated with the intended subscriber. At act 1350, data storage records related to the transferred white list are updated. Such data storage records can reside within a mobile network platform that provides wireless service, e.g., within a master database or in a femto network platform gateway node.

Figure 14:
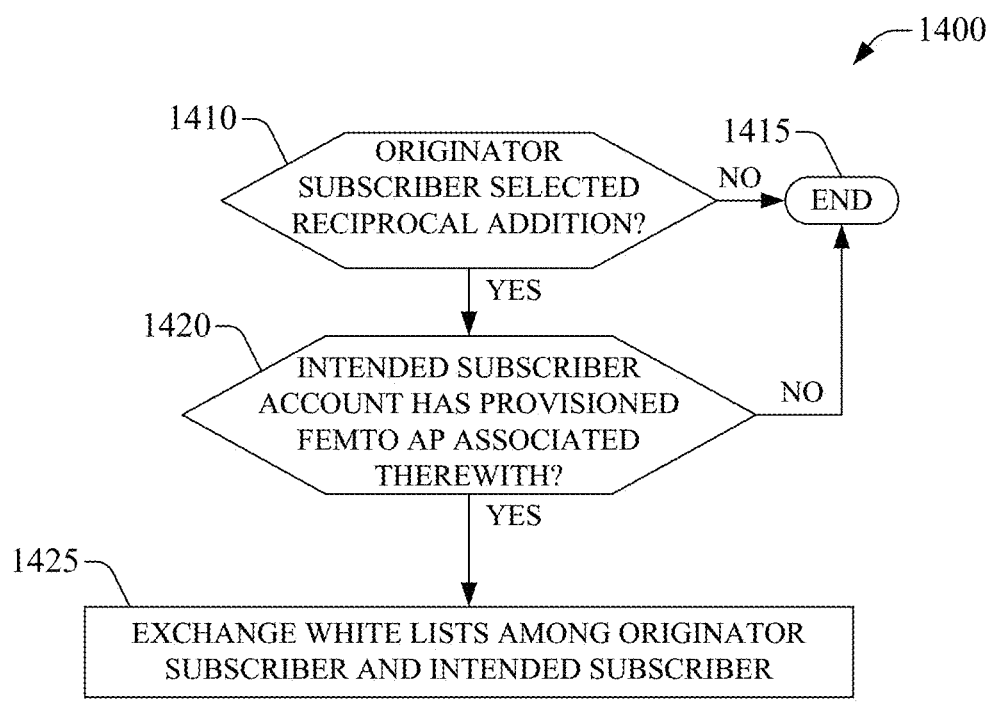
FIG. 14 is a flowchart of an example method for ensuring consistency in white list(s) exchange according to aspects described herein.

FIG. 14 is a flowchart of an example method for ensuring consistency in white list(s) exchange according to aspects described herein. In an aspect, the subject example method 1400 can be employed in conjunction with example method 1300. It is noted that the subject example method 1400 can be employed for black list(s) and white list profile(s). In act 1410, it is checked whether and originator subscriber for transmission of a white list has selected reciprocal addition in a white list. Reciprocal addition in a white list comprises accepting and receiving a white list from the recipient, or intended, subscriber for a white list of the originator subscriber. An originator subscriber is the subscriber (e.g., subscriber A 210) that is the source of the white list. Such probing can be effected by accessing privacy policy(ies) records related to the originator subscriber and retained in a subscriber database, or any data storage that contains subscriber records with a mobile network platform. Alternatively, or in addition, originator subscriber can be prompted, e.g., through signaling 212, to elect reciprocal addition. When outcome of act 1410 is negative, example method is terminated at 1415. Conversely, a positive outcome leads to act 1420, wherein it is probed whether an intended subscriber account has a provisioned femto access point associated therewith. In the negative case, example method is terminated at act 1415. Conversely, at act 1425, white lists are exchanged among originator subscriber and intended subscriber. In an aspect, exchanging white list(s) can proceed at least in part according to example method 1300.

Figure 15:
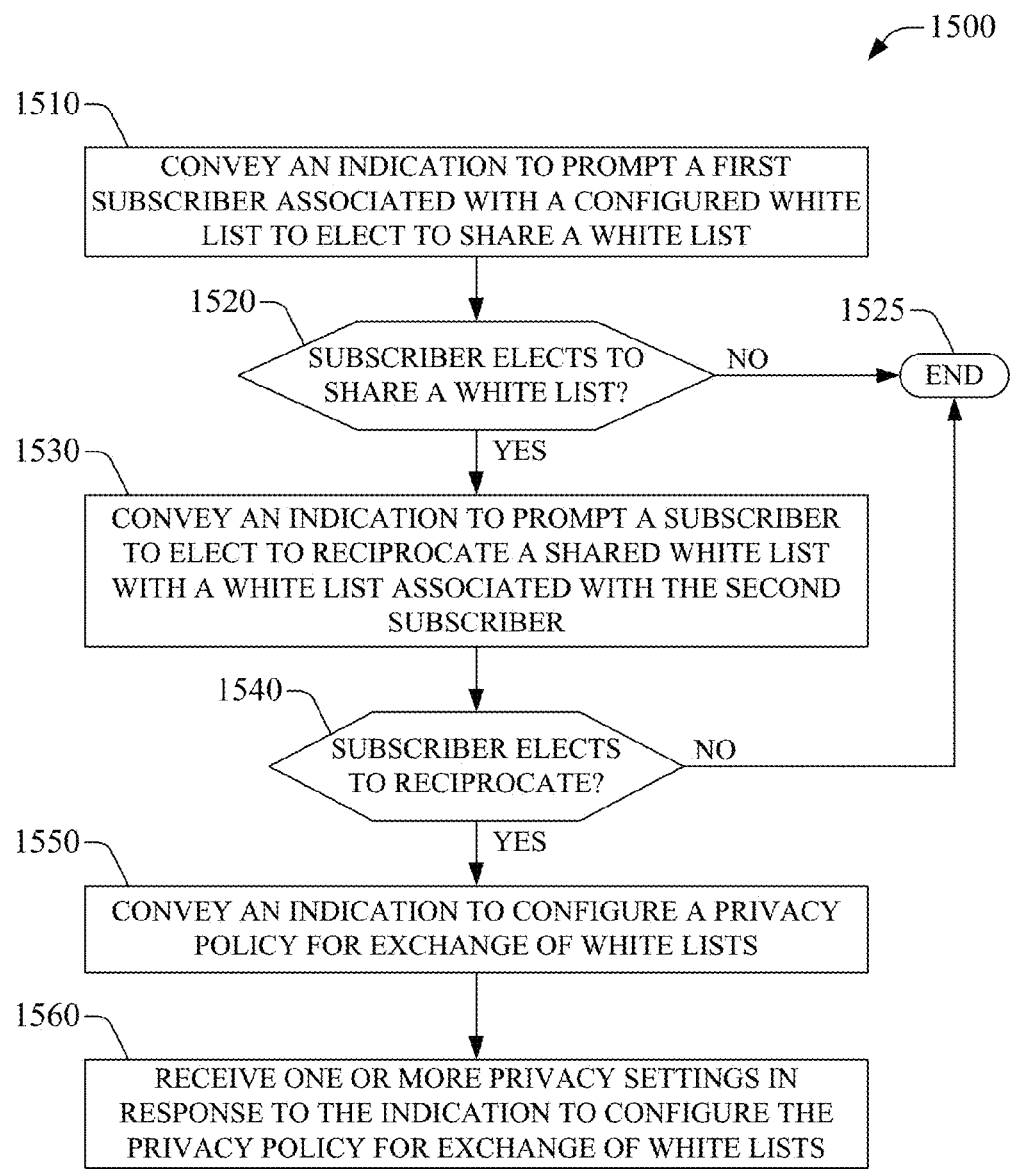
FIG. 15 presents a flowchart of an example method for configuring privacy setting(s) that establish at least in part privacy policy(ies) according to aspects described herein.

FIG. 15 presents a flowchart of an example method 1500 for configuring privacy setting(s) that establish at least in part privacy policy(ies) according to aspects described herein. It should be appreciated that while the illustrated example is presented for a white list, a black list or a white list profile can be shared through the same method. In an aspect, the subject method can be enacted through one or more components within a mobile network platform that provides femto access service. At act 1510, an indication is conveyed to prompt a first subscriber associated with a configured white list to elect to share a white list. In an aspect, signaling 212 can be utilized to deliver such indication or prompt. At act 1520 it is checked whether the first subscriber elects to share a white list. Outcome to act 1520 can be assessed through an access list management component that receives signaling, e.g., signaling 249, from a device operated by the subscriber or from a femto access point provisioned to the subscriber. When the outcome of act 1520 is negative, example method 1500 is terminated at act 1525. Conversely, at act 1530, an indication is conveyed to prompt a second subscriber to elect to reciprocate a shared white list with a white list associated with the second subscriber. At act 1540, it is probed whether the second subscriber elects to reciprocate. In the negative, example method is terminated at act 1525. In the affirmative case, at act 1550 it is conveyed an indication to configure a privacy policy for exchange of white lists among the first subscriber and second subscriber. At act 1560, one or more privacy settings are received in response to the indication to configure the privacy policy for exchange of white lists.

Figure 16:
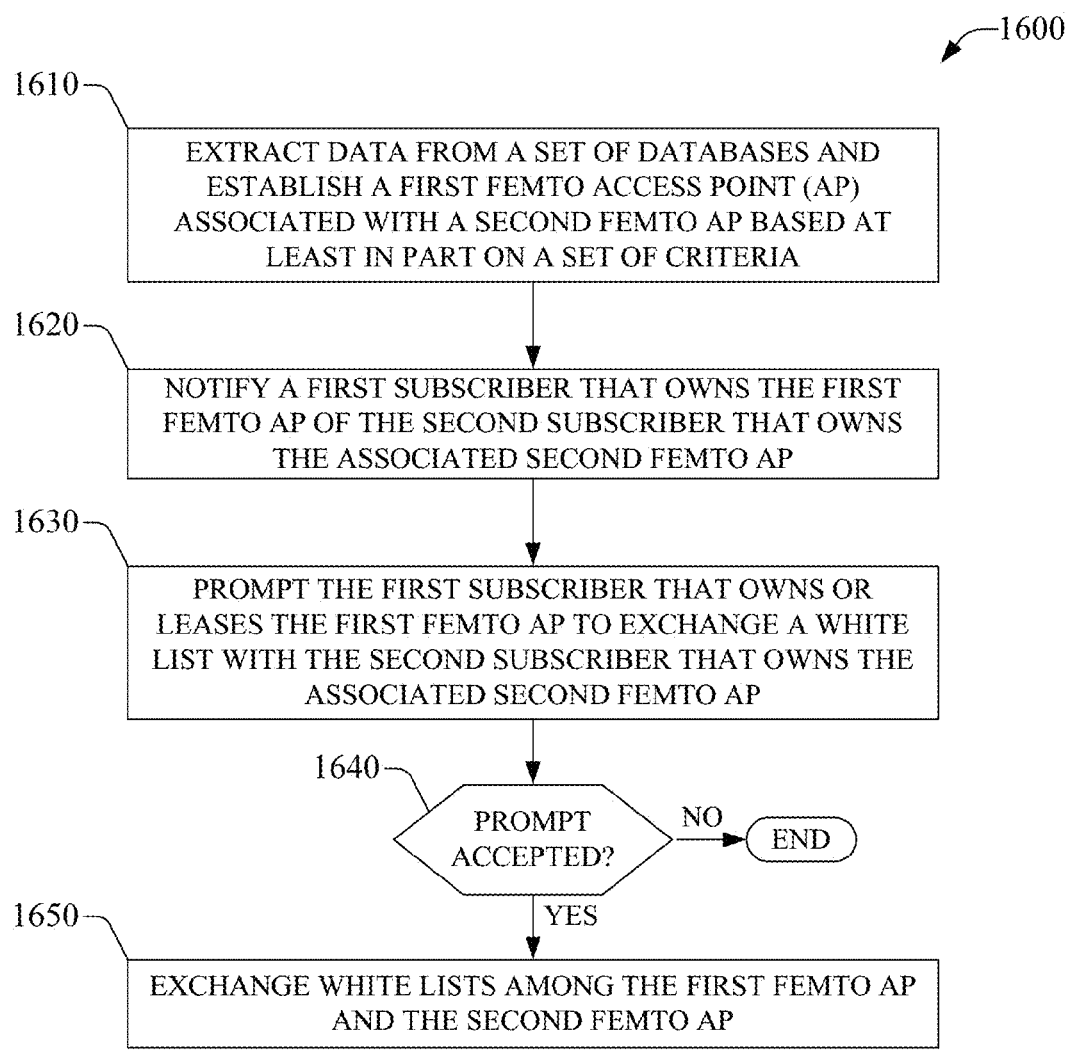
FIG. 16 presents a flowchart of an example method for establishing femto access points that can benefit from exchange of white list(s) according to aspects described herein.

FIG. 16 presents a flowchart of an example method 1600 for establishing femto access points that can benefit from exchange of white list(s) according to aspects described herein. In an aspect, the subject example method 1600 can be enacted by one or more components within a mobile network platform that operates a femto cell network; e.g., access list management component 325 or data mining 420. At act 1610, data from a set of databases is extracted and first femto access point (AP) associated with a second femto AP is established based at least in part on a set of criteria. Databases can reside within one or more networks, mobile or otherwise, that retain data associated with subscribers that are served telecommunication services through a mobile network platform. Databases can be generated through various types of servers, e.g., content servers (e.g., social network website(s), blog(s), content exchange, etc.) or ecommerce servers (e.g., online reservation system for air ticket, hotel reservation, bank transaction(s), or the like) that facilitate exchange of information among subscribers. As an example, a database can be deployed within a local area network of an airline carrier. At act 1620, a first subscriber that owns or leases the first femto AP is notified of the second subscriber that owns the associated second femto AP. Notification can be conveyed through signaling, e.g., logic system signaling such as a multi-bit word, a set of reserved bits in control packet or frame, or the like. In an aspect, information related to the second subscriber abides by privacy setting(s) that are part of a privacy policy determined by the subscriber; example method 1500 can facilitate, at least in part, to determine such privacy policy. At act 1630, the first subscriber that owns the first femto AP is prompted to exchange a white list with the second subscriber that owns the associated second femto AP. In an aspect, signaling 212 or signaling 249 can implement the prompting. At act 1640, it is checked whether the prompt is accepted. In the negative scenario, example method is terminated. In the affirmative case, at act 1650, white lists are exchanged among the first femto AP and the second femto AP.

Figure 17:
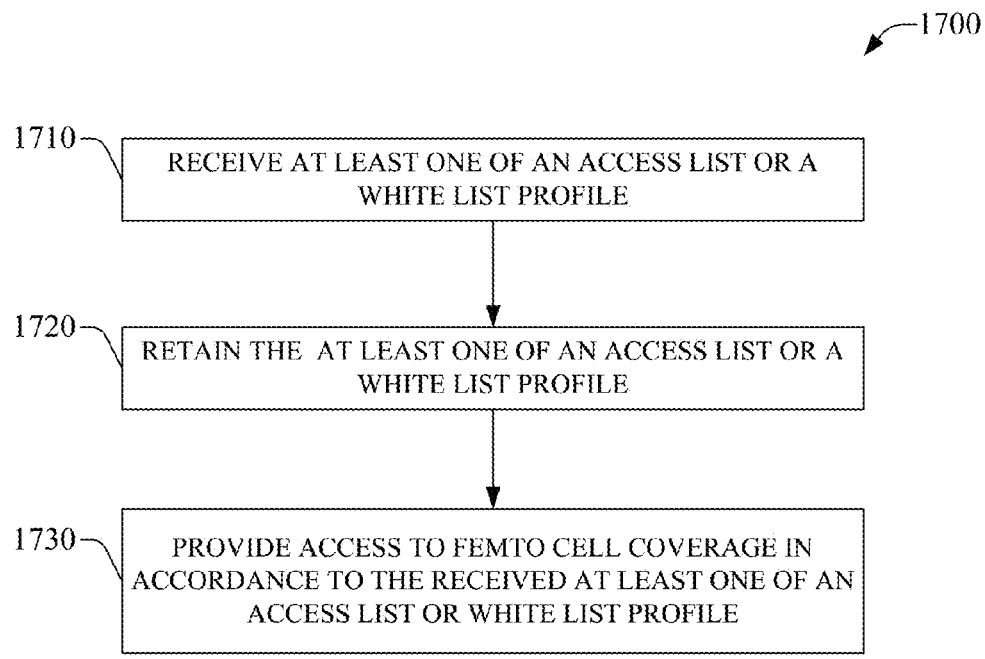
FIG. 17 presents a flowchart of an example method for utilizing an access control list (e.g., a white list or black list) or a white list profile to manage access to femto access point coverage of subscriber stations and subscribers according to aspects described herein.

FIG. 17 presents a flowchart of an example method 1700 for utilizing an access control list (e.g., a white list or black list) or a white list profile to manage access to femto access point coverage of subscriber stations and subscribers according to aspects described herein. In an aspect, the subject example method can be enacted by a femto access point (e.g., femto AP 130) that exploits the pre-populated white lists. The subject example method 1700 can be utilized with white list(s) or black list(s) and white list profile(s) configured in various manners as described in the subject specification. At act 1710, at least one of an access list or a pre-populated white list profile are received; an access list can include a white list or a black list. In another aspect, a communication platform (e.g., communication platform 357) within the femto access point receives and processes signals that carry the contents of the access list (e.g., white list(s) 343 or black list(s) 341) and a white list profile. At act 1720, the at least one of an access list (e.g., white list(s) 343 or black list(s) 341) or a white list profile (e.g., white list profile(s) 345) are retained. A memory, in the femto access AP can retain a received access list (e.g., a white list or a black list) and received white list profile. At act 1730, access to femto cell coverage is provided (e.g., granted or denied) in accordance with the received at least one of an access list (e.g., white list or black list) or white list profile.

Figure 18:
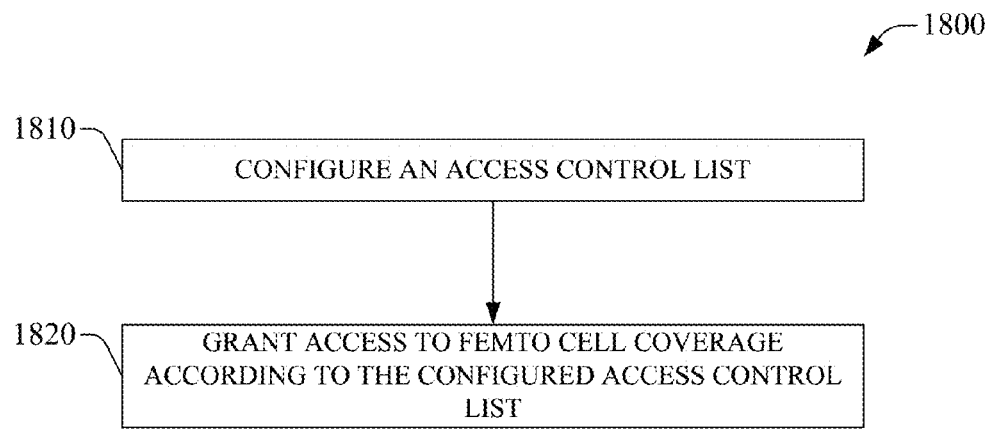
FIG. 18 presents a flowchart of an example method for managing access of subscribers and subscriber stations to femto cell coverage according to aspects described herein.

FIG. 18 presents a flowchart of an example method 1800 for managing access of subscribers and subscriber stations to femto cell coverage according to aspects described herein. At act 1810 an access control list, or white list, for a femto cell is configured. In an aspect, the subject example method can be enacted by the femto access point (e.g., femto AP 130) that exploits the pre-populated white lists. In another aspect, configuration can be performed via a networked interface, interactively or automatically based at least in part on operation conditions of the femto cell; e.g., initial provisioning, capturing of wireless devices, responding to request for access, updating extant access control lists, and so forth. At act 1820, access to femto cell coverage is granted according to the configured access control list (e.g., white list, or black list). In another aspect, the configured access control list can possess an associated profile, e.g., white list profile 234, that controls logic for utilization of the access control list, via a set of parameters that determine conditions of access, type of access, etc., as described herein.

Figure 19:
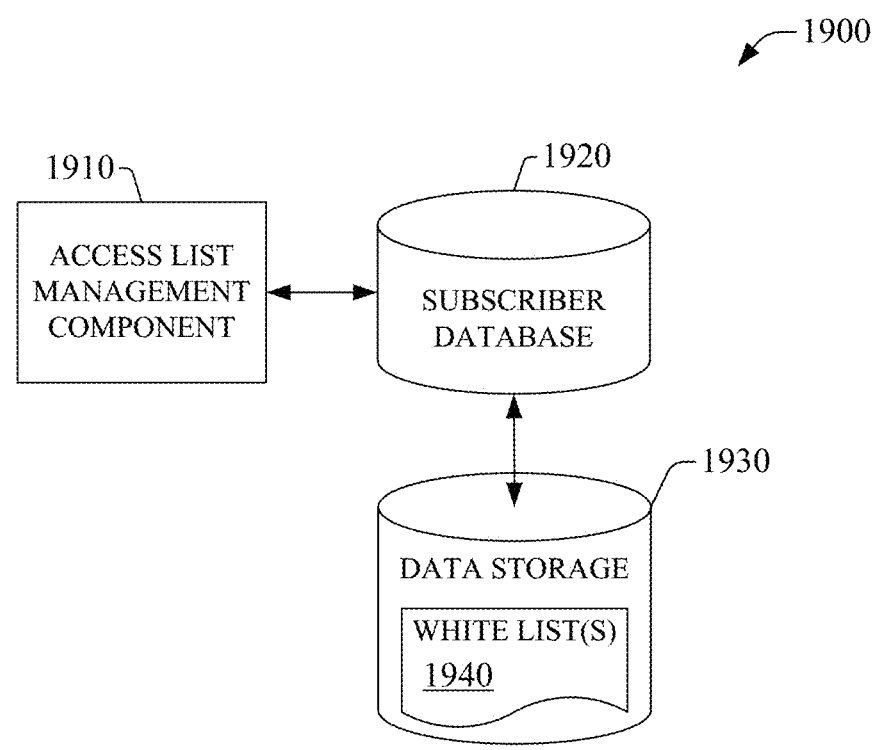
FIG. 19 is a block diagram of an example system that manages access control lists, or white lists, in accordance with aspects described herein.

FIG. 19 is a block diagram of an example system 1900 that manages access control lists (e.g., white lists or black lists) in accordance with aspects described herein. Access list management component 1910, via for example data mining component 616, can access a subscriber database 1920 which can be maintained by a service operator for femto and macro networks, and a data storage 1930 that retains a set of white lists 1940 associated with served subscribers, to associate whitelisted subscribers across disparate access control lists, or white lists. It should be appreciated that component 1910 can operate in the same manner as access list management component 210. It should further be appreciated that data storage 1930 can be associated with various network platforms (e.g., service network(s), enterprise network(s), local area network(s) . . . ) linked to a mobile network platform operated by the service provider. Such association can lead to genesis of white-list trees. In an aspect, access list management component 1920 via, for example, a format component (e.g., format component 214) can implement mechanisms to mitigate exponential data growth and efficient storage of white-list trees like data-compression (e.g., wavelet, efficient tree representation, or the like), distributed data warehouses, and so forth. In another aspect, access list management component 1920 can deploy a white-list tree in accordance to the following illustrative, non-limiting scenario. (i) User 1 adds User 2 to his/her white list. (ii) User 2 adds User 3 to his/her white list. (iii) User 1 and User 3 can be associated through white lists. (iv) User 1 and User 3 can match User 4 extant on each other's white lists. (v) User 1 and User 3 can associate User 5 that is on User 4's white list. In an aspect, access list management component 1910 effects associations and manages generated white-list tree(s). It should be appreciated that substantially any association, hierarchical or non-hierarchical, or deployment of white lists (e.g., white list(s) 1940) can be implemented by access list management component 1910 through information stored in subscriber database 1920 and data storage 1930. An illustrative, non-limiting, advantage of structured, hierarchical generation of white lists to subscribers (e.g., subscriber A 1110) is that more subscribers can have access to femto cells to gain wireless coverage enhancement, or have access to added value through unlimited usage on any femto cell or unique services available via a set of femto cells.

In addition, example system 1900 can track subscriber station identifier numbers (e.g., MSISDNs, IMSIs), codes or tokens, associated with white list(s) on record with a femto service provider. White list management component 1910 can validate white list(s) 1940, stored in data storage 1930, against current accounts and associated subscriber station identifier numbers (e.g., MSISDNs, IMSIs), codes, or tokens, for a service provider. In particular, when a subscriber (e.g., subscriber A 1410), or end user, cancels an account with service provider, white list(s) 1940 can be updated according to information retrieved from subscriber database 1920, which is updated as a result of the cancelled subscription, or substantially any other database available to a service provider that contains information on service subscribers. In addition, when an end user changes their mobile or subscriber station number, code or token, (e.g., after relocation to a new area code, or the like) substantially all white list(s) 1940 that the mobile or subscriber station number, code or token is associated with can automatically be updated by white list management component 1910.

An illustrative advantage of such automatic update of white list(s) 1940 is ease of use for end users to maintain current white list(s) 1940 without a need to keep track of each subscriber station number, code, or token associated with the white list(s) 1940. In addition, updated white list(s) 1940 maintains the value proposition of the femto cells for end users and service operator by a seamless move of traffic off of the macro network (e.g., a WAN) to femto network(s).

Figure 20:
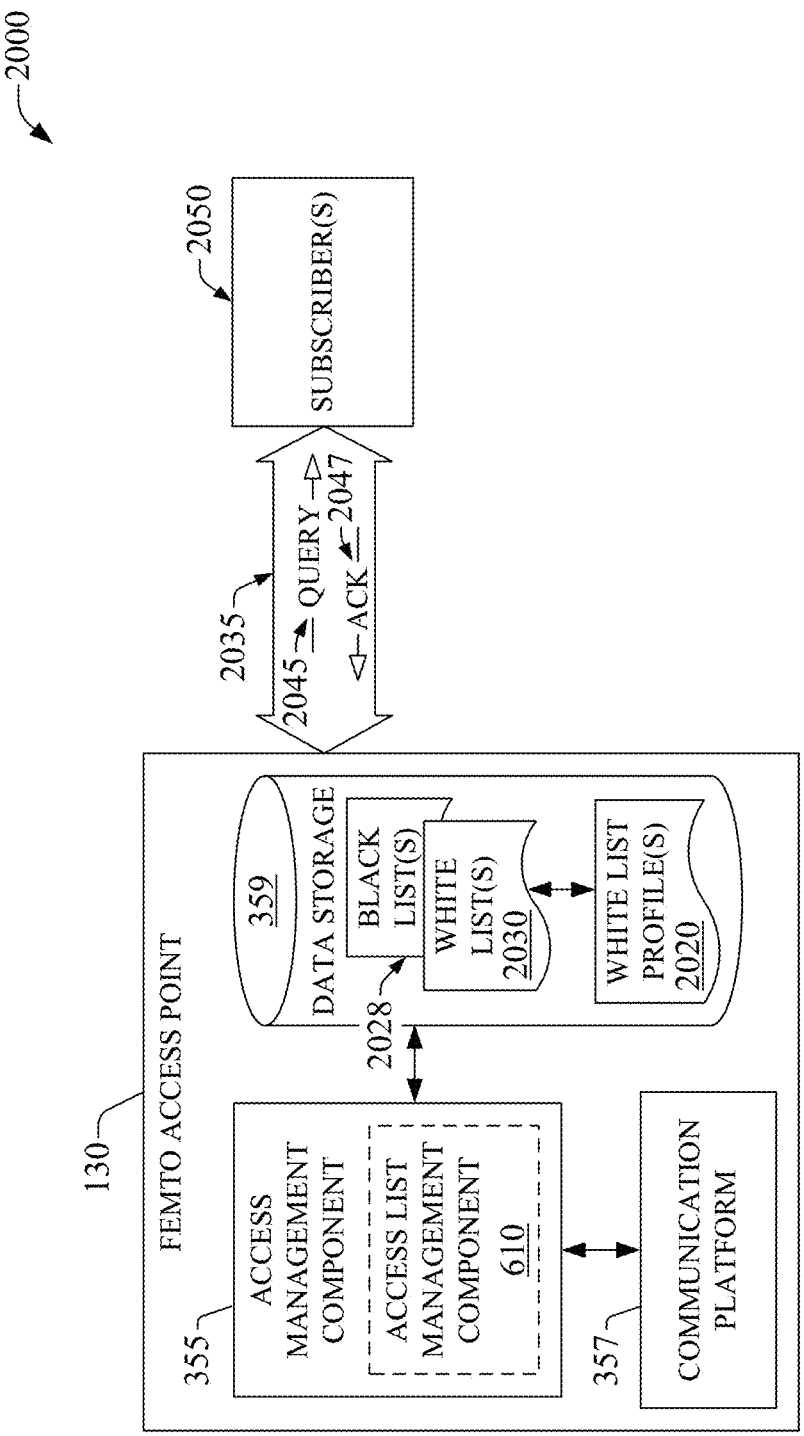
FIG. 20 is a block diagram of an example system that manages a defined logic of how content(s) in access control list(s), e.g., white list(s) or black list(s), is maintained on a white list profile retained in a database in accordance with aspects described herein.

FIG. 20 is a block diagram of an example system 2000 that manages a defined logic of how content(s) (e.g., MSISDNs, IMSIs, IMEIs . . . ) in access control list(s), e.g., white list(s) or black list(s), are maintained on a white list profile retained in a database, which can be embodied in data storage 359. Access management component 355, which can comprise an access list (e.g., white list) management component 610, can develop white list profile(s) 2020 that applies logic and parameters that control, or manage, content (e.g., attribute fields) in white list(s) 2030 such as subscriber station numbers (e.g., MSISDNs, IMSIs, IMEIs . . . ), codes, or tokens. White list profile(s) 2020 and white list(s) 2030 can be stored in data storage 359; it should be appreciated that while data storage 359 is illustrated to reside within femto access point 130, such storage can reside in a network management component (e.g., component 1605), or can be functionally coupled thereof.

As described above in connection with example system 600, white list profile(s) 2020 parameters that control utilization logic of white list(s) 2030 content include, without being limited to including: (i) temporary access parameters, e.g., full access for a specific time interval such as days or hours; (ii) parameters that establish access only within a window of time in a day (voice and data allowed from 9:00 a-6:00 p, or voice allowed after 9:00 p which can facilitate billing schemes already established by an operator/service provider); (iii) parameters for access to specific applications such as scheduler, calendar(s), news streaming, authoring tools, gaming, video and music, etc; (iv) parameters for access to femto AP 130 coverage with specific QoS profile(s), band width, allocated power for communication, or the like.

In another aspect, as indicate above, logic within white list profile(s) 2020 can implement parameters to determine how long access to femto coverage is granted. For instance, when a timer associated with temporary access expires, a query 2045 can be triggered or conveyed (e.g., through a wired or wireless link 2035) to either a subscriber that operates a device associated with the managed identifier (e.g., MSISDN, IMSI, EMEI) in order to prompt or request renewed access, or to a subscriber that operates femto access point 130. The message request, e.g., query 2045, can prompt the subscriber that owns femto AP 130 whether an extension is to be granted or not. When a request is not granted by a subscriber that operates femto AP 130 or there is no reply, e.g., acknowledgement 2045, from the subscriber owner, access to femto coverage expires and the identifier (e.g., MSISDN, or substantially any identifier code or token) linked to an identified mobile device is deleted from a corresponding white list(s) 2030 within data storage 359. It should be appreciated that the deletion can be "soft," e.g., the identifier is flagged as inactive, or "hard," wherein the identifier is deleted and a field or slot in a white list(s) 1420 is made available. Conversely, a positive response, e.g., acknowledgement (ACK) 2047, from subscriber owner can allow access to continue based on either parameters extant in white list profile(s) 1420, or newly defined or negotiated access logic parameters. It is to be noted that query 1445 can be conveyed via an online GUI, an email message, a SMS message, MMS message, a voice mail, a web prompt, and the like.

Figure 21:
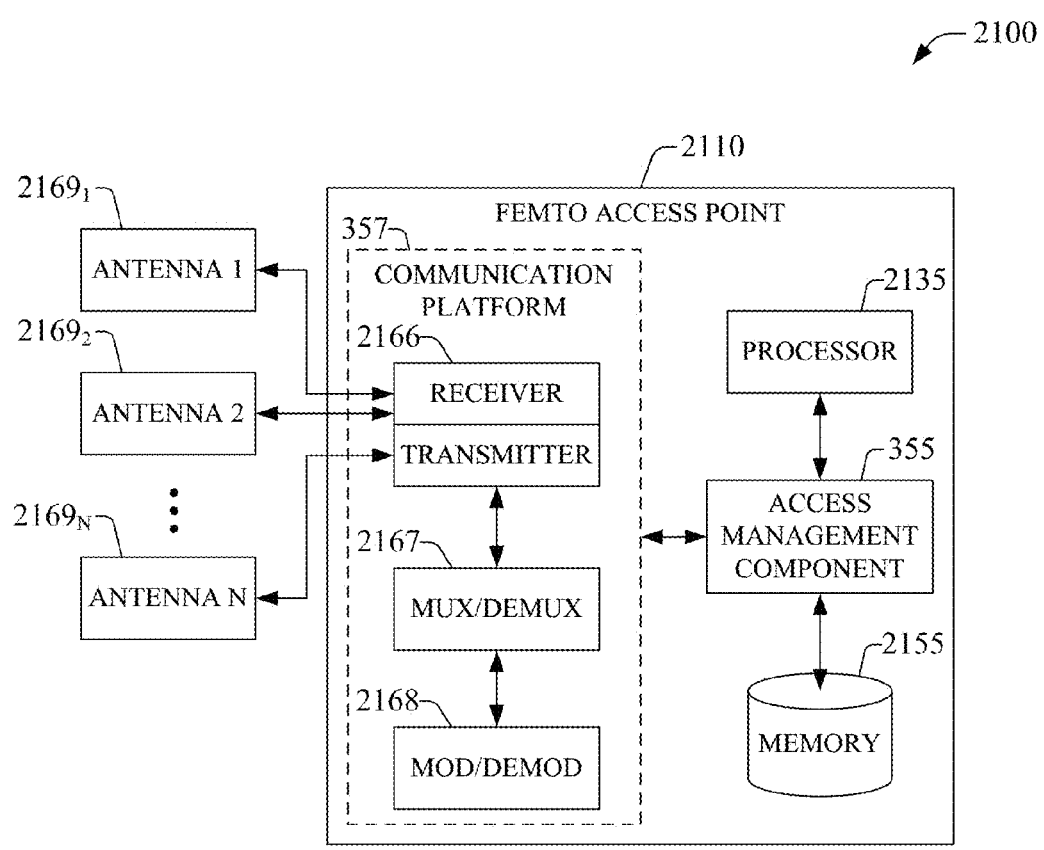
FIG. 21 is a block diagram of an example femto access point that operates in accordance with aspects disclosed in the subject specification.
Figure 22:
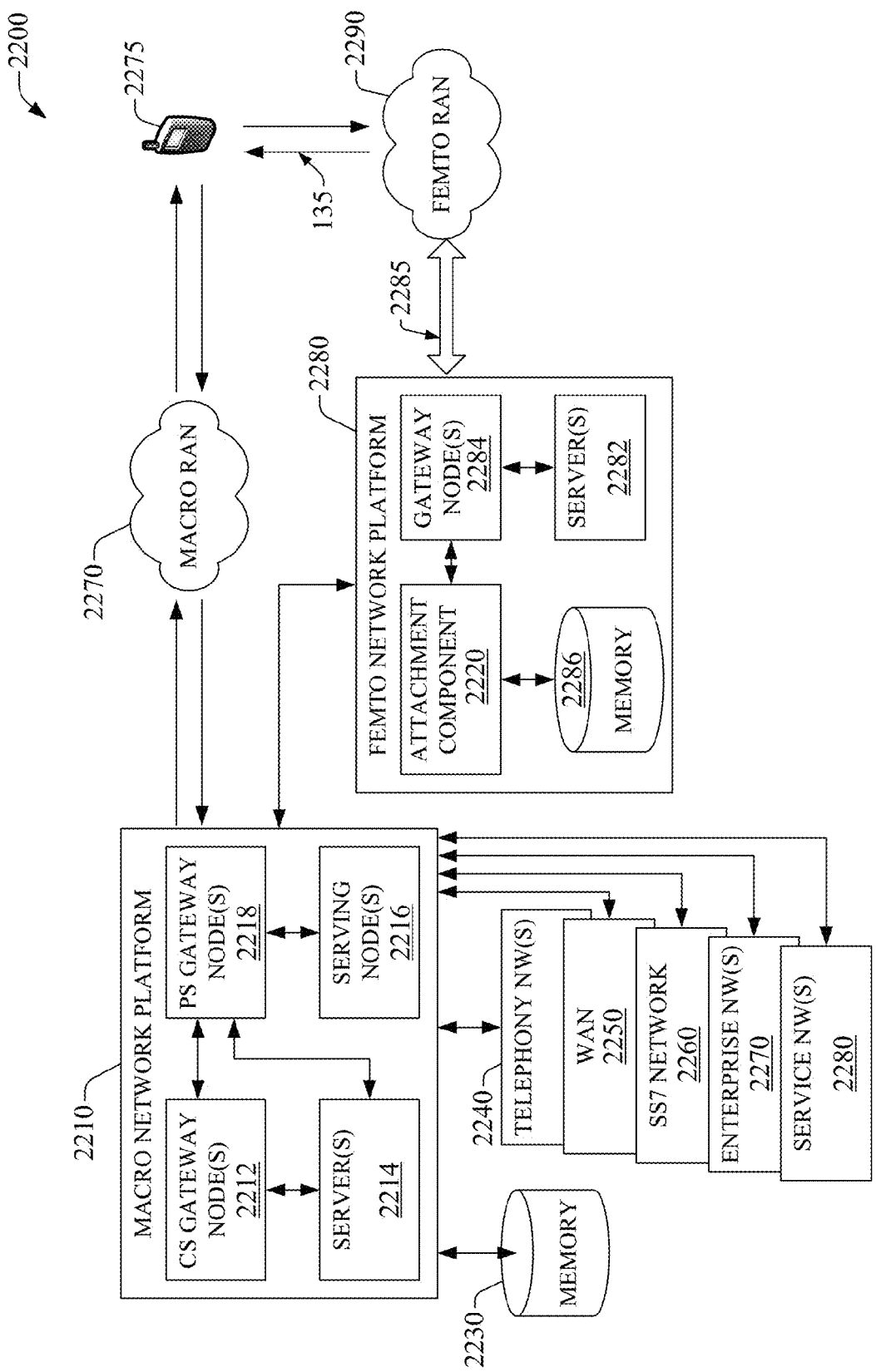
FIG. 22 illustrates example macro and femto wireless network environments that can enable and implement various aspects of the subject application, and can exploit femto APs that operate according to the various aspects.

To provide further context for various aspects or features of the subject specification, in system in which aspects or features of the subject application can be exploited, FIG. 21 illustrates a block diagram of an example embodiment 2100 of a femto access point that can enable and exploit and manage femto coverage via access control list(s), or white list(s), in accordance with aspects described herein. In addition, FIG. 22 illustrates a block diagram of an illustrative telecommunication network 2200 that can enable or implement, and exploit features and aspects described herein. Those skilled in the art will recognize that the specification also be implemented through program modules stored in a memory and executed by a processor, and/or other combination of hardware and software.

With respect to FIG. 21, in embodiment 2100, femto AP 2110 can receive and transmit signal(s) from and to wireless devices like macro and femto access points, access terminals, wireless ports and routers, and the like, through a set of antennas $2169_1$-$2169_N$. It should be appreciated that while antennas $2169_1$-$2169_N$ are a part of communication platform 357 which comprises electronic components and associated circuitry that provides for processing and manipulation of received signal(s) and signal(s) to be transmitted. In an aspect, communication platform 357 includes a receiver/transmitter 2166 that can convert signal from analog to digital upon reception, and from digital to analog upon transmission. In addition, receiver/transmitter 2166 can divide a single data stream into multiple, parallel data streams, or perform the reciprocal operation. Coupled to receiver/transmitter 2166 is a multiplexer/demultiplexer 2167 that facilitates manipulation of signal in time and frequency space. Electronic component 2167 can multiplex information (data/traffic and control/signaling) according to various multiplexing schemes such as time division multiplexing (TDM), frequency division multiplexing (FDM), orthogonal frequency division multiplexing (OFDM), code division multiplexing (CDM), space division multiplexing (SDM). In addition, mux/demux component 2167 can scramble and spread information (e.g., codes) according to substantially any code known in the art; e.g., Hadamard-Walsh codes, Baker codes, Kasami codes, polyphase codes, and so on. A modulator/demodulator 2168 is also a part of operational group 2125, and can modulate information according to multiple modulation techniques, such as frequency modulation, amplitude modulation (e.g., M-ary quadrature amplitude modulation (QAM), with M a positive integer), phase-shift keying (PSK), and the like.

Femto access point 2110 also includes a processor 2135 configured to confer functionality, at least partially, to substantially any electronic component in the femto access point 2110. In particular, processor 2135 can facilitate access management component 355 to operate in accordance to aspects disclosed herein. In addition, processor 2135 can facilitate operations on data (e.g., symbols, bits, or chips) for multiplexing/demultiplexing, such as effecting direct and inverse fast Fourier transforms, selection of modulation rates, selection of data packet formats, inter-packet times, etc. A memory 2155 can store data structures, code instructions, system or device information like policies and specifications, code sequences for scrambling, spreading and pilot transmission, floor plan configuration, access point deployment and frequency plans, scheduling policies, and so on.

In embodiment 2100, processor 2134 is coupled to the memory 2155 in order to store and retrieve information necessary to operate and/or confer functionality to communication platform 255, access management component 235, and other operational aspects of femto access point 2110.

With respect to FIG. 22, wireless communication environment 2200 includes two wireless network platforms: (i) A macro network platform 2210 which serves, or facilitates communication with user equipment 2275 (e.g., mobile $120_A$) via a macro radio access network (RAN) 2270. It should be appreciated that in cellular wireless technologies (e.g., 3GPP UMTS, High-Speed Packet Access (HSPA), 3GPP LTE, 3GPP2 UMB), macro network platform 2210 is embodied in a Core Network. (ii) A femto network platform 2280, which can provide communication with UE 2275 through a femto RAN 2290, which is linked to the femto network platform 2280 via backhaul pipe(s) 2285 (e.g., backhaul link(s) 140). It should be appreciated that macro network platform 2210 typically hands off UE 2275 to femto network platform 2210 once UE 2275 attaches (e.g., through macro-to-femto handover) to femto RAN 2290, which includes a set of deployed femto APs (e.g., femto AP 130) that can operate in accordance with aspects described herein.

It is noted that RAN includes base station(s), or access point(s), and its associated electronic circuitry and deployment site(s), in addition to a wireless radio link operated in accordance with the base station(s). Accordingly, macro RAN 2270 can comprise various coverage cells like cell 105, while femto RAN 2290 can comprise multiple femto cell access points such as femto AP 130. Deployment density in femto RAN 2290 is substantially higher than in macro RAN 2270.

Generally, both macro and femto network platforms 2210 and 2280 include components, e.g., nodes, gateways, interfaces, servers, or platforms, that facilitate both packet-switched (PS) (e.g., internet protocol (IP), frame relay, asynchronous transfer mode (ATM)) and circuit-switched (CS) traffic (e.g., voice and data) and control generation for networked wireless communication. In an aspect of the subject application, macro network platform 2210 includes CS gateway node(s) 1812 which can interface CS traffic received from legacy networks like telephony network(s) 2240 (e.g., public switched telephone network (PSTN), or public land mobile network (PLMN)) or a SS7 network 2260. Circuit switched gateway 2212 can authorize and authenticate traffic (e.g., voice) arising from such networks. Additionally, CS gateway 2212 can access mobility, or roaming, data generated through SS7 network 2260; for instance, mobility data stored in a VLR, which can reside in memory 2230. Moreover, CS gateway node(s) 2212 interfaces CS-based traffic and signaling and gateway node(s) 2218. As an example, in a 3GPP UMTS network, PS gateway node(s) 2218 can be embodied in gateway GPRS support node(s) (GGSN).

In addition to receiving and processing CS-switched traffic and signaling, PS gateway node(s) 1818 can authorize and authenticate PS-based data sessions with served (e.g., through macro RAN) wireless devices. Data sessions can include traffic exchange with networks external to the macro network platform 2210, like wide area network(s) (WANs) 2250, enterprise networks (NW(s)) 1870 (e.g., enhanced 911), or service NW(s) 2280 like IP multimedia subsystem (IMS); it should be appreciated that local area network(s) (LANs), which may be a part of enterprise NW(s), can also be interfaced with macro network platform 2210 through PS gateway node(s) 2218. Packet-switched gateway node(s) 2218 generates packet data contexts when a data session is established. To that end, in an aspect, PS gateway node(s) 2218 can include a tunnel interface (e.g., tunnel termination gateway (TTG) in 3GPP UMTS network(s); not shown) which can facilitate packetized communication with disparate wireless network(s), such as Wi-Fi networks. It should be further appreciated that the packetized communication can include multiple flows that can be generated through server(s) 2214. It is to be noted that in 3GPP UMTS network(s), PS gateway node(s) 2218 (e.g., GGSN) and tunnel interface (e.g., TTG) comprise a packet data gateway (PDG).

Macro network platform 2210 also includes serving node(s) 2216 that convey the various packetized flows of information, or data streams, received through PS gateway node(s) 2218. As an example, in a 3GPP UMTS network, serving node(s) can be embodied in serving GPRS support node(s) (SGSN).

As indicated above, server(s) 2214 in macro network platform 2210 can execute numerous applications (e.g., location services, online gaming, wireless banking, wireless device management . . . ) that generate multiple disparate packetized data streams or flows, and manage (e.g., schedule, queue, format . . . ) such flows. Such application(s), for example can include add-on features to standard services provided by macro network platform 2210. In an aspect of the subject application, one or more of server(s) 2214 can embody an access list management component as described hereinbefore in connection with the various illustrative example systems. Data streams can be conveyed to PS gateway node(s) 2218 for authorization/authentication and initiation of a data session, and to serving node(s) 2216 for communication thereafter. Server(s) 2214 can also effect security (e.g., implement one or more firewalls) of macro network platform 2210 to ensure network's operation and data integrity in addition to authorization and authentication procedures that CS gateway node(s) 2212 and PS gateway node(s) 2218 can enact. Moreover, server(s) 2214 can provision services from external network(s), e.g., WAN 2250, or Global Positioning System (GPS) network(s), which can be a part of enterprise NW(s) 2280. It is to be noted that server(s) 2214 can include one or more processor configured to confer at least in part the functionality of macro network platform 2210. To that end, the one or more processor can execute code instructions stored in memory 2230, for example.

In example wireless environment 2200, memory 2230 stores information related to operation of macro network platform 2210. Information can include business data associated with subscribers; market plans and strategies, e.g., promotional campaigns, business partnerships; operational data for mobile devices served through macro network platform; service and privacy policies; end-user service logs for law enforcement; and so forth. Memory 2230 can also store information from at least one of telephony network(s) 2240, WAN 2250, SS7 network 2260, enterprise NW(s) 2270, or service NW(s) 2280.

Regarding femto network platform 2280, it includes a femto gateway node(s) 2284, which have substantially the same functionality as PS gateway node(s) 2218. Additionally, femto gateway node(s) 2284 can also include substantially all functionality of serving node(s) 2216. Disparate gateway node(s) 2284 can control or operate disparate sets of deployed femto APs, which can be a part of femto RAN 2290. In an aspect of the subject application, femto gateway node(s) 2284 can aggregate operational data received from deployed femto APs. Moreover, femto gateway node(s) 2284, can convey received attachment signaling to attachment component 2220. It should be appreciated that while attachment component is illustrated as external to gateway node(s) 2284, attachment component 2220 can be an integral part of gateway node(s) 2284.

Attachment component 2220 can facilitate macro-to-femto and femto-to-macro handover with attachment to a femto AP (e.g., femto AP 130) dictated in accordance to a white list (e.g., white list(s) 220) and/or a white list profile (e.g., white list profile(s) 222). In an aspect, attachment component 2220 can include a determination of whether a white list resides within femto AP and whether a mobile station that is attempting attachment is whitelisted as described in the subject application. It is noted, in an aspect, that when a whitelisted mobile station is allowed to attach to the femto AP, attachment component 2220 can establish femto service in accordance with privileges, or access logic, configured in a white list profile (e.g., white list profile(s) 222).

Memory 2286 can retain additional information relevant to operation of the various components of femto network platform 2280. For example operational information that can be stored in memory 2286 can comprise, but is not limited to, subscriber intelligence; contracted services; maintenance and service records; femto cell configuration (e.g., devices served through femto RAN 2290; authorized subscribers associated with one or more deployed femto APs); service policies and specifications; privacy policies; add-on features; so forth.

Server(s) 2282 have substantially the same functionality as described in connection with server(s) 2214. In an aspect, server(s) 2282 can execute multiple application(s) that provide service (e.g., voice and data) to wireless devices served through femto RAN 2290. Server(s) 2282 can also provide security features to femto network platform. In addition, server(s) 2282 can manage (e.g., schedule, queue, format . . . ) substantially all packetized flows (e.g., IP-based, frame relay-based, ATM-based) it generates in addition to data received from macro network platform 2210. Furthermore, server(s) 2282 can effect provisioning of femto cell service, and effect operations and maintenance. It is to be noted that server(s) 2282 can embody provisioning server 345, and can populate white list(s) and white list profile(s) in accordance with aspects described herein. It is to be noted that server(s) 2282 can include one or more processors configured to provide at least in part the functionality of femto network platform 2280. To that end, the one or more processors can execute code instructions stored in memory 2286, for example.

Various aspects or features described herein may be implemented as a method, apparatus, or article of manufacture using standard programming and/or engineering techniques. Implementation(s) that include software or firmware can be implemented at least in part through program modules stored in a memory and executed by a processor. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disc (CD), digital versatile disc (DVD), blu-ray disc (BD) . . . ), smart cards, and flash memory devices (e.g., card, stick, key drive . . . ).

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nanoscale architectures such as, but not limited to, molecular and quantum-dot based transistors, switches and gates, in order to optimize space usage or enhance performance of user equipment. A processor may also be implemented as a combination of computing processing units.

In the subject specification, terms such as "data store," data storage," "database," and substantially any other information storage component relevant to operation and functionality of a component, refer to "memory components," or entities embodied in a "memory" or components comprising the memory. For example, information relevant to operation of various components described in the disclosed subject matter, and that can be stored in a memory, can comprise, but is not limited to comprising, subscriber information; femto cell configuration (e.g., devices served by a femto AP; access control lists, or white lists) or service policies and specifications; privacy policies; and so forth. It will be appreciated that the memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

What has been described above includes examples of systems and methods that provide advantages of the subject application. It is, of course, not possible to describe every conceivable combination of components or methodologies for purposes of describing the claimed subject matter, but one of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A system, comprising:
    a processor; and
    a memory that stores executable instructions that, when executed by the processor, facilitate performance of operations, comprising:
        selecting femto access point devices based on relevancy scores assigned to locations of user equipment and an association criterion; and
        facilitating a transmission of notification data to the user equipment, wherein the notification data is indicative of identifications of the femto access point devices.

2. The system of claim 1, wherein the selecting comprises:
    determining a relationship between the femto access point devices; and
    determining that the relationship satisfies the association criterion.

3. The system of claim 1, wherein the notification data is transmitted to the user equipment via a voice call.

4. The system of claim 1, wherein the notification data is transmitted to the user equipment via a text message.

5. The system of claim 1, wherein the association criterion is determined based on location data associated with the femto access point devices.

6. The system of claim 1, wherein the operations further comprise:
    determining pattern data indicative of a pattern associated with the locations of the user equipment, wherein the selecting comprises selecting the femto access point devices based on the pattern data.

7. The system of claim 6, wherein the operations further comprise:
    determining that respective locations of the femto access point devices satisfy a location criterion associated with the pattern data.

8. The system of claim 1, wherein the relevancy scores are greater than a first value based on corresponding locations of the user equipment being associated with a defined geographical areas.

9. The system of claim 1, wherein the association criterion is determined based on subscriber segment data associated with the user equipment.

10. The system of claim 1, wherein the association criterion is determined based on market data associated with the user equipment.

11. The system of claim 1, wherein the operations further comprise:
    in response to the facilitating the transmission, facilitating population of access control data associated with a femto access point device of the femto access point devices.

12. A method, comprising:
    determining, by a system comprising a processor, an association criterion related to a user equipment; and
    facilitating, by the system, a transmission of notification data to the user equipment, wherein the notification data is indicative of identifications of femto access point devices that are selected based on relevancy scores assigned to locations of the user equipment and the association criterion.

13. The method of claim 12, further comprising:
    in response to the facilitating the transmission, facilitating, by the system, management of access control data associated with a femto access point device of the femto access point devices.

14. The method of claim 13, further comprising:
    in response to the facilitating the transmission, receiving, by the system, input data from the user equipment, wherein the facilitating the management of the access control data is based on the input data.

15. The method of claim 12, wherein the facilitating the transmission comprises facilitating a transmission of a text message.

16. The method of claim 12, wherein the facilitating the transmission comprises facilitating a transmission of a voice call.

17. The method of claim 12, further comprising:
    selecting, by the system, the femto access point devices based on an analysis of data accessed from network data stores.

18. The method of claim 17, wherein the selecting comprises selecting the femto access point devices based on privacy policy data.

19. A computer readable storage device comprising executable instructions that, in response to execution, cause a system comprising a processor to perform operations, comprising:
- based on relevancy scores assigned to locations of user equipment, determining that femto access point devices satisfy an association criterion related to the user equipment; and
- facilitating a transmission of notification data to the user equipment, wherein the notification data is indicative of identifications of the femto access point devices.

20. The computer readable storage device of claim 19, wherein the operations further comprise:
- facilitating management of an access control data structure associated with a femto access point device of the femto access point devices based on the transmission.

\* \* \* \* \*